US006711423B2

(12) United States Patent
Colvin, Jr.

(10) Patent No.: US 6,711,423 B2
(45) Date of Patent: *Mar. 23, 2004

(54) OPTICAL-BASED SENSING DEVICES

(75) Inventor: Arthur E. Colvin, Jr., Mt. Airy, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/963,798

(22) Filed: Sep. 27, 2001

(65) Prior Publication Data

US 2002/0026108 A1 Feb. 28, 2002

Related U.S. Application Data

(63) Continuation-in-part of application No. 09/383,148, filed on Aug. 26, 1999, now Pat. No. 6,330,464, and a continuation-in-part of application No. 09/304,831, filed on May 5, 1999, now abandoned, and a continuation-in-part of application No. 09/140,747, filed on Aug. 26, 1998, now Pat. No. 6,304,766.

(51) Int. Cl.[7] ............................. A61B 5/00; A61B 5/07
(52) U.S. Cl. ...................... 600/317; 600/302; 600/316; 128/899
(58) Field of Search ............................. 600/316, 317, 600/302; 128/899; 427/2.13

(56) References Cited

U.S. PATENT DOCUMENTS

| 3,229,684 A | 1/1966 | Nagumo et al. |
| 3,399,667 A | 9/1968 | Nishimoto et al. |
| 3,576,554 A | 4/1971 | Temps, Jr. et al. |
| 3,612,866 A | 10/1971 | Stevens |

(List continued on next page.)

FOREIGN PATENT DOCUMENTS

| DE | 4341903 | 6/1995 |
| DE | 19615380 A1 | 3/1997 |

(List continued on next page.)

OTHER PUBLICATIONS

Jie Lin et al. "Sol–gel glass as a matrix for chemical and biochemical sensing" *Trends in Analytical Chemistry*, 16(4):200–211 (1997).

(List continued on next page.)

*Primary Examiner*—Max F. Hindenburg
*Assistant Examiner*—David J. McCrosky
(74) *Attorney, Agent, or Firm*—Rothwell, Figg, Ernst & Manbeck

(57) ABSTRACT

An optical-based sensor for detecting the presence or amount of an analyte using both indicator and reference channels. The sensor has a sensor body with a source of radiation embedded therein. Radiation emitted by the source interacts with indicator membrane indicator molecules proximate the surface of the body. At least one optical characteristic of these indicator molecules varies with analyte concentration. For example, the level of fluorescence of fluorescent indicator molecules or the amount of light absorbed by light-absorbing indicator molecules can vary as a function of analyte concentration. In addition, radiation emitted by the source also interacts with reference membrane indicator molecules proximate the surface of the body. Radiation (e.g., light) emitted or reflected by these indicator molecules enters and is internally reflected in the sensor body. Photosensitive elements within the sensor body generate both indicator channel and reference channel signals to provide an accurate indication of the concentration of the analyte. Preferred embodiments are totally self-contained and are sized and shaped for use in vivo in a human being. Such embodiments preferably include a power source, e.g. an inductor, which powers the source of radiation using external means, as well as a transmitter, e.g. an inductor, to transmit to external pickup means the signal representing the level of analyte.

15 Claims, 38 Drawing Sheets

U.S. PATENT DOCUMENTS

| | | |
|---|---|---|
| 3,649,833 A | 3/1972 | Leaf |
| 3,800,300 A | 3/1974 | Van Oosterhout |
| 3,839,708 A | 10/1974 | Bredesen et al. |
| 3,853,117 A | 12/1974 | Murr |
| 3,872,455 A | 3/1975 | Fuller et al. |
| 3,893,111 A | 7/1975 | Cotter |
| 3,949,388 A | 4/1976 | Fuller |
| 3,972,320 A | 8/1976 | Kalman |
| 4,041,954 A | 8/1977 | Ohara |
| 4,160,971 A | 7/1979 | Jones et al. |
| 4,186,749 A | 2/1980 | Fryer |
| 4,262,632 A | 4/1981 | Hanton et al. |
| 4,361,153 A | 11/1982 | Slocum et al. |
| 4,401,122 A | 8/1983 | Clark, Jr. |
| 4,531,526 A | 7/1985 | Genest |
| 4,677,008 A | 6/1987 | Webb |
| 4,680,268 A | 7/1987 | Clark, Jr. |
| 4,703,756 A | 11/1987 | Gough et al. |
| 4,704,029 A | 11/1987 | Van Heuvelen |
| 4,730,188 A | 3/1988 | Milheiser |
| 4,737,464 A | 4/1988 | McConnell et al. |
| 4,746,830 A | 5/1988 | Holland |
| 4,752,115 A | 6/1988 | Murray, Jr. et al. |
| 4,755,667 A | 7/1988 | Marsoner |
| 4,854,328 A | 8/1989 | Pollack |
| 4,863,470 A | 9/1989 | Carter |
| 4,875,483 A | 10/1989 | Vollmann et al. |
| 4,935,632 A | 6/1990 | Hart |
| 4,992,794 A | 2/1991 | Brouwers |
| 5,010,893 A | 4/1991 | Sholder |
| 5,012,286 A | 4/1991 | Kawano et al. |
| 5,028,918 A | 7/1991 | Giles et al. |
| 5,036,869 A | 8/1991 | Inahara |
| 5,039,490 A | 8/1991 | Marsoner et al. |
| 5,041,826 A | 8/1991 | Milheiser |
| 5,084,699 A | 1/1992 | DeMichele |
| 5,095,309 A | 3/1992 | Troyk et al. |
| 5,143,066 A | 9/1992 | Komives et al. |
| 5,157,262 A | 10/1992 | Marsoner et al. |
| 5,211,129 A | 5/1993 | Taylor et al. |
| 5,218,343 A | 6/1993 | Stobbe et al. |
| 5,235,326 A | 8/1993 | Beigel et al. |
| 5,281,825 A | 1/1994 | Berndt et al. |
| 5,300,120 A | 4/1994 | Knapp et al. |
| 5,314,457 A | 5/1994 | Jeutter et al. |
| 5,342,789 A | 8/1994 | Chick et al. |
| 5,517,313 A | 5/1996 | Colvin, Jr. |
| 5,628,310 A | 5/1997 | Rao et al. |
| 5,630,836 A | 5/1997 | Prem et al. |
| 5,633,724 A | 5/1997 | King et al. |
| 5,674,288 A | 10/1997 | Knapp et al. |
| 5,682,149 A | 10/1997 | Hofman |
| 5,708,957 A | 1/1998 | Chuang et al. |
| 5,725,578 A | 3/1998 | Knapp et al. |
| 5,735,887 A | 4/1998 | Barreras, Sr. et al. |
| 5,833,603 A | 11/1998 | Kovacs et al. |
| 5,855,609 A | 1/1999 | Knapp |
| 5,922,285 A | 7/1999 | Melendez et al. |
| 5,939,609 A | 8/1999 | Knapp et al. |
| 5,977,431 A | 11/1999 | Knapp et al. |
| 6,002,954 A | 12/1999 | Van Antwerp et al. |
| 6,011,984 A | 1/2000 | Van Antwerp et al. |
| 6,304,766 B1 * | 10/2001 | Colvin, Jr. .................. 600/317 |
| 6,330,464 B1 * | 12/2001 | Colvin et al. ............... 600/316 |

FOREIGN PATENT DOCUMENTS

| | | |
|---|---|---|
| DE | 19826294 C1 | 2/2000 |
| EP | 309214 A2 | 3/1989 |
| EP | 309214 A3 | 3/1989 |
| EP | 597566 A1 | 5/1994 |
| EP | 619101 | 12/1994 |
| EP | 646313 | 5/1995 |
| EP | 693271 A1 | 1/1996 |
| EP | 834734 A2 | 4/1998 |
| EP | 834734 A3 | 4/1998 |
| FR | 2680672 | 5/1993 |
| GB | 2258589 | 2/1993 |
| WO | WO 8704900 | 8/1987 |
| WO | WO 9207505 | 5/1992 |
| WO | WO 9616593 A1 | 6/1996 |
| WO | WO 9625978 A1 | 8/1996 |
| WO | WO 9733513 A1 | 9/1997 |
| WO | WO 9852023 A1 | 11/1998 |
| WO | WO 9966309 | 12/1999 |

OTHER PUBLICATIONS

Alan Baron et al. "Submillisecond response times of oxygen–quenched luminescent coatings" *Rev. Sci. Instrum.*, 64(12):3394–3402 (1993).

Brauker et al., "Neovascularization of synthetic membranes directed by membrane microarchitecture", *Journal of Biomedical Materials Research*, vol. 29, 1517–1524 (1995).

Chuang and Arnold, "Radioluminescent Light Source for Optical Oxygen Sensors", *Analytical Chemistry*, vol. 69, No. 10, 1899–1903, 1997.

Geller, et al., "Immunoisolation of Tumor Cells: Generation of Antitumor Immunity Through Indirect Presentation of Antigen", *Journal of Immunotherapy*, 20(2):131–137 (1997).

Geller, et al., "Use of An Immunoisolation Device for Cell Transplantation and Tumor Immunotherapy", Baxter Healthcare Corp., Illinois, pp. 1–23 w/attache Figures 1–7 (undated).

Shamlou et al, "Amphiphilic networks. X. Diffusion of glucose and insulin (and nondiffusion of albumin) through amphilphilic membranes", *Journal of Biomedical Research*, vol. 35, 157–163 (1997).

Kennedy, "Tailoring polymers for biological uses" *Chemtech*, pp. 24–32, Feb. 1994.

Tuan, "Recombinant Protein Protocols, Detection and Isolation", *Methods in Molecular Biology*, vol. 63, pp. 373–387.

Ward, "Development of a Hybrid Artificial Pancreas with a Dense Polyurethan Membrane", *ASAIO Journal*, vol. 39, No. 3, pp. M261–M267.

Wilkins, "Biomaterials for Implanted Closed Loop Insulin Delivery System: A Review", *Biosensors and Bioelectronics* 5, pp. 167–203, 1990.

Advertisement pamphlet entitled "RFID: Everything you need to know" by Motorola Indala Corporation, 1996, 1997 (5 pages).

Pamphlet entitled "Divvying up the biostent market", *BioCentury, The Bernstein Report on BioBusiness*, pp. A6, Aug. 10, 1998.

Advertising pamphlet entitled "Biocompatibility, controlled porosity, inertness, strength and conformability.", *Gore–Tex Medical Products*, 1990 (4 pages).

Product pamphlet for "Preclude Pericardial Membrane", *W.L. Gore& Associates, Inc.*, 1996 (2 pages).

Product pamphlet for "The Duraflow® Biocompatible Treatment", *Baxter Healthcare Corporation*, 1995 (4 pages).

"Laminin–5 inhibits human keratinocyte migration", *Exp Cell Res*, 233:2 330–9, 1998 (abstract only).

"Mini–Portable Reader Standard and Extended Models" Hughes Identification Devices information pamphlet HS5105L Series (4 pages).

"Implantatable Transponder" Trovan Electronic Identification Systems pamphlet, Model—ID 100. (2 pages).

"Hand Held Reader" Trovan Electronic Identification Systems pamphlet, Model—LID 500. (2 pages).

Wouters et al. "A Low Power Multi–Sensor Interface for Injectable Microcompressor–Based Animal Monitoring System" *Sensors and Acutuators A*, 41–42 (1994) 198–206.

"DIOG Database Guide (Standard Search Service)" SRS Information Technologies, 1987 (7 pages).

"Injectable Transponder Small Size" Hughes Identification Devices information pamphlet TX1400L (2 pages).

* cited by examiner

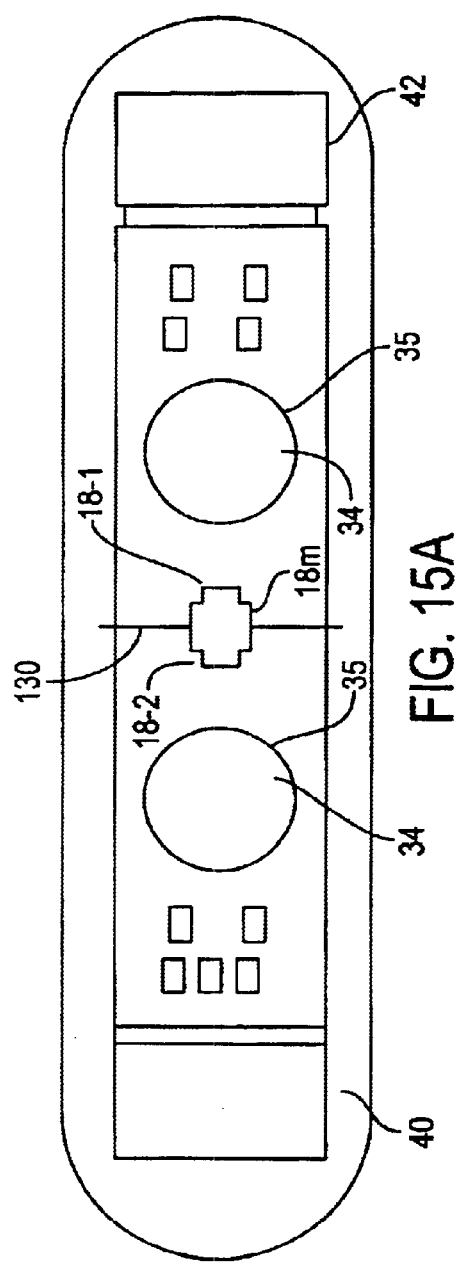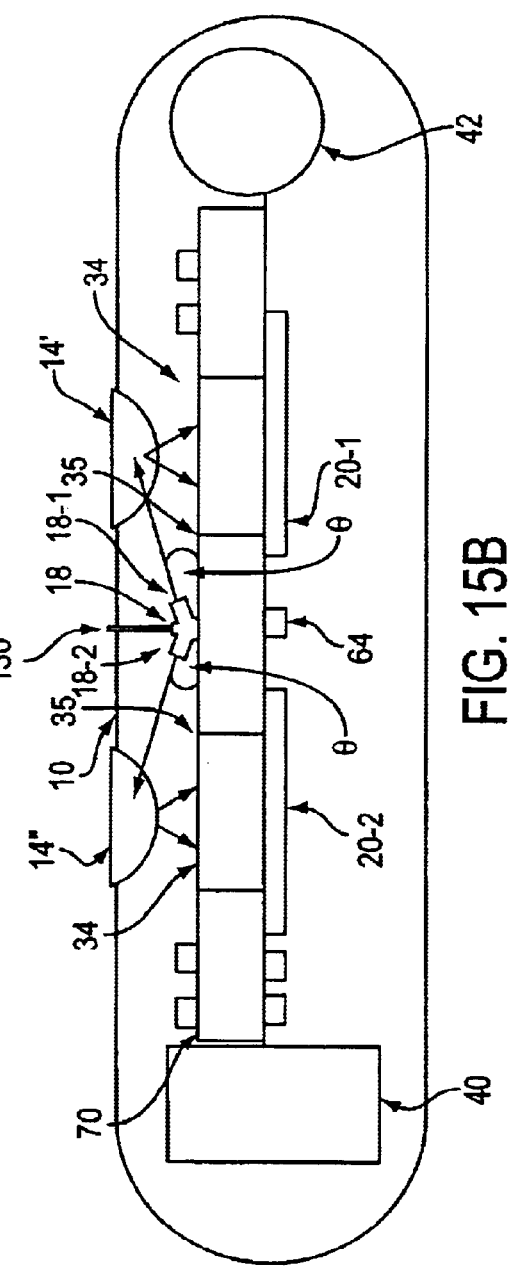

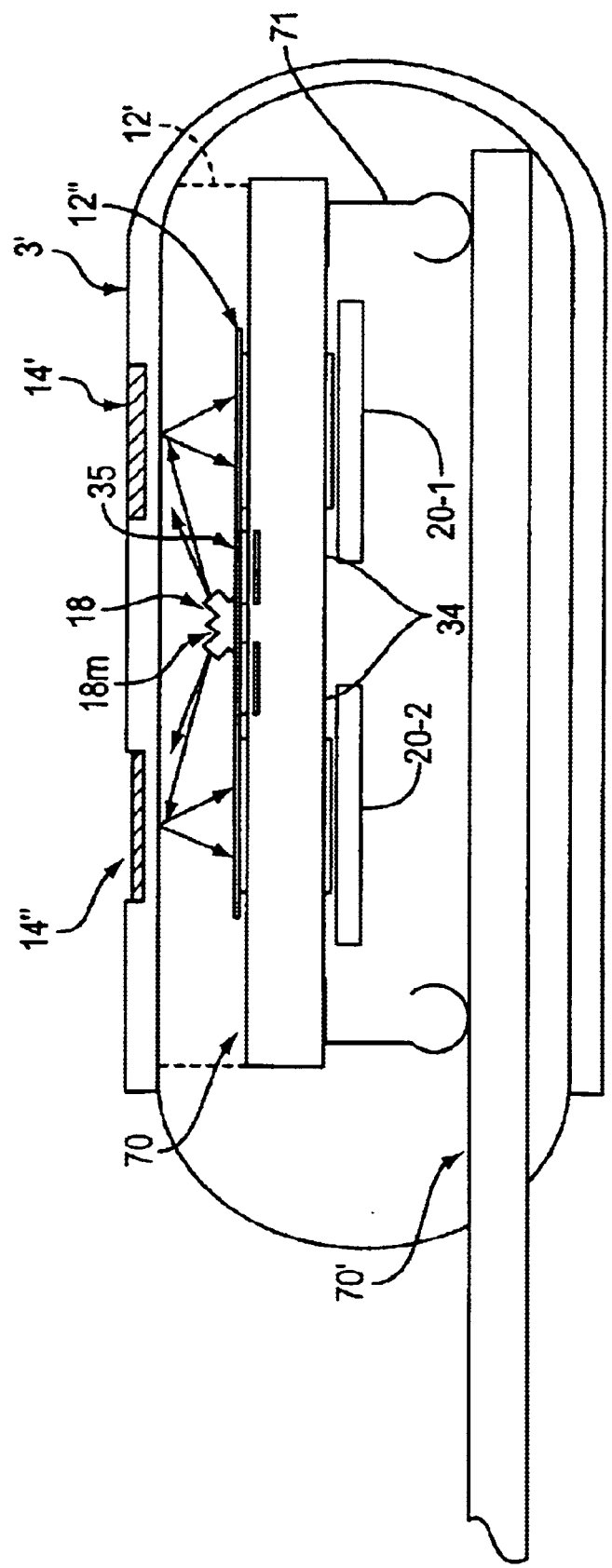

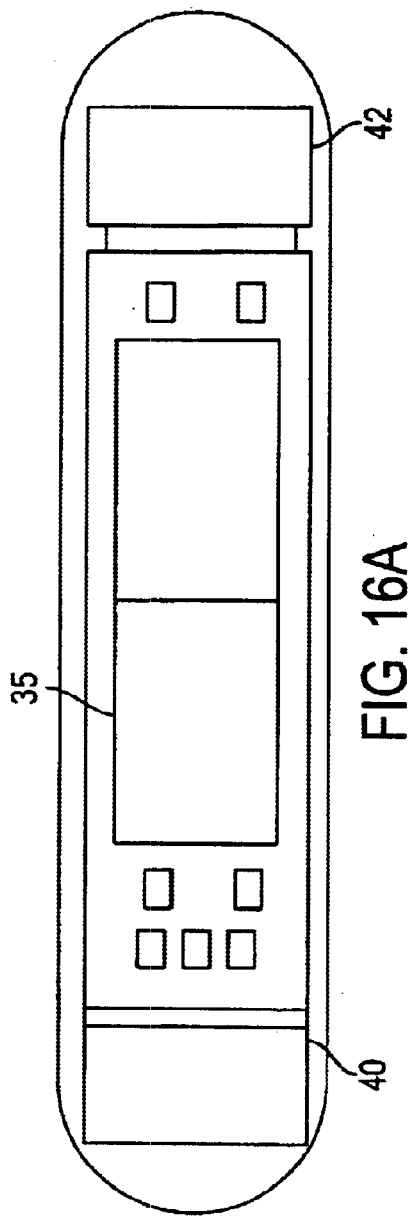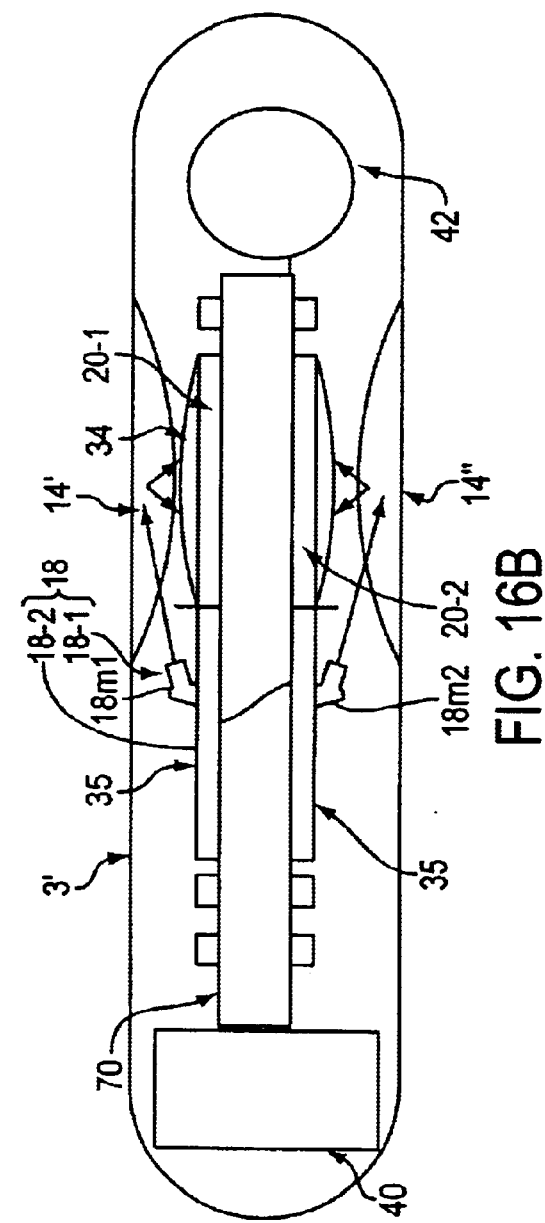

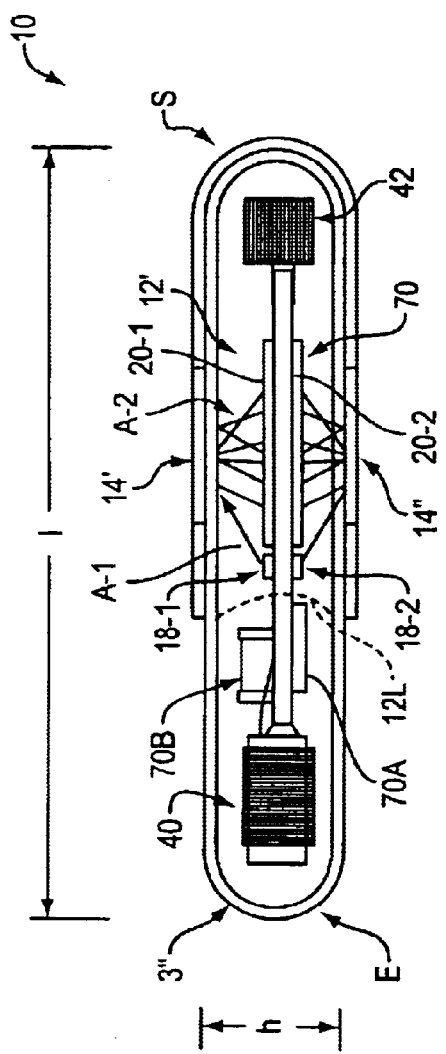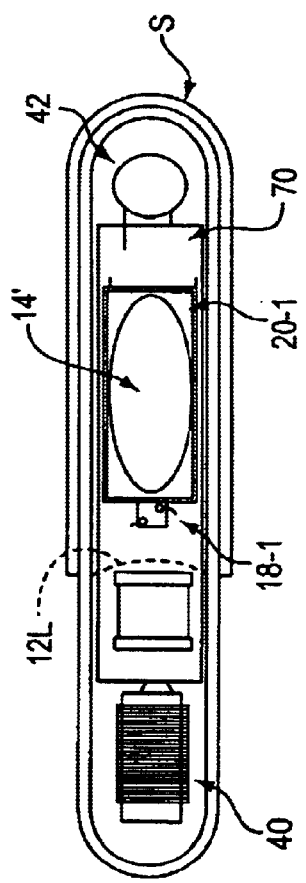

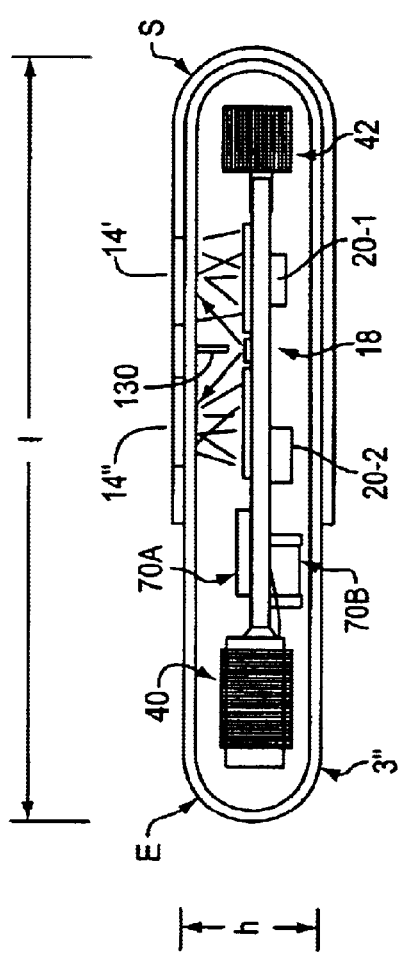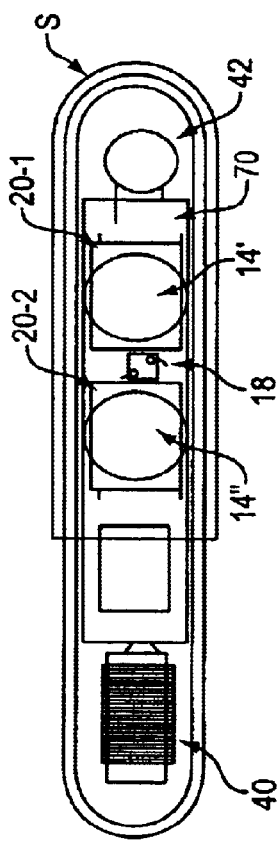
FIG. 17C
FIG. 17D

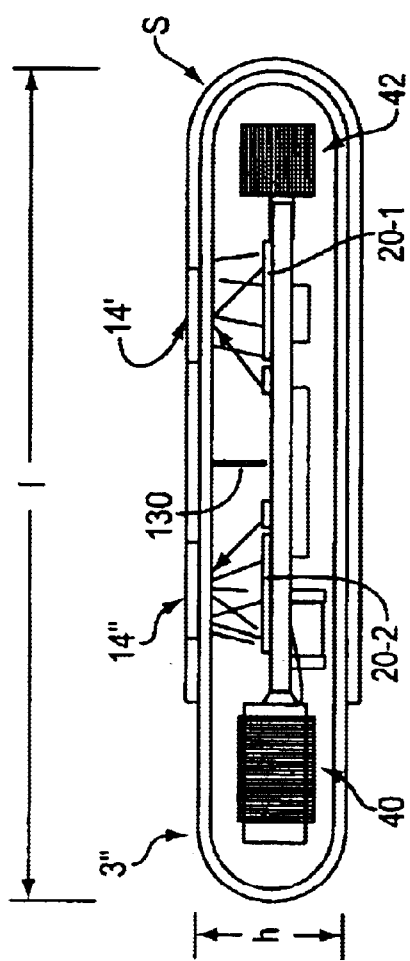
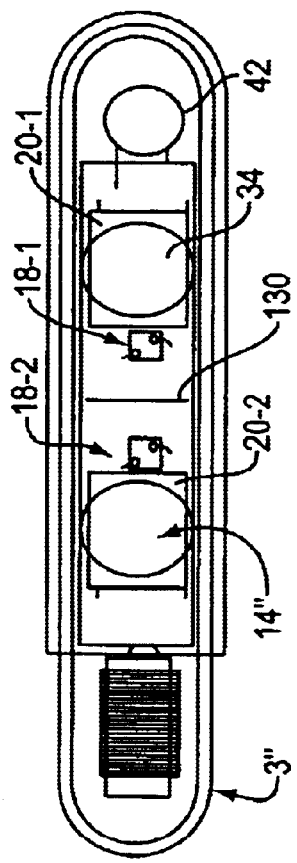
FIG. 17E
FIG. 17F

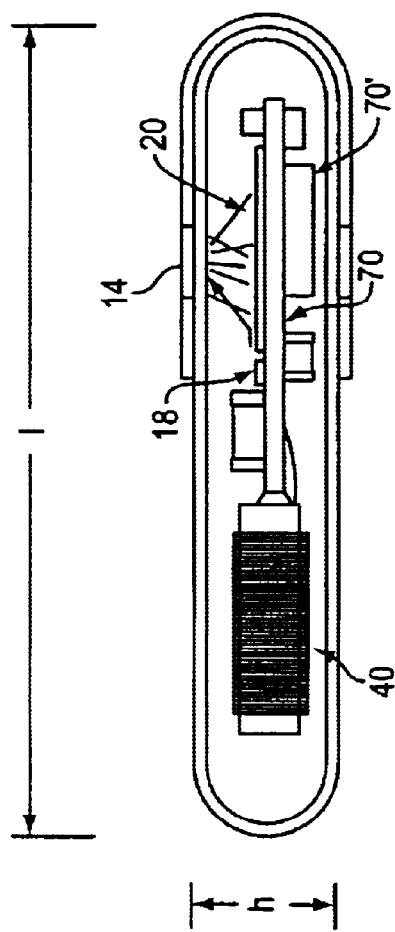
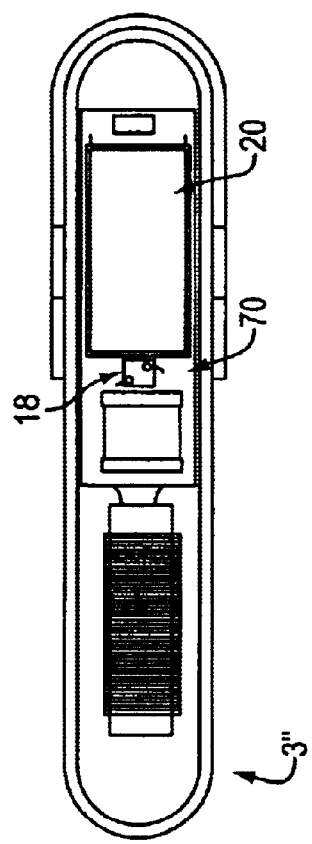
FIG. 18A
FIG. 18B

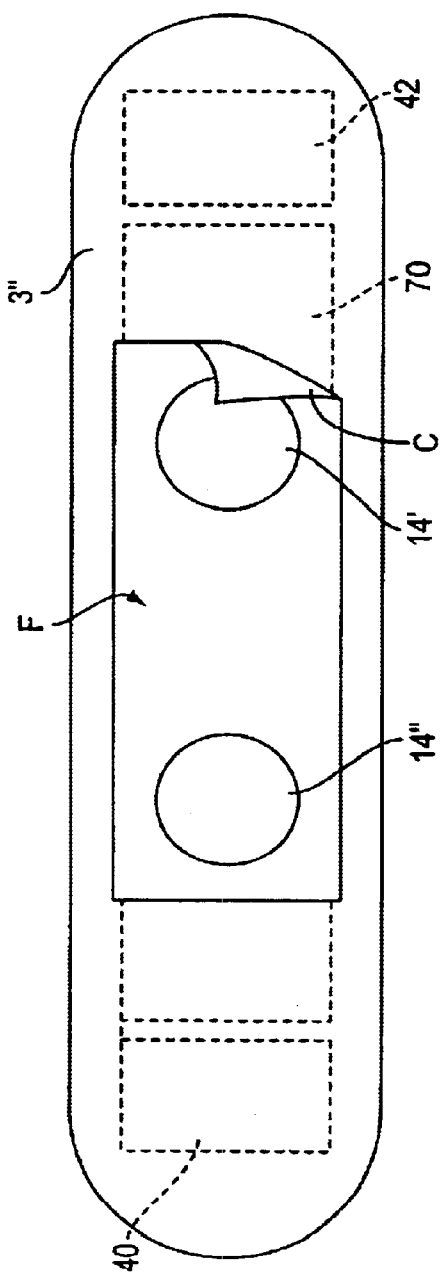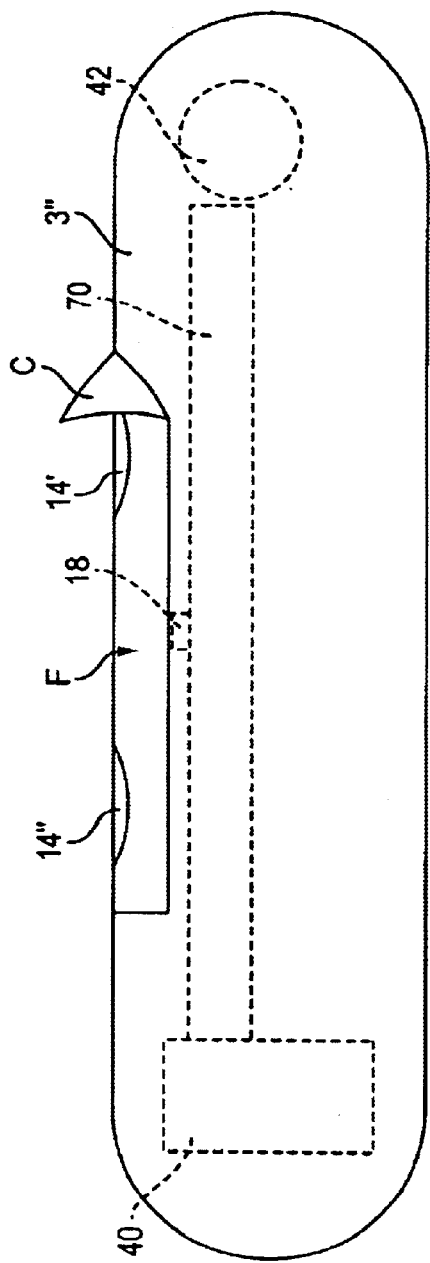

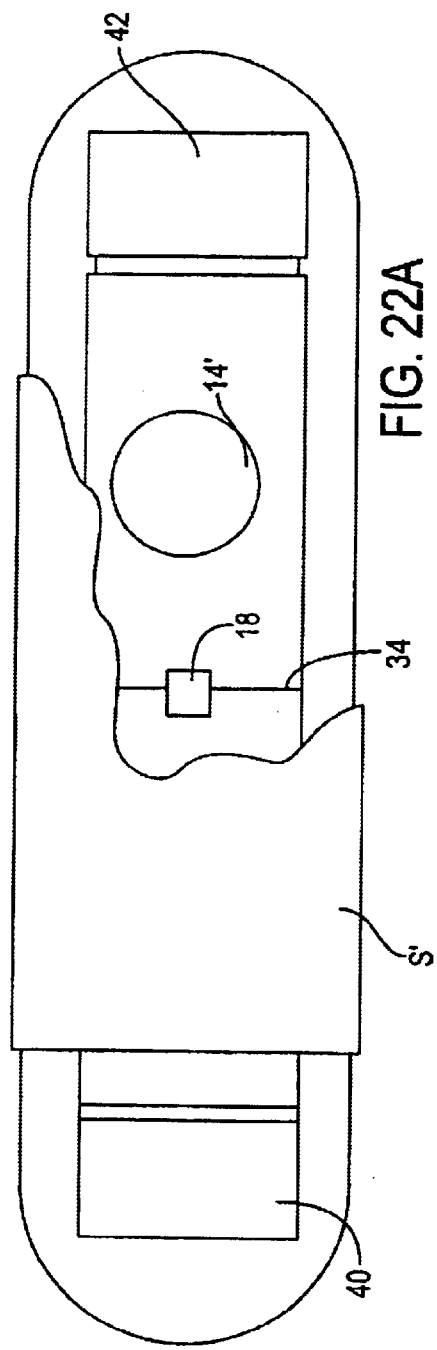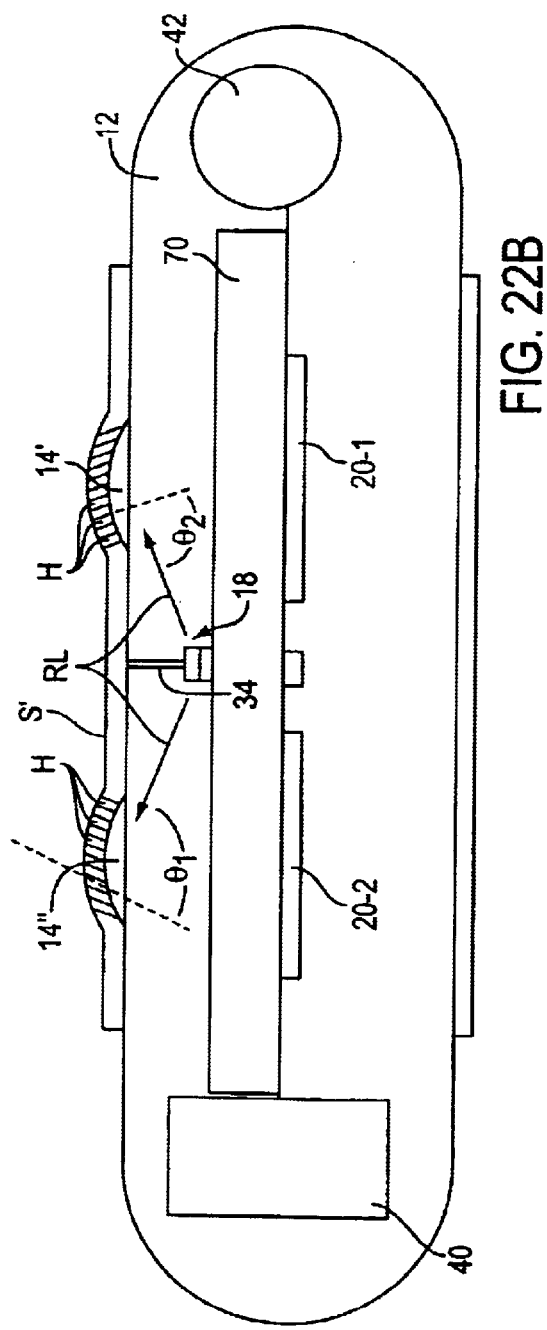

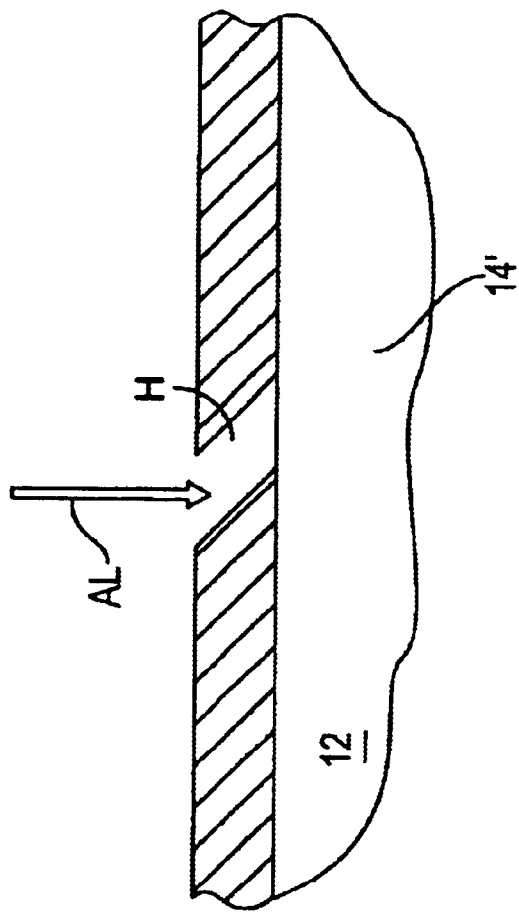

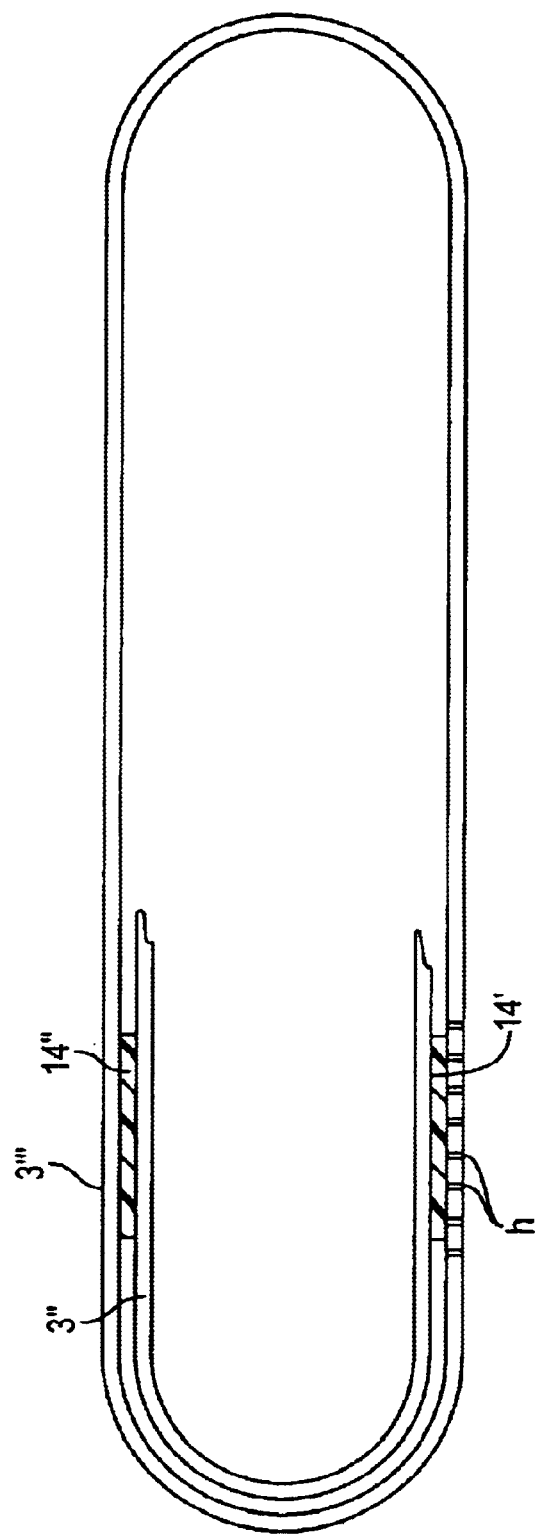

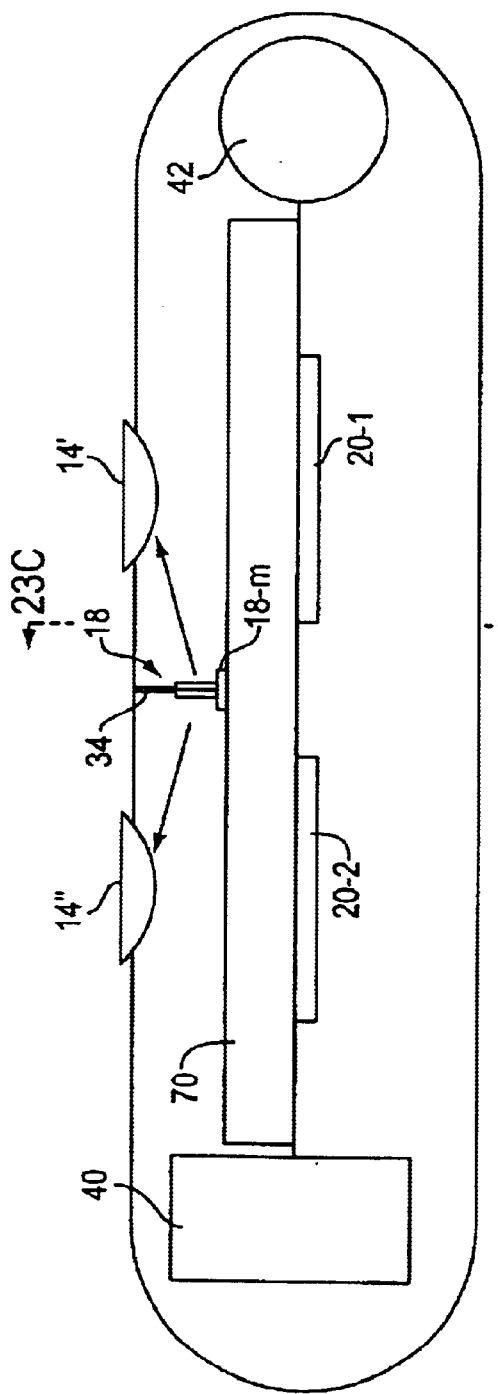
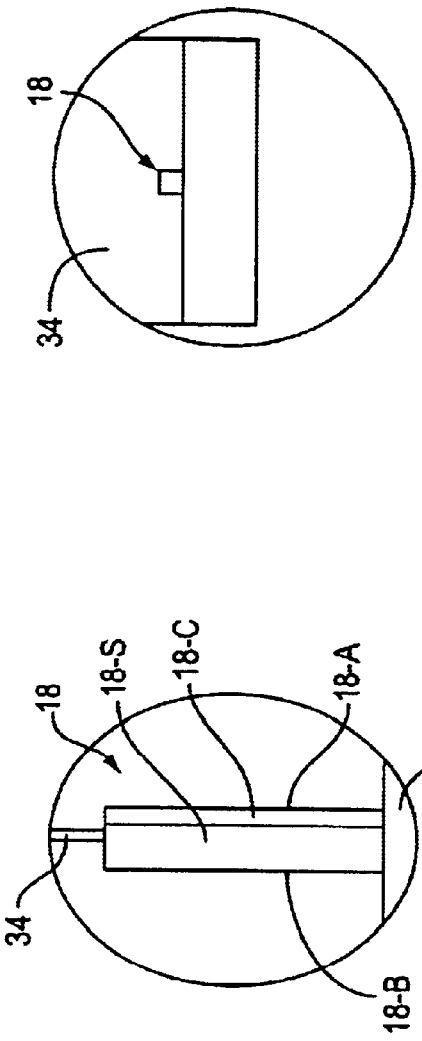
FIG. 23A
FIG. 23B
FIG. 23C

OPTICAL-BASED SENSING DEVICES

The present invention is a continuation-in-part of U.S. patent application Ser. No. 09/383,148, filed Aug. 26, 1999 is now U.S. Pat. No. 6,330,464 and of U.S. patent application Ser. No. 09/304,831, filed May 5, 1999 now abandoned and of U.S. patent application Ser. No. 09/140,747, filed on Aug. 26, 1998 now U.S. Pat. No. 6,304,766, the entire disclosures of which are incorporated herein by reference as if recited herein in full.

BACKGROUND OF THE INVENTION

1. Field of the Invention

The invention relates to electro-optical sensing devices for detecting the presence or concentration of an analyte in a liquid or gaseous medium. More particularly, the invention relates to (but is not in all cases necessarily limited to) optical-based sensing devices which are characterized by being totally self-contained, with a smooth and rounded oblong, oval, or elliptical shape (e.g., a bean- or pharmaceutical capsule-shape) and an extraordinarily compact size which permit the device to be implanted in humans for in-situ detection of various analytes.

2. Background Art

U.S. Pat. No. 5,517,313, the disclosure of which is incorporated herein by reference, describes a fluorescence-based sensing device comprising indicator molecules and a photosensitive element, e.g., a photodetector. Broadly speaking, in the context of the field of the present invention, indicator molecules are molecules one or more optical characteristics of which is or are affected by the local presence of an analyte. In the device according to U.S. Pat. No. 5,517,313, a light source, e.g., a light-emitting diode ("LED"), is located at least partially within a layer of material containing fluorescent indicator molecules or, alternatively, at least partially within a wave guide layer such that radiation (light) emitted by the source strikes and causes the indicator molecules to fluoresce. A high-pass filter allows fluorescent light emitted by the indicator molecules to reach the photosensitive element (photodetector) while filtering out scattered light from the light source.

The fluorescence of the indicator molecules employed in the device described in U.S. Pat. No. 5,517,313 is modulated, i.e., attenuated or enhanced, by the local presence of an analyte. For example, the orange-red fluorescence of the complex tris(4,7-diphenyl-1,10-phenanthroline) ruthenium(II) perchlorate is quenched by the local presence of oxygen. Therefore, this complex can be used advantageously as the indicator molecule in an oxygen sensor. Indicator molecules whose fluorescence properties are affected by various other analytes are known as well.

Furthermore, indicator molecules which absorb light, with the level of absorption being affected by the presence or concentration of an analyte, are also known. See, for example, U.S. Pat. No. 5,512,246, the disclosure of which is incorporated by reference, which discloses compositions whose spectral responses are attenuated by the local presence of polyhydroxyl compounds such as sugars. It is believed, however, that such light-absorbing indicator molecules have not been used before in a sensor construct like that taught in U.S. Pat. No. 5,517,313 or in a sensor construct as taught herein.

In the sensor described in U.S. Pat. No. 5,517,313, the material which contains the indicator molecules is permeable to the analyte. Thus, the analyte can diffuse into the material from the surrounding test medium, thereby affecting the fluorescence of the indicator molecules. The light source, indicator molecule-containing matrix material, high-pass filter, and photodetector are configured such that fluorescent light emitted by the indicator molecules impacts the photodetector such that an electrical signal is generated that is indicative of the concentration of the analyte in the surrounding medium.

The sensing device described in U.S. Pat. No. 5,517,313 represents a marked improvement over devices which constitute prior art with respect to U.S. Pat. No. 5,517,313. There has, however, remained a need for sensors that permit the detection of various analytes in an extremely important environment—the human body. Moreover, further refinements have been made in the field, which refinements have resulted in smaller and more efficient devices.

SUMMARY OF THE INVENTION

In general, a sensor according to one aspect of the invention is totally self-contained, with a source of radiation (e.g., an LED) and a photosensitive element (e.g., a photodetector) both completely embedded within a light-transmitting sensor body that functions as a wave guide. Indicator molecules are located on the outer surface of the sensor body, e.g., directly coated thereon or immobilized within a polymer matrix layer. When the radiation source emits radiation, a substantial portion of the radiation is reflected within the sensor body due to internal reflection from the interface of the sensor body and the surrounding medium (polymer matrix or medium in which the analyte is present). When the radiation impacts the interface of the sensor body and the surrounding medium, it interacts with the indicator molecules immobilized on the surface of the sensor body. Radiation emitted by the indicator molecules (i.e., fluorescent light in the case of fluorescent indicator molecules) or emitted by the source and not absorbed by the indicator molecules (e.g., in the case of light-absorbing indicator molecules) is reflected throughout the sensor body due to internal reflection. The internally reflected radiation strikes the photosensitive element such that a signal is generated that is indicative of the presence and/or concentration of the analyte.

A sensor according to this aspect of the invention is constructed with components that permit the source of radiation to be powered either by external means, e.g., an electromagnetic wave, ultrasound, or infrared light, or by wholly internal means, e.g., by using radioluminescence or components such as microbatteries, microgenerators, piezoelectrics, etc. The sensor also has components to transmit a signal indicative of the level of internally reflected light or other radiation, from which level of internally reflected radiation the analyte concentration is determined. Such components may be an inductor that is separate from a power-receiving inductor, or the same inductor might be used both to receive power-generating electromagnetic energy and to transmit information-bearing electromagnetic signal waves.

According to another aspect of the invention, a sensor is constructed to facilitate its use subcutaneously in a living human being. To that end, according to this aspect of the invention, a sensor is approximately the size and shape of a bean or pharmaceutical cold capsule. Furthermore, the sensor preferably is provided with a sensor/tissue interface layer which either prevents the formation of scar tissue or which overcomes the formation of scar tissue by promoting the ingrowth of analyte-carrying vascularization. The shape of a sensor according to this aspect of the invention has been found in and of itself to provide beneficial optical properties, and therefore such a sensor could be constructed for applications other than in the human body, i.e., without an interface layer and/or with electrical leads extending into and out of the sensor.

A sensor according to another aspect of the invention is constructed with light-absorbing (or other radiation-absorbing) indicator molecules which absorb the radiation generated by the source. The level of absorption varies as a function of the analyte concentration. By measuring the amount of internally reflected radiation, the analyte concentration can be determined.

A sensor according to another aspect of the invention capitalizes on the relationship between the density of a medium and its refractive index to measure analyte concentration. As analyte concentration varies, the density of the medium to which the sensor is exposed changes, and therefore the refractive index of the surrounding medium changes as well. As the refractive index of the surrounding medium changes, the amount of light that is reflected internally (or, conversely, which passes across the sensor/medium interface) also changes, and this change in illumination can be measured by a photosensitive element within the sensor and correlated with the locally surrounding analyte concentration.

According to a further aspect of the invention, a sensor is provided which includes: (a) at least one analyte sensing indicator channel that operates as described above; and (b) at least one additional channel that serves as an optical reference channel. The optical reference channel preferably: (a) measures one or more optical characteristic(s) of the indicator molecule (i.e., the indicator molecule of the analyte sensing indicator channel) which is unaffected or generally unaffected by the presence or concentration of the analyte; and/or (b) measures the optical characteristic of a second control indicator molecule which is unaffected or generally unaffected by the presence or concentration of the analyte. In the field of the present invention, indicator molecules that are unaffected or generally unaffected by the presence or concentration of analyte are broadly referred to herein as control indicator molecules.

The optical reference channel can be used, for example, to compensate or correct for: changes or drift in the component operation intrinsic to the sensor make-up; environment conditions external to the sensor; or combinations thereof. For example, the optical reference channel can be used to compensate or correct for internal variables induced by, among other things: aging of the sensor's radiation source; changes affecting the performance or sensitivity of the photosensitive element; deterioration of the indicator molecules; changes in the radiation transmissivity of the sensor body, of the indicator matrix layer, etc.; changes in other sensor components; etc. In other examples, the optical reference channel could also be used to compensate or correct for environmental factors (e.g., factors external to the sensor) which could affect the optical characteristics or apparent optical characteristics of the indicator molecule irrespective of the presence or concentration of the analyte. In this regard, exemplary external factors could include, among other things: the temperature level; the pH level; the ambient light present; the reflectivity or the turbidity of the medium that the sensor is applied in; etc.

The above and other aspects, features and advantages will be further appreciated based on the following description in conjunction with the attached drawings.

BRIEF DESCRIPTION OF THE DRAWINGS

These and other aspects of the invention will be apparent from the detailed description of the invention and the following figures, which are given by way of example and not limitation, and in which:

FIG. 14b is a side view of the sensor shown in FIG. 14a;

FIG. 15a is a top view of a sensor according to yet another embodiment of the invention incorporating a reference channel and an indicator channel;

FIG. 15b is a side view of the sensor shown in FIG. 15a.

FIG. 15c is a side view of modified sensor similar to that shown in FIG. 15a including a reference channel and an indicator channel;

FIG. 16a is a top view of a sensor according to yet another embodiment of the invention incorporating a reference channel and an indicator channel;

FIG. 16b is a side view of the sensor shown in FIG. 16a;

FIG. 17a is a side view of a sensor according to yet another embodiment of the invention incorporating a reference channel and an indicator channel in a sensor construction having an inner capsule and an outer sleeve;

FIG. 17b is a top view of the sensor shown in FIG. 17a;

FIG. 17c is a side view of a sensor according to yet another embodiment of the invention incorporating a reference channel and an indicator channel in a sensor construction having an inner capsule and an outer sleeve;

FIG. 17d is a top view of the sensor shown in FIG. 17c;

FIG. 17e is a side view of a sensor according to yet another embodiment of the invention incorporating a reference channel and an indicator channel in a sensor construction having an inner capsule and an outer sleeve;

FIG. 17f is a top view of the sensor shown in FIG. 17e;

FIG. 18a is a side view of a sensor according to an embodiment of the invention having an inner capsule and an outer sleeve without a reference channel;

FIG. 18b is a top view of the sensor shown in FIG. 18a;

FIGS. 20a–20b show a top view and a side view, respectively, of another embodiment of the invention including a removable film containing sensing membrane(s)

FIG. 22(A) is a top view of a sensor according to another embodiment of the invention having a shielding sleeve (with the shielding sleeve partially removed).

FIG. 22(B) is a cross-sectional side view of the sensor shown in FIG. 22(A).

FIG. 22(C) is an enlarged view of a portion of the illustration shown in FIG. 22(B).

FIG. 22(D) is a cross-sectional side view of a sensor according to another embodiment of the invention.

FIG. 23(A) is a cross-sectional side view of a sensor according to another embodiment of the invention having an LED radiation source which emits radiation in two directions.

FIG. 23(B) is an enlarged view of a portion of the illustration shown in FIG. 23(A).

FIG. 23(C) is a cross-sectional side view take along the arrows 23(C)—23(C) in FIG. 23(A).

DETAILED DESCRIPTION OF THE INVENTION

Initial Optical-Based Sensor Embodiments

Figure 1:
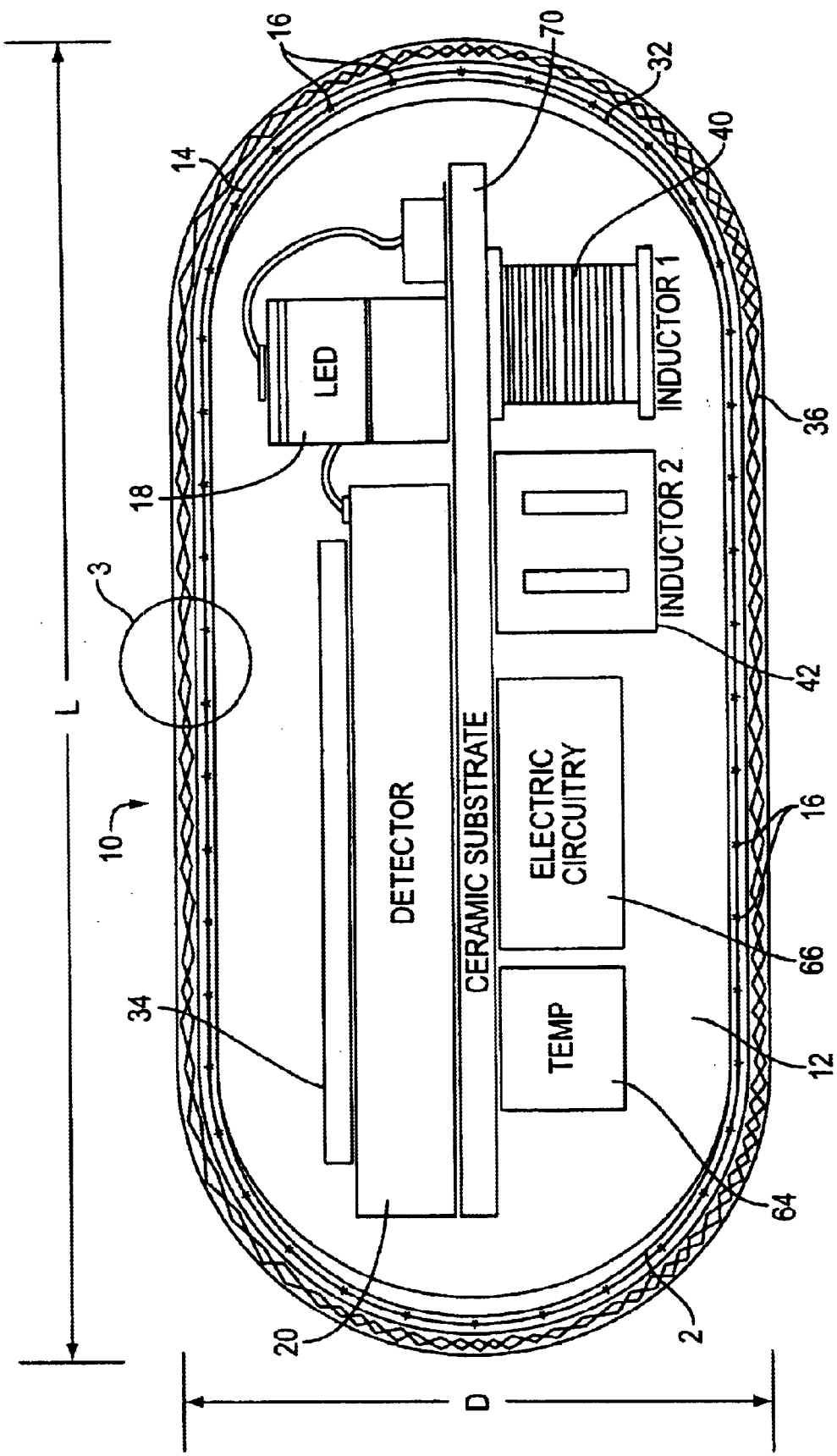
FIG. 1 is a schematic, section view of a fluorescence-based sensor according to the invention.

An optical-based sensor ("sensor") 10 according to one aspect of the invention, which operates based on the fluorescence of fluorescent indicator molecules, is shown in FIG. 1. The sensor 10 has as its primary components a sensor body 12; a matrix layer 14 coated over the exterior surface of the sensor body 12, with fluorescent indicator molecules 16 distributed throughout the layer; a radiation source 18, e.g. an LED, that emits radiation, including radiation over a range of wavelengths which interact with the indicator molecules (referred to herein simply as "radiation at a wavelength which interacts with the indicator molecules"), i.e., in the case of a fluorescence-based sensor, a wavelength which causes the indicator molecules 16 to fluoresce; and a photosensitive element 20, e.g. a photodetector, which, in the case of a fluorescence-based sensor, is sensitive to fluorescent light emitted by the indicator molecules 16 such that a signal is generated in response thereto that is indicative of the level of fluorescence of the indicator molecules. In the simplest embodiments, indicator molecules 16 could simply be coated on the surface of the sensor body. In preferred embodiments, however, the indicator molecules are contained within the matrix layer 14, which comprises a biocompatible polymer matrix that is prepared according to methods known in the art and coated on the surface of the sensor body as explained below. Suitable biocompatible matrix materials, which must be permeable to the analyte, include methacrylates and hydrogels which, advantageously, can be made selectively permeable—particularly to the analyte—i.e., they perform a molecular weight cut-off function.

Figure 2:
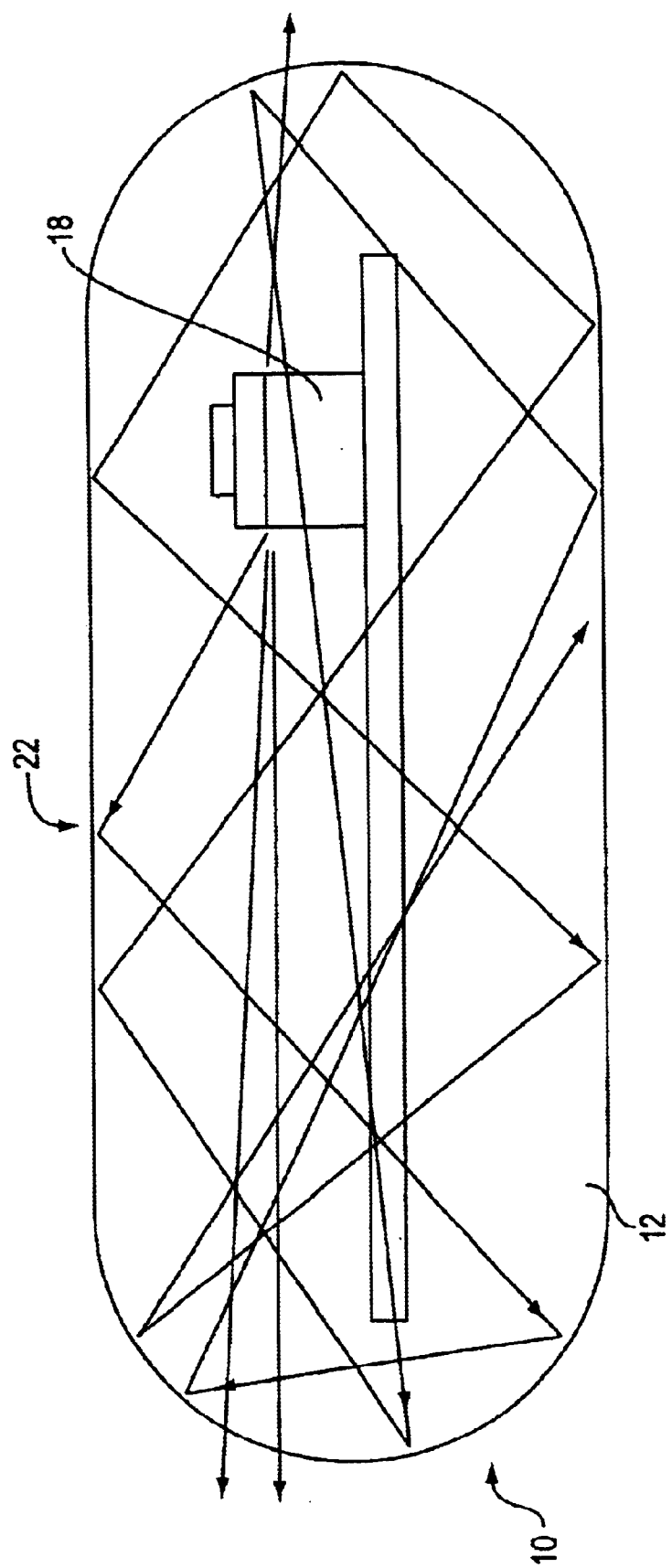
FIG. 2 is a schematic diagram of the fluorescence-based sensor shown in FIG. 1 illustrating the wave guide properties of the sensor.

The sensor 12 advantageously is formed from a suitable, optically transmissive polymer material which has a refractive index sufficiently different from that of the medium in which the sensor will be used such that the polymer will act as an optical wave guide. Preferred materials are acrylic polymers such as polymethylmethacrylate, polyhydroxypropylmethacrylate and the like, and polycarbonates such as those sold under the trademark Lexan®. The material allows radiation employed by the device—radiation generated by the radiation source 18 (e.g., light at an appropriate wavelength in embodiments in which the radiation source is an LED) and, in the case of a fluorescence-based embodiment, fluorescent light emitted by the indicator molecules—to travel through it. As shown in FIG. 2, radiation (e.g., light) is emitted by the radiation source 18 and (at least some) is reflected internally at the surface of the sensor body 12, e.g., as at location 22, thereby "bouncing" back-and-forth throughout the interior of the sensor body 12.

It has been found that light reflected from the interface of the sensor body and the surrounding medium is capable of interacting with indicator molecules coated on the surface (whether coated directly thereon or contained within a matrix), e.g., exciting fluorescence in fluorescent indicator molecules coated on the surface. In addition, light which strikes the interface at angles, measured relative to a normal to the interface, too small to be reflected passes through the interface and also excites fluorescence in fluorescent indicator molecules. Other modes of interaction between the light (or other radiation) and the interface and the indicator molecules have also been found to be useful depending on the construction of and application for the sensor. Such other modes include evanescent excitation and surface plasmon resonance type excitation.

Figure 3:
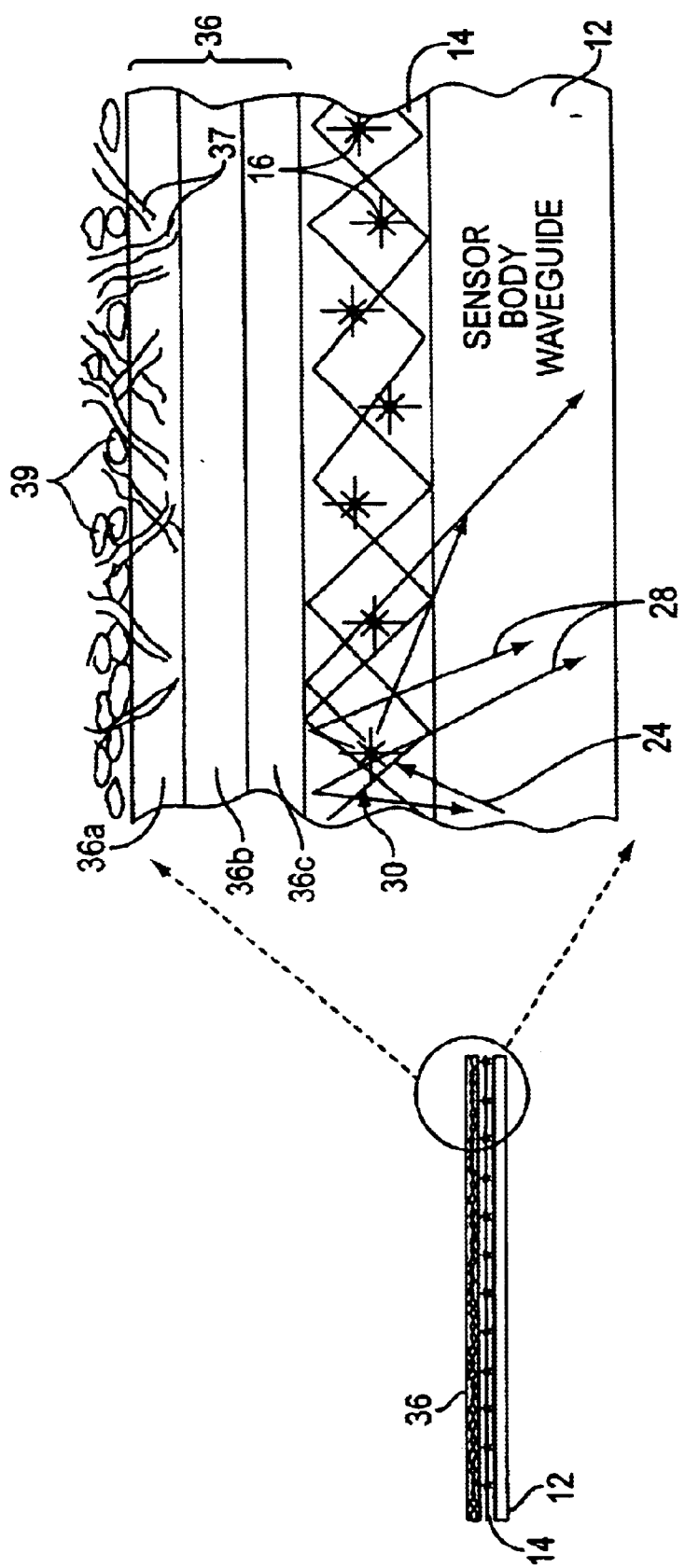
FIG. 3 is a detail view of the circled portion of FIG. 1 demonstrating internal reflection within the body of the sensor and a preferred construction of the sensor/tissue interface layer.
Figure 4:
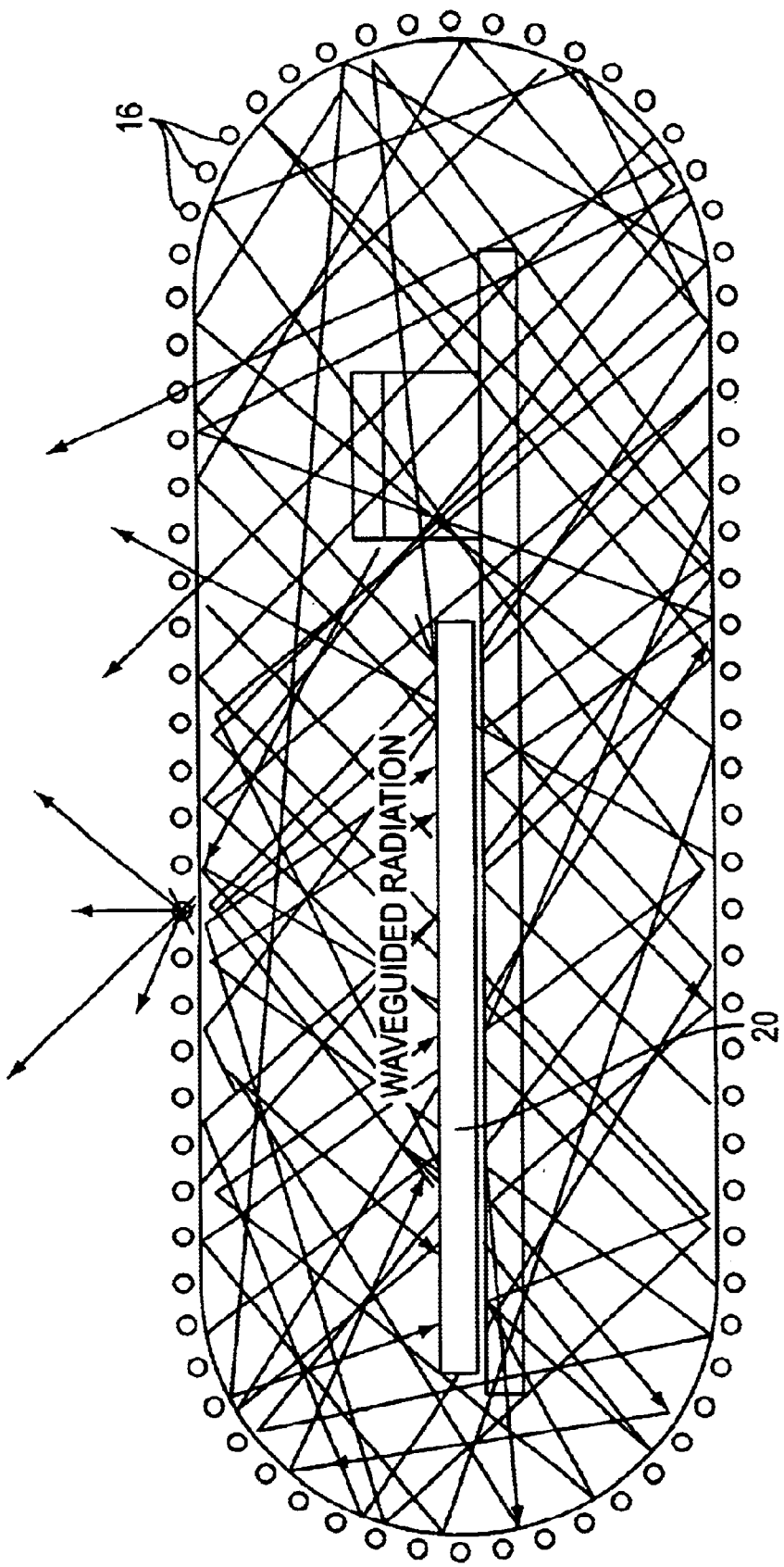
FIG. 4 is schematic diagram, similar to FIG. 2, illustrating reflection within the sensor body by radiation generated by an internal radiation source and by fluorescent light emitted by external indicator molecules.

As demonstrated by FIGS. 3 and 4, at least some of the light emitted by the fluorescent indicator molecules 16 enters the sensor body 12, either directly or after being reflected by the outermost surface (with respect to the sensor body 12) of the matrix layer 14, as illustrated in region 30. Such fluorescent light 28 is then reflected internally throughout the sensor body 12, much like the radiation emitted by the radiation source 18 is, and, like the radiation emitted by the radiation source, some will strike the interface between the sensor body and the surrounding medium at angles too small to be reflected and will pass back out of the sensor body. Internal reflection of radiation emitted by the source 18 and, for fluorescence-based sensors, fluorescent light emitted by the fluorescent indicator molecules 16, illustrated schematically in FIG. 4, impinges on the photosensitive element 20, which senses the level of such internal illumination.

As further illustrated in FIG. 1, the sensor 10 may also include reflective coatings 32 formed on the ends of the sensor body 12, between the exterior surface of the sensor body and the matrix layer 14, to maximize or enhance the internal reflection of the radiation and/or light emitted by fluorescent indicator molecules. The reflective coatings may be formed, for example, from paint or from a metallized material provided such metallized material does not impede transmission of telemetry signals to and from the sensor, described below).

As still further illustrated in FIG. 1, an optical filter 34 preferably is provided on the light-sensitive surface of the photosensitive element (photodetector) 20. This filter, as is known from the prior art, prevents or substantially reduces the amount of radiation generated by the source 18 from impinging on the photosensitive surface of the photosensitive element 20. At the same time, the filter allows fluorescent light emitted by fluorescent indicator molecules to pass through it to strike the photosensitive region of the detector. This significantly reduces "noise" in the photodetector signal that is attributable to incident radiation from the source 18.

The application for which the sensor 10 according to one aspect of the invention was developed in particular—although by no means the only application for which it is suitable—is measuring various biological analytes in the human body, e.g., glucose, oxygen, toxins, pharmaceuticals or other drugs, hormones, and other metabolic analytes. The specific composition of the matrix layer 14 and the indicator molecules 16 may vary depending on the particular analyte the sensor is to be used to detect and/or where the sensor is to be used to detect the analyte (i.e., in the blood or in subcutaneous tissues). Two constant requirements, however, are that the matrix layer 14 facilitate exposure of the indicator molecules to the analyte and that the optical characteristics of the indicator molecules (e.g., the level of fluorescence of fluorescent indicator molecules) are a function of the concentration of the specific analyte to which the indicator molecules are exposed.

To facilitate use in-situ in the human body, the sensor 10 is formed in a smooth, oblong or rounded shape. Advantageously, it has the approximate size and shape of a bean or a pharmaceutical gelatin capsule, i.e., it is on the order of approximately 500 microns to approximately 0.5 inch in length L and on the order of approximately 300 microns to approximately 0.3 inch in diameter D, with generally smooth, rounded surfaces throughout. This configuration permits the sensor 10 to be implanted into the human body, i.e., dermally or into underlying tissues (including into organs or blood vessels) without the sensor interfering with essential bodily functions or causing excessive pain or discomfort.

Moreover, it will be appreciated that any implant placed within the human (or any other animal's) body—even an implant that is comprised of "biocompatible" materials—will cause, to some extent, a "foreign body response" within the organism into which the implant is inserted, simply by virtue of the fact that the implant presents a stimulus. In the case of a sensor 10 that is implanted within the human body, the "foreign body response" is most often fibrotic encapsulation, i.e., the formation of scar tissue. Glucose—a primary analyte which sensors according to the invention are expected to be used to detect—may have its rate of diffusion or transport hindered by such fibrotic encapsulation. Even molecular oxygen ($O_2$) which is very small, may have its rate of diffusion or transport hindered by such fibrotic encapsulation as well. This is simply because the cells forming the fibrotic encapsulation (scar tissue) can be quite dense in nature or have metabolic characteristics different from that of normal tissue.

To overcome this potential hindrance to or delay in exposing the indicator molecules to biological analytes, two primary approaches are contemplated. According to one approach, which is perhaps the simplest approach, a sensor/tissue interface layer—overlying the surface of the sensor body 12 and/or the indicator molecules themselves when the indicator molecules are immobilized directly on the surface of the sensor body, or overlying the surface of the matrix layer 14 when the indicator molecules are contained therein—is prepared from a material which causes little or acceptable levels of fibrotic encapsulation to form. Two examples of such materials described in the literature as having this characteristic are Preclude™ Periocardial Membrane, available from W. L. Gore, and polyisobutylene covalently combined with hydrophiles as described in Kennedy, "Tailoring Polymers for Biological Uses," *Chemtech*, February 1994, pp. 24–31.

Alternatively, a sensor/tissue interface layer that is composed of several layers of specialized biocompatible materials can be provided over the sensor. As shown in FIG. 3, for example, the sensor/tissue interface layer 36 may include three sublayers 36a, 36b, and 36c. The sublayer 36a, a layer which promotes tissue ingrowth, preferably is made from a biocompatible material that permits the penetration of capillaries 37 into it, even as fibrotic cells 39 (scar tissue) accumulate on it. Gore-Tex® Vascular Graft material (ePTFE), Dacron® (PET) Vascular Graft materials which have been in use for many years, and MEDPOR Biomaterial produced from high-density polyethylene (available from POREX Surgical Inc.) are examples of materials whose basic composition, pore size, and pore architecture promote tissue and vascular ingrowth into the tissue ingrowth layer.

The sublayer 36b, on the other hand, preferably is a biocompatible layer with a pore size (less than 5 micrometers) that is significantly smaller than the pore size of the tissue ingrowth sublayer 36a so as to prevent tissue ingrowth. A presently preferred material from which the sublayer 36b is to be made is the Preclude Periocardial Membrane (formerly called GORE-TEX Surgical Membrane), available from W. L. Gore, Inc., which consists of expanded polytetra-fluoroethylene (ePTFE).

The third sublayer 36c acts as a molecular sieve, i.e., it provides a molecular weight cut-off function, excluding molecules such as immunoglobulins, proteins, and glycoproteins while allowing the analyte or analytes of interest to pass through it to the indicator molecules (either coated directly on the sensor body 12 or immobilized within a matrix layer 14). Many well known cellulose-type membranes, e.g., of the sort used in kidney dialysis filtration cartridges, may be used for the molecular weight cut-off layer 36c.

Although the sensor/tissue interface layer 36 is described and shown in FIG. 3 as including a third, molecular weight cut-off layer 36c, it will be appreciated that it is possible to select a polymer from which to make the matrix layer 14, e.g., a methacrylate or a hydrated hydrophilic acrylic, such that it performs the molecular weight cut-off function without the need for a separate sublayer 36c. It is recommended, however, that the two sublayers 36a and 36b be used, with the outer layer 36a promoting tissue ingrowth and the inner layer 36b preventing tissue ingrowth, because the inner layer 36b functions as an additional barrier (or "prefilter") between the outer layer 36a and the molecular weight cut-off layer (whether provided separately or by the matrix layer 14 itself). This reduces the likelihood of the molecular weight cut-off layer becoming clogged or fouled by macromolecules such as immunoglobulins, extracellular matrix proteins, lipids, and the like, and thereby maximizes the speed and efficiency with which the analyte or analytes of interest come into contact with the indicator molecules. (In order for a sensor to be useful for in vivo testing, the analyte exposure lag time, i.e., the amount of time it takes for the concentration of analyte to which the indicator molecules are directly exposed to come to a steady state, must be relatively short, i.e., on the order of two to five minutes.) Various combinations and permutations of biocompatible materials from which to construct the sensor/tissue interface layer will be apparent to those having skill in the medical implant art.

Finally, with respect to the sensor/tissue interface layer, in addition to preventing adverse reactions, it is believed that the interface layer enhances reflection of light (whether from fluorescent indicator molecules or from the radiation source 18) from the outermost surface of the matrix layer 14 and into the sensor body 12.

A further aspect of a sensor according to the invention is that it may be wholly self-contained. In other words, in specific embodiments, the sensor may be constructed in such a way that no electrical leads extend into or out of the sensor body to supply power to the sensor (e.g., for driving the source 18) or to transmit signals from the sensor. Rather, a sensor according to this aspect of the invention may include a power source 40 (FIG. 1) that is wholly embedded or encapsulated within the sensor body 12 and a transmitter 42 (FIG. 1) that also is entirely embedded or encapsulated within the sensor body 12.

(The shape of the sensor 10 has been found in and of itself to provide superior optical properties, however. Accordingly, embodiments of the sensor having power and/or signal-transmitting leads extending into and/or out of the sensor body are also within the scope of the invention.)

Figure 5:
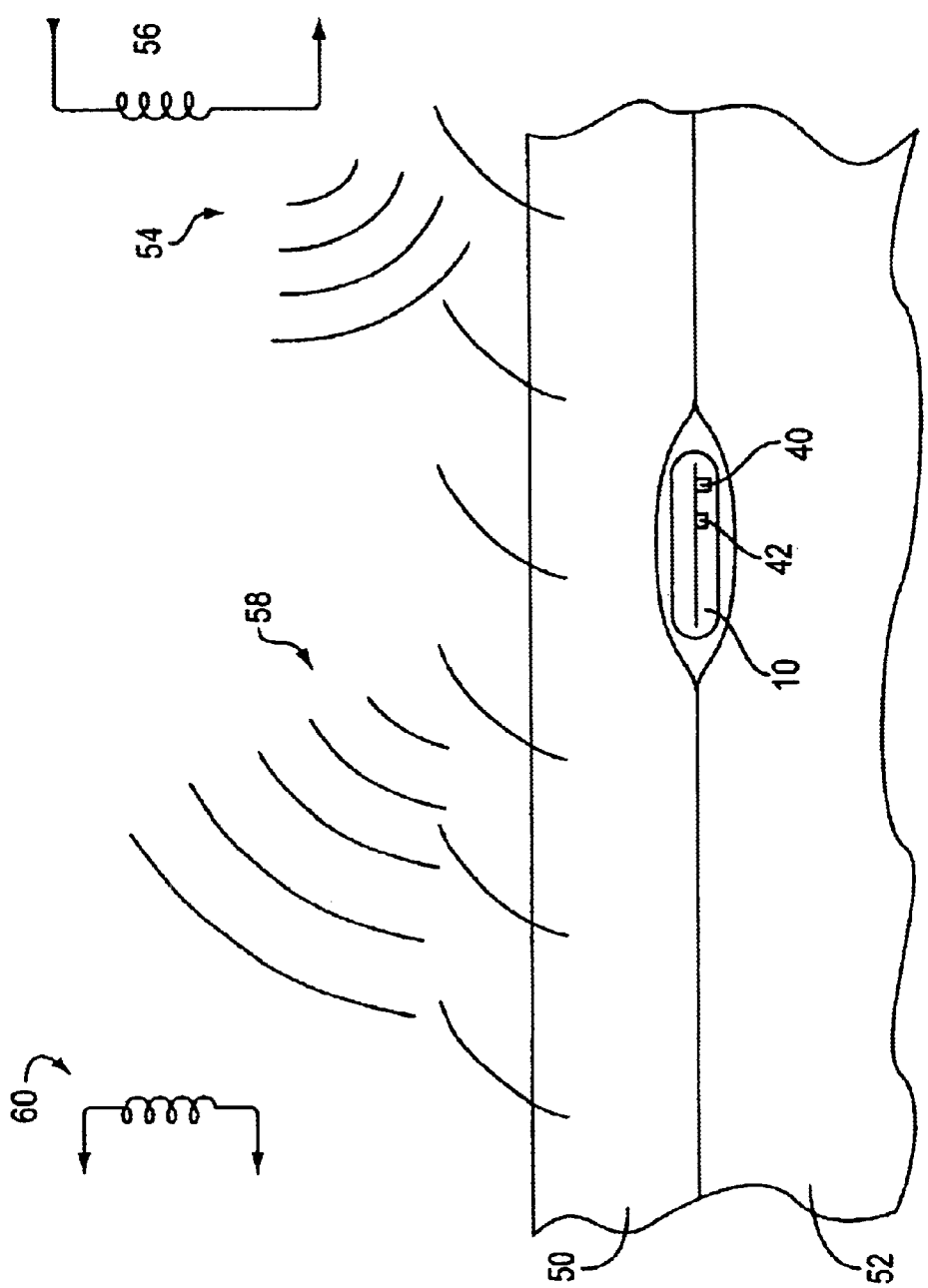
FIG. 5 is a schematic diagram demonstrating use of a sensor according to the invention in a human being.

In a preferred embodiment, the power source 40 is an inductor, as is the transmitter 42. Thus, when the sensor is implanted in the body, e.g. between the skin 50 and subcutaneous tissues 52 as shown in FIG. 5, the sensor can be powered—i.e., the radiation source can be caused to emit radiation which interacts with the indicator molecules 16—by exposing the sensor to a field of electromagnetic radiation 54 created, for example, by an inductor coil 56 that is housed in an appropriately configured instrument (not shown) positioned near the sensor. Similarly, the transmitter 42, as an inductor, generates an electromagnetic field 58 that is indicative of the level of light striking the photosensitive element and hence the presence or concentration of analyte. The field 58 constitutes a signal that can be detected by an external receiver 60. The signal may be, for example, a 50 megahertz carrier, amplitude modulated signal; a frequency modulated signal; a digital signal; or any other type of electromagnetic wave signal that would be known to one having skill in the art.

Alternatively, it is possible to use a single coil and a single inductor for all telemetry. In such an embodiment, the coil 56 generates the electromagnetic wave 54 at one frequency to induce a current in the inductor 40, which powers the source of radiation 18; the amount of internally reflected light sensed by the photosensitive element 20 is transmitted by the same inductor 40 as a modulated electromagnetic wave which induces a current in coil 56. This modulated wave is generated by modulating the current flowing through inductor 40 by the photosensitive element 20 as a function of detected light and is detected by measuring the resulting induced current in coil 56.

Alternatively, the system could be configured to switch (in rapid sequence) between a power generating mode and a signal transmitting mode. These and other telemetry schemes will be familiar to those having skill in the art, as such techniques are used relatively commonly, e.g., in connection with "smart cards" having an implanted integrated circuit chip which can be waved past a sensor to gain access to a building, sometimes referred to as radio frequency identification.

Other contemplated self-contained power sources for driving the radiation source 18 include microbatteries; piezoelectrics (which generate a voltage when exposed to mechanical energy such as ultrasonic sound; micro generators; acoustically (e.g., ultrasound) driven generators; and photovoltaic cells, which can be powered by light (infrared) passing through the skin 50.

Figure 6:
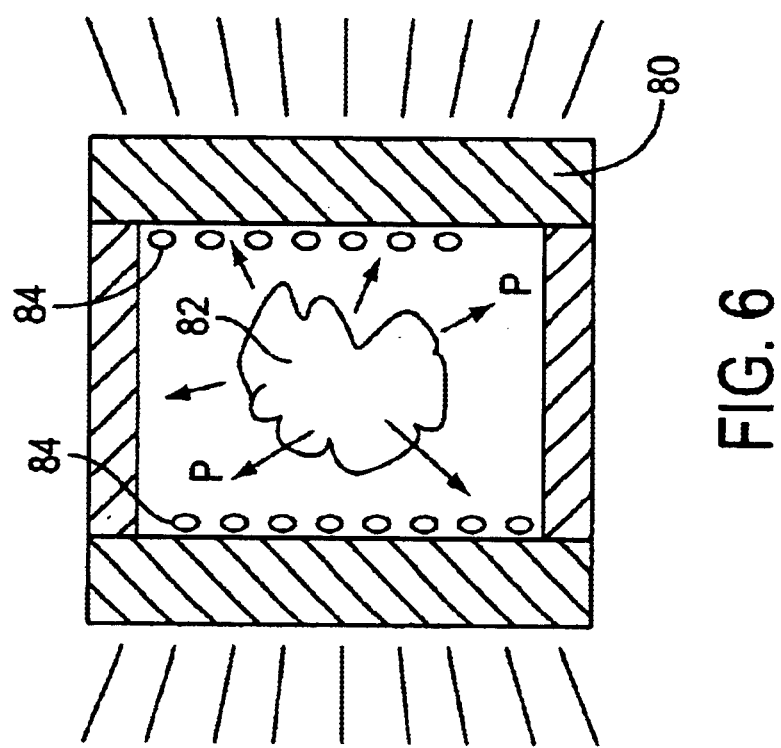
FIG. 6 is a schematic section view of a radioluminescent light source.

As yet another alternative, in place of an LED, a radioluminescent light source can be used. As illustrated in FIG. 6, such a radioluminescent light source includes a sealed, optically transmissive vessel 80 (e.g., cylindrical, spherical, or cubic) with a sample of radioisotope 82, e.g. tritium, contained therein. The radioisotope emits beta particles which strike intermediate luminophore molecules 84 coated on the interior surface of the vessel 80, thereby causing the intermediate luminophore molecules to emit light. Although the beta particles are too weak to pass through the walls of the vessel, the light emitted by the intermediate luminophore molecules does pass through, thereby illuminating the sensor with light—similarly to an LED—that interacts with the indicator molecules. Such radioluminescent generation of light, and similar generation of light, is known in the art. See, for example, U.S. Pat. No. 4,677,008, the disclosure of which is incorporated by reference, and Chuang and Arnold, "Radioluminescent Light Source for Optical Oxygen Sensors," 69 Analytical Chemistry No. 10, 1899–1903, May 15, 1997, the disclosure of which also is incorporated by reference. As another alternative to an LED, the sensor might employ an electroluminscent lamp such as that shown in U.S. Pat. No. 5,281,825.

With respect to the other components shown in FIG. 1, a temperature sensor 64 and an optional signal amplifier 66 are also advantageously provided. The temperature sensor 64 measures the locally surrounding temperature of the ambient tissues and the indicator molecule environment and provides this information to the control logic circuit (not shown). The control logic circuit correlates fluorescence level, for example, with analyte concentration level, thereby correcting the output signal for variations affected by temperature. Amplifier 66 is a relatively simple gain circuit which amplifies the signal generated by the photodetector 20.

To make a sensor according to the invention, the various components and circuitry of the sensor are assembled onto a precut, 0.2 inch by 0.4 inch ceramic (e.g., alumina) substrate 70. The substrate thickness is 0.020 inch. All circuit elements are standard surface mount components available, e.g., from Digi-Key, Garrett, and others. The components are attached to the substrate using standard silver conductive epoxy such as Ablebond-84, available from Ablebond.

Next, a high pass filter may be installed on the photosensitive element by applying a two-part high pass filter epoxy, commonly available from CVI Laser and others. Thickness of the filter is controlled by precision dispensing using a Rainin Micropipettor. The high pass filter epoxy is cured in an oven at 125° C. for two hours, as per the manufacturer's instructions. Similarly, if desired, a low pass filter may be coated over the radiation source (LED) by the same method using a commercially available low pass epoxy formulation. Custom formulations of optical filters can be prepared by adding a dye of the desired absorption spectra into Epotek epoxies. The appropriate concentration of the dopant can be determined by monitoring wavelength versus transmittance on a UV-Vis scan from a spectrophotometer until the desired spectral properties are obtained. Such custom-formulated epoxies can be cured similarly. Prefabricated glass, polymer, or coated filters may also be used and simply glued to the photosensitive element or devices using an optically matching adhesive, as is typical.

The circuit board with optical filters (if installed and cured) is then encapsulated using, e.g., a Lilly No. 4 two-part gelatin capsule as a mold. Other gelatin capsules work as well. The long "half" of an empty capsule is placed upright into a rack. Several drops of optically clear potting of the appropriate sensor body material, as described above, are added to fill the capsule to approximately one half of its volume. The substrate with pre-assembled circuitry is inserted end-on into the capsule and into the optical potting, which wicks around and into the small spaces of the circuit board assembly to help exclude air and thus prevent bubbles from subsequently forming in the finished sensor device. Additional optical potting is added using a micropipettor until the level reaches the top of the capsule with the capsule standing upright. The partial assembly is then further degassed by placing the capsule (supported by the rack) under a bell jar vacuum and allowing it to stand under vacuum until any bubbles observed within the capsule have escaped. The assembly is removed from the vacuum and "topped off" with additional optical potting, allowing surface tension to fill the gelatin capsule-half above its rim and to create a rounded, hemispherical dome shape that is similar to the opposite end.

The capsule is then placed under UV light and cured for several hours, with the curing time depending on the intensity of the UV source available. Heat cure and catalyst cure may alternatively be used, depending on the potting material. A full strength cure is obtained by subsequently incubating the post-UV-cure assembly at 60° C. for 12 hours, or otherwise as per the manufacturer's instructions.

The gelatin mold is then removed from the sensor body by soaking the encapsulated assembly in water for several hours to dissolve the gelatin. Several water changes and washes over the course of the time period help to remove all of the gelatin from the surface. The capsule is then air dried (or oven dried at 60° C.) in preparation for coating.

Once the sensor body is completely dried, it is coated with indicator molecules. The indicator molecules may be immobilized directly on the surface of the sensor body using techniques known in the art, or they may be contained within a matrix layer solution that is coated onto the central body. (A matrix layer solution containing fluorescent indicator molecules may be prepared according to methods known in the art; a matrix layer solution containing light-absorbing indicator molecules may be prepared as described below.) A convenient method for coating the sensor with a matrix layer is to affix a small (e.g., 32 gauge) wire to one end of the encapsulated circuitry to produce a hanger. This can be done using the same UV-cured optical potting material. Approximately one to two microliters of optical potting is placed on the end of the handle wire. The encapsulated circuit is placed in front of a UV lamp with the UV lamp turned off. The wire with optical potting on the tip is touched to the end of the capsule and the lamp is turned on. The small amount of optical potting "adhesive" will be cured immediately, thereby attaching the wire tip to the capsule. The capsule may now be dipped conveniently into matrix layer solutions (and separate indicator molecule solutions, as appropriate) and hung by the wire to cure. The wire may be removed simply by pulling it after the sensor is completely assembled.

Once the indicator molecules are securely bonded to the surface of the sensor body, whether directly thereon or in a matrix layer, the sensor/tissue interface layer is constructed by inserting the sensor body into a preformed tubular sleeve of the material and sealing each end using heat or epoxy or, if the desired sensor/tissue interface layer material is in sheet form, by rolling the sensor body longitudinally in the material and sealing the longitudinal seam and end seams using heat or epoxy.

Although the embodiment of a sensor 10 according to the invention shown and described so far has a single radiation source 18 (LED) and photosensitive element 20

(photodetector), thereby permitting detection of a single analyte, other configurations and components are possible. For example, two or more different types of indicator molecules may be provided to sense the presence or concentration of two or more analytes, respectively, with two or more photosensitive elements being provided on the ceramic substrate 70, each with its own respective transmitter 42. Each photosensitive element would have its own filter 34 designed to allow light from the respective indicator molecules to pass through to it. Similarly, a "two-channel" embodiment could be developed to measure analyte concentration by two different sensing schemes. In one such embodiment, for example, some of the indicator molecules would be fluorescent indicator molecules and the rest of the indicator molecules would be radiation-absorbing indicator molecules (as described below). Two separate photosensitive elements would be provided, each with its own appropriate filter—one to measure fluorescent light emitted by the fluorescent indicator molecules and one to measure radiation generated by the source and reflected throughout the sensor, with some absorption by the radiation-absorbing indicator molecules. Additionally, other types of photosensitive elements may be used, e.g., photoresistors, phototransistors, photodiodes, photodarlingtons, photovoltaic cells, positive insulating negative photodiodes, large-area photodiodes, avalanche photodiodes, charge coupled devices, etc.

Moreover, although a sensor according to the invention has been described above primarily as functioning based on fluorescence of indicator molecules, the invention is not so limited. According to another aspect of the invention, a sensor construct as per the invention may operate based on the light-absorbing characteristics of light-absorbing indicator molecules. A sensor according to this aspect of the invention could use a sensor construct like that shown in U.S. Pat. No. 5,517,313, referenced above; more preferably, it uses a bean- or pharmaceutical gelatin capsule construct as described above.

Figure 7B:
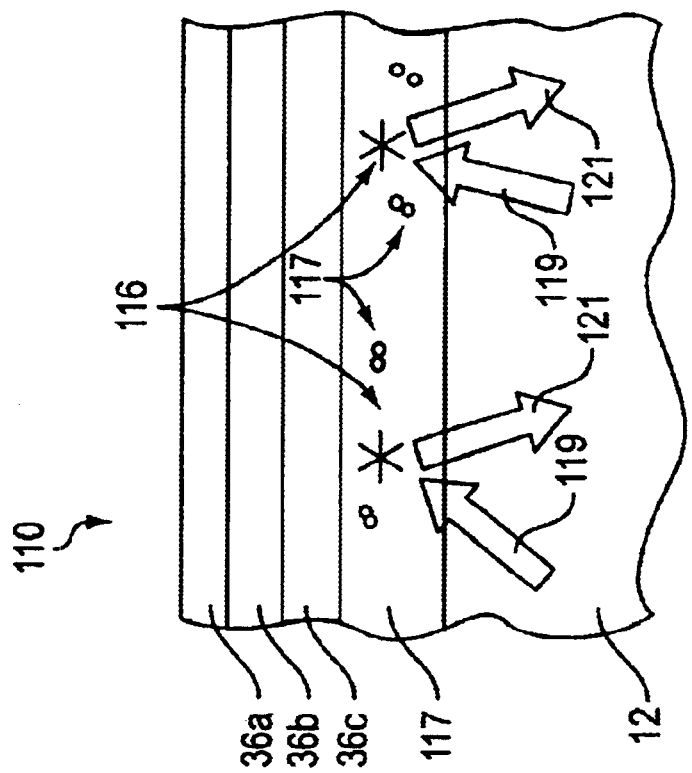
FIGS. 7a and 7b are schematic illustrations demonstrating the operation of a light-absorbing indicator molecule-based sensor according to another aspect of the invention.
Figure 7A:
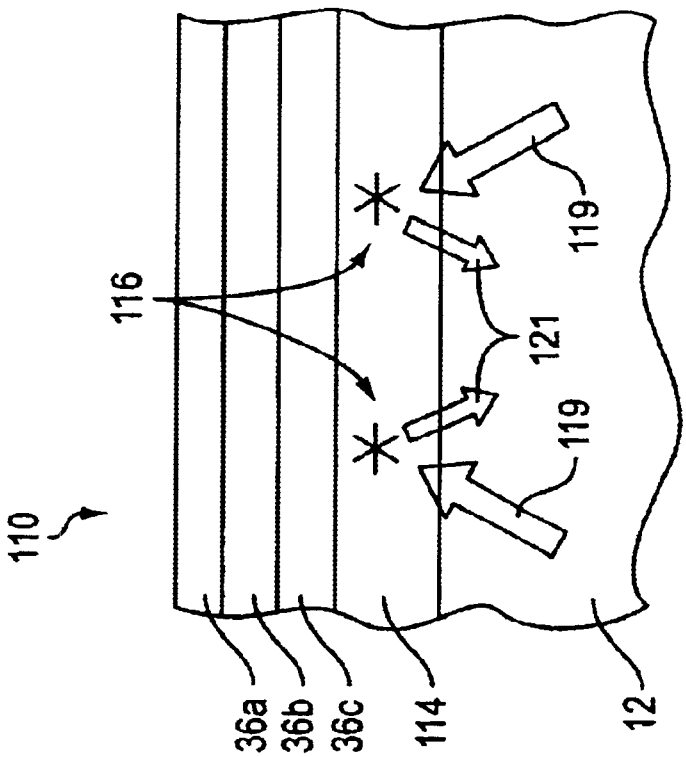

As illustrated in FIGS. 7a and 7b, when a sensor 110 according to this aspect of the invention is not exposed to any analyte, the light-absorbing indicator molecules 116 (which preferably are immobilized in a matrix layer 114) absorb a certain amount of radiation (light) 119 generated by the radiation source, falling within a particular range of wavelengths and passing out of the sensor body, and non-absorbed radiation 121 is reflected back into the sensor body. When the sensor 110 is exposed to analyte such that the light-absorbing indicator molecules 116 are exposed to analyte molecules 117, the light-absorbing properties of the indicator molecules are affected. For example, as shown in FIG. 7b, the light-absorbing capacity of the indicator molecules 116 may decrease such that the intensity of the light 121 reflected back into the sensor body 12 increases. The level of light within the sensor body is measured by a photosensitive element (not shown), as described above.

It will be appreciated that a light-absorbing indicator molecule-based sensor must be calibrated by determining the illumination intensity levels for various known concentrations of various analytes of interest. Furthermore, because the radiation (light) being measured is the radiation being emitted by the source itself, it will be further appreciated that if the radiation source has a very broad emission profile and the light-absorbing indicator molecule has a very narrow range of absorption wavelengths, a high-pass, low-pass, or band-pass filter may be provided over the photosensitive element so as to permit only this range of radiation wavelengths to be sensed by the photosensitive element.

Indicator molecules whose light-absorbing properties are affected by various analytes are known in the art. (As noted above, however, it is believed that such light-absorbing indicator molecules have not been used in connection with a sensor construct either like that taught herein or in U.S. Pat. No. 5,517,313.) For example, U.S. Pat. No. 5,512,246 discloses light-absorbing indicator molecules whose ability to absorb light varies as a function of the local concentration of glucose. In particular, as the local concentration of glucose increases, the ability of the indicator molecules to absorb light at a wavelength of 515 nanometers decreases. Therefore, if such indicator molecules are used in connection with a bean- or cold capsule-shaped sensor construct as disclosed herein, the level of internal illumination by light at that wavelength will increase. The local glucose concentration level can then be determined from the level of illumination at that wavelength.

Light-absorbing indicator molecules which are responsive to other analytes are well known in the art, e.g., as exemplified by phenolphthalein, which changes color in response to a change in pH.

As is the case with a fluorescent indicator molecule-based sensor, a sensor which utilizes light-absorbing indicator molecules could have the indicator molecules disposed directly on the surface of the sensor body. It is preferred, however, that the indicator molecules be immobilized within a matrix layer 114, as is shown in FIGS. 7a and 7b.

The matrix layer 114 may be manufactured by the low density polymerization of various organic monomers, including hydroxethylmethacrylate (HEMA). HEMA is widely available from sources such as PolySciences in Warrington, Pa. and Sigma in St. Louis, Mo., and may be polymerized by means of heating or exposing the monomers to ultraviolet light, as widely known and understood in the art.

In a preferred embodiment, the light-absorbing indicator molecules 116 are immobilized within the matrix layer 114 by reacting the HEMA with a doped monomer, e.g., aminoethylmethacrylate (AEMA). During polymerization, AEMA introduces a pendant amine group into the matrix layer 114. Monomers other than AEMA also may be used during the manufacture of the matrix layer 114, including aminopropylmethacrylate (APMA) and other commercially available monomers having different pendant groups and varying carbon chain lengths between the amino group and the rest of the monomer. In addition to monomers containing primary amine groups (e.g., AEMA), monomers containing secondary amine groups also may be used for forming the matrix layer 114. Alternatively, pendant cross-linker groups other than amine groups also may be used to covalently link the indicator molecules 116 to the polymer material of the matrix layer 114. Examples of alternative pendant cross-linker groups include sulfhydryl (—SH), carboxyl (COOH), aldehyde (COH), hydroxyl (OH), cyano (CN), ether, and epoxyl groups.

Figure 8:
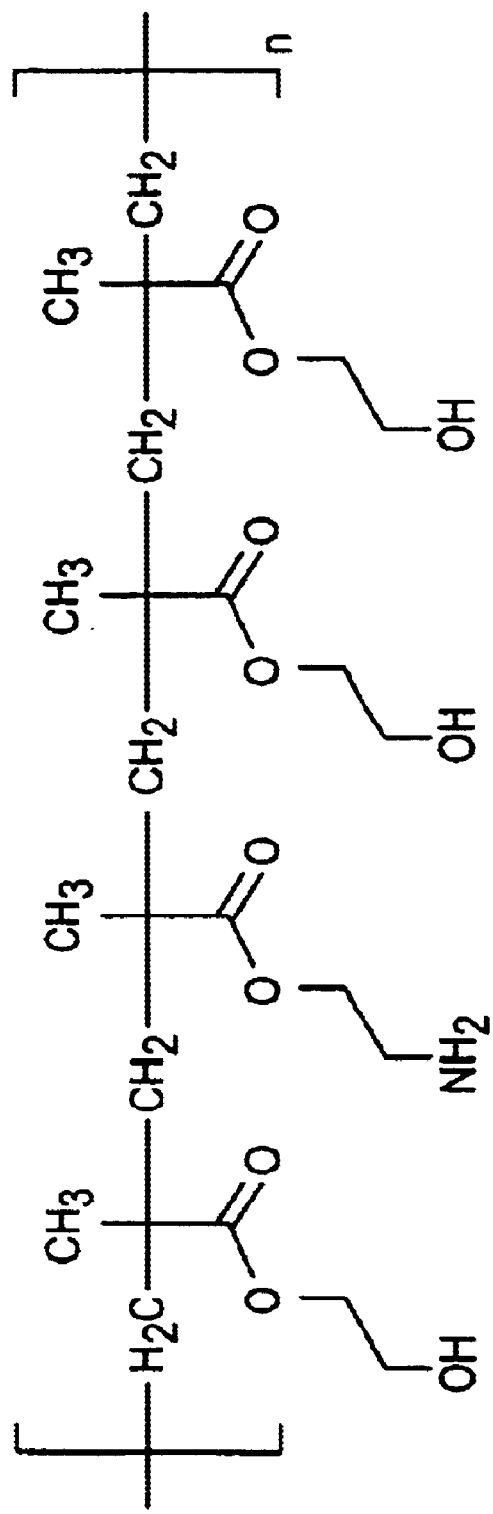
FIG. 8 is a formula for an embodiment of the matrix layer, wherein the polymerized macromolecule of the matrix layer contains a pendant amino group on about every one of four monomers.

Although a range of doping ratios may be used to immobilize the indicator molecules 116, a doping ratio of about 1:4 to about 1:20 AEMA to HEMA is preferred. The matrix layer 114 is provided so as to have stoichiometrically one pendant amino group for every three HEMA residues in the overall polymerized macromolecule of the matrix layer 114. This is illustrated by the formula in FIG. 8.

The polymer material of the matrix layer 114 may be cross-linked by standard cross-linking methods known in the art, including in a preferred embodiment a method using as a cross-linker group a bifunctional poly(ethylene glycol) (n) dimethacrylate. The cross-linker group may be added as per standard practice during the initial formulation of the monomer. This and other cross-linker groups are commercially available from PolySciences (Warrington, Pa.). Although the variable (n) may range from 1 to more than 1000, in a preferred embodiment of the invention, n=1000. The variable (n) may vary depending on the desired density, porosity, and hydrophilic properties of the matrix layer 114.

Figure 9:
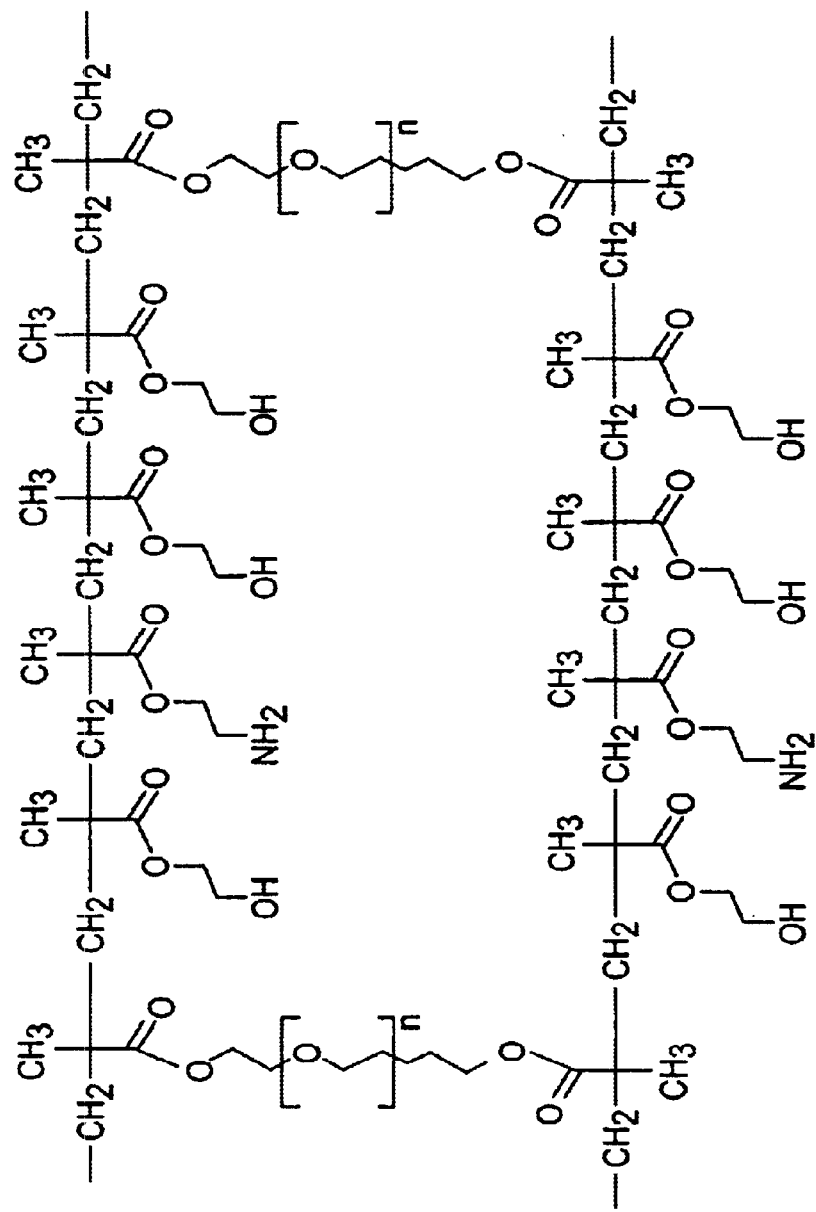
FIG. 9 illustrates a cross-linked and doped segment of the matrix layer in accordance with the present invention.

FIG. 9 illustrates a segment of the matrix layer 114 in accordance with a preferred embodiment of the present invention, which includes a pendant amino doped monomer (AEMA), a HEMA backbone, and a bifunctional cross-linker group.

The matrix layer 114 offers several advantages to the present invention, including allowing access of the analyte (e.g., glucose) to the light-absorbing indicator molecules 116; immobilizing the indicator molecules 116 to prevent them from leaching; maintaining the stability of the optical system of the invention; minimizing the amount of non-specific binding to the porous matrix of molecules other than the desired analyte; restricting access of molecules larger than the desired analyte; and permitting the porous matrix material to support one or more additional, biocompatible interface layers. The matrix layer 114 also is optically compatible with the sensor body 12 and is able to transmit excitation, emission, absorbance, or refractive index wavelength(s) of the indicator molecules 116.

Various methods for immobilizing the indicator molecules 116 within the matrix layer 114 are described in the literature and may range from mechanical entrapment to covalent immobilization. See, for example, A. P. Turner, *Biosensors*, pp. 85–99, Oxford Science Publications, 1987.

Figure 10:
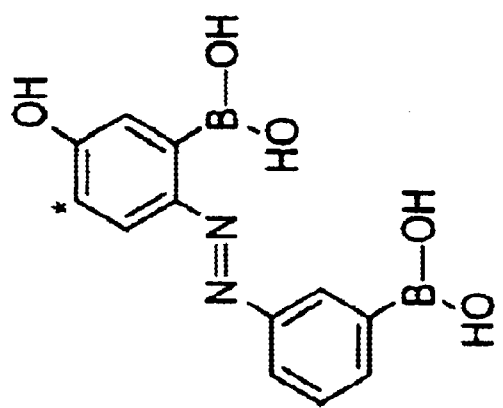
FIG. 10 depicts a glucose-sensitive, absorbance-modulated indicator molecule, 2,3'-dihydroxyboron-4-hydroxy-azobenzene ("Boronate Red") in accordance with the present invention.

In a preferred embodiment, the indicator molecule 116 is a glucose-sensitive, absorbance-modulated indicator molecule which may be covalently immobilized within the matrix layer 114. During polymerization, the indicator molecule 116 covalently attaches to the polymer backbone through a primary amine pendant group, and together they form the matrix layer 114. This form of immobilization is adaptable to various methods using different types of indicator molecules and different pendant groups on the polymer backbone. Examples of glucose-sensitive, absorbance-modulated indicator molecules include 2,3'-dihydroxyboron-4-hydroxy-azobenzene (also known as "Boronate Red"), as depicted in FIG. 10. Glucose can interact with the indicator molecules 116, as described in U.S. Pat. No. 5,512,246. Another similarly prepared preferred indicator molecule 116 for use in the present invention is depicted in FIG. 11.

Figure 11:
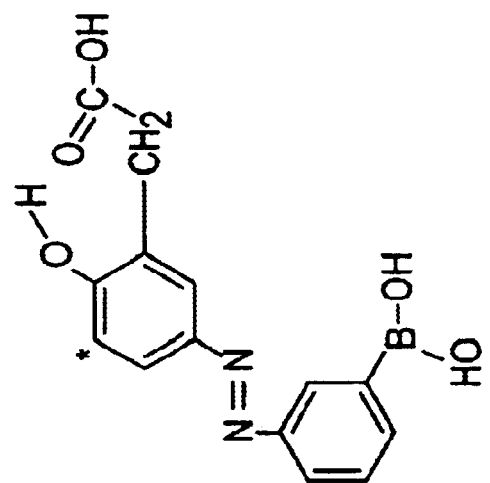
FIG. 11 depicts an additional embodiment of a glucose-sensitive, absorbance-modulated indicator molecule in accordance with the present invention.
Figure 12:
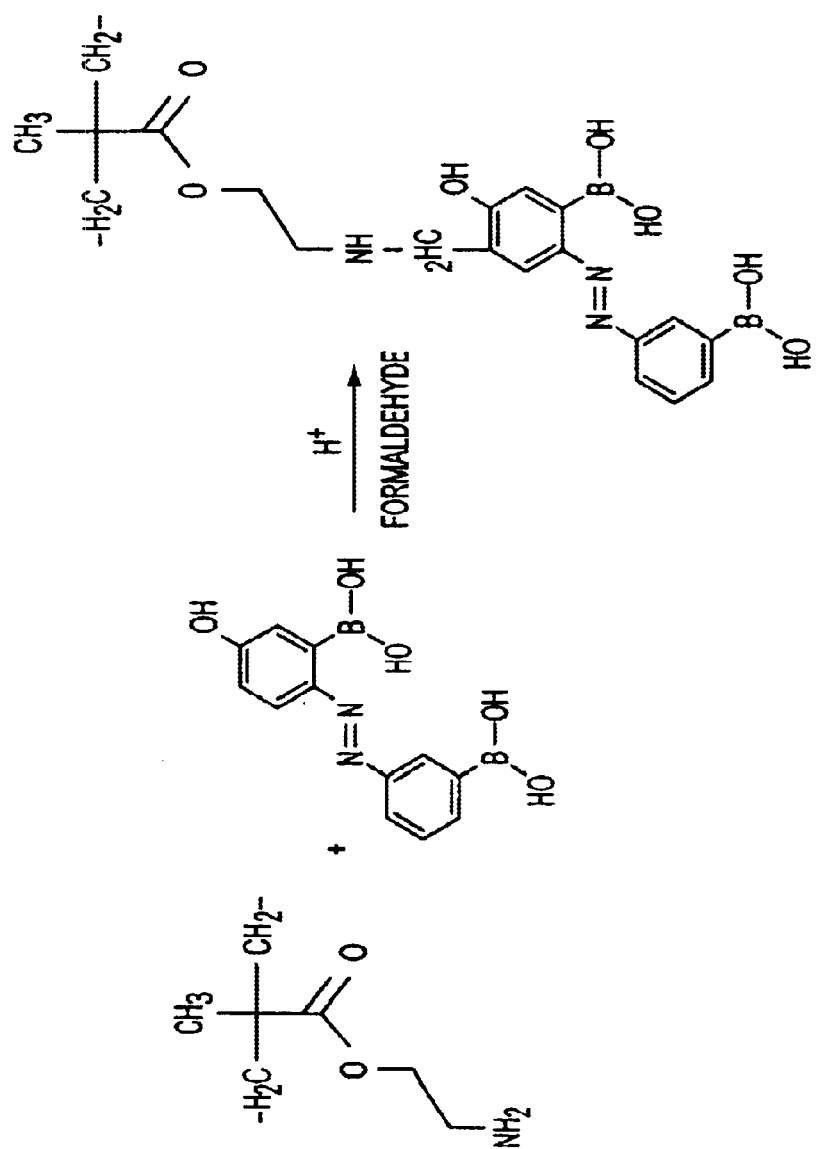
FIG. 12 depicts a standard Mannich reaction for linking the indicator molecule and the doped monomer AEMA.

In a preferred method of immobilizing the indicator molecules 116 shown in FIGS. 10 and 11 in the matrix layer 114, the ortho hydrogen position of the phenol group (represented by an "*" in the indicator molecules depicted in FIGS. 10 and 11) is aminoalkylated using the Mannich reaction, which is known in the organic chemistry art as a reaction wherein certain hydrogens of ketones, esters, phenols, and other organic compounds may be condensed in the presence of formaldehyde and an amine. The reagents for performing the Mannich reaction are commercially available from many chemical supply companies, including Pierce Chemicals. A standard Mannich reaction for linking the indicator molecule 116 to AEMA is depicted in FIG. 12. By copolymerizing AEMA and HEMA into the polymer backbone of the matrix layer 114, the indicator molecule 116 can be linked to the polymer material of the matrix layer 114 and rendered accessible to the analyte, e.g., glucose.

The indicator molecule 116 may be linked to the polymer material of the matrix layer 114 in various ways, including first coupling the indicator molecule 116 to AEMA prior to co-polymerization with HEMA. Alternatively, non-covalent, mechanical entrapment of the indicator molecule 116 may be used by first immobilizing the indicator molecule 116 to pendant amine groups of polylysine. The preimmobilized polylysine/indicator molecule precursor can then be mixed with HEMA prior to polymerization. Upon polymerization of the methacrylate, the polylysine/indicator molecule complex is trapped within the methacrylate matrix, while at the same time the indicator molecule 116 remains covalently immobilized to polylysine.

The sensor 110 otherwise is constructed as described above.

Figure 13B:
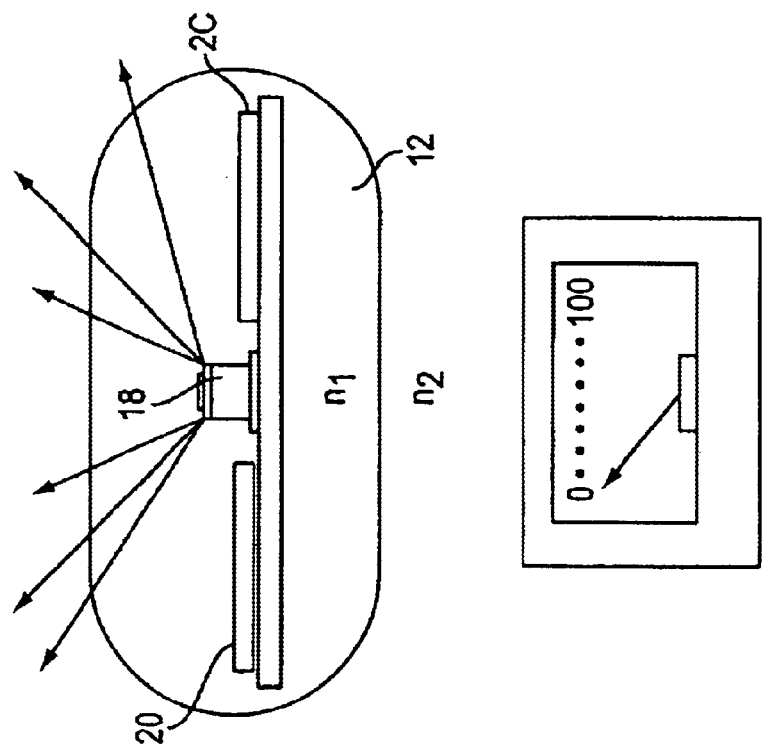
FIGS. 13a and 13b are schematic illustrations demonstrating the operating principle of a refractive index-based sensor according to another aspect of the invention.
Figure 13A:
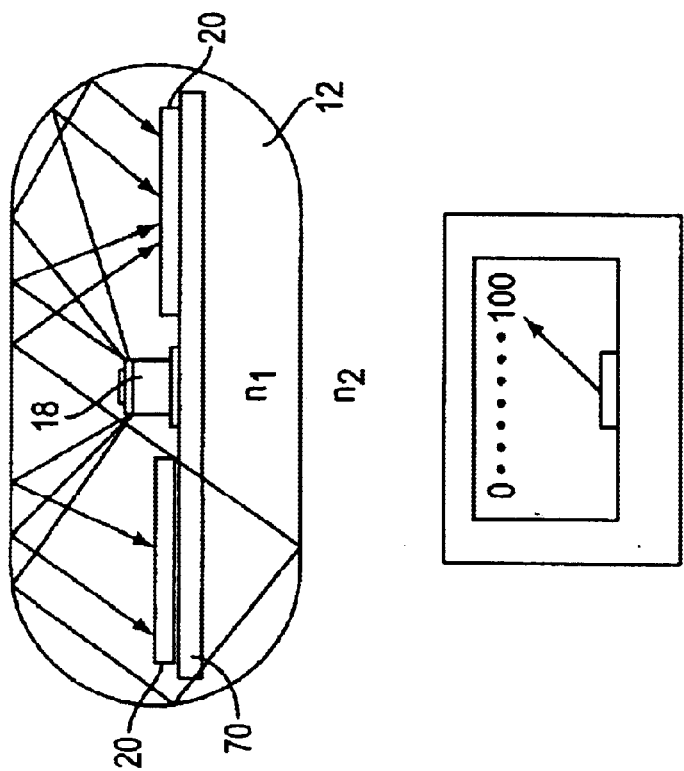

A sensor according to a third aspect of the invention takes advantage of the bean- or cold capsule-shaped construct described above (although by no means is limited to such a construct) to facilitate sensing the presence or concentration of an analyte based on changes in the refractive index of the medium in which the sensor is disposed (or the refractive index of a matrix encapsulating the sensor, if one is used). In general, light traveling through a first medium having a refractive index $n_1$ will pass across the interface between the first medium and a second medium having a refractive index $n_2$ if the angle of incidence of the light striking the interface (measured relative to a normal to the interface) is less than the critical angle $\theta_c$; light striking the interface at an angle of incidence greater than the critical angle, on the other hand, will be reflected internally within the first medium. The critical angle $\theta_c = \sin^{-1}(n_2/n_1)$. Thus, for the limiting case of $n_1 \gg n_2$ such that $(n_2/n_1)$ approaches 0 and the critical angle approaches 0°, light will be virtually entirely internally reflected within the first medium. Conversely, for the limiting condition of $n_1 = n_2$ such that the critical angle=90°, there will be no internal reflection within the first medium and all light will pass across the interface into the second medium. This principle is illustrated schematically in FIGS. 13a and 13b in the context of a sensor construct as taught herein. In FIG. 13a, the refractive index $n_1$ of the sensor body 12 is substantially larger than the refractive index $n_2$ of the surrounding medium. Therefore, all of the internal light generated by the source 18—which light, because of the waveguide properties of the sensor body, will have all possible angles of incidence from 0° to 90°—striking the interface at angles other than perfectly perpendicular will be internally reflected within the sensor body and will be sensed by the photosensitive elements 20. As shown in FIG. 13b, in contrast, where the refractive index $n_2$ is equal to the refractive index of the sensor body 12, the critical angle will be 90° (i.e., tangent to the interface between the sensor body and the surrounding medium), and therefore all light generated by the source 18 will pass out of the sensor body 12 and none (or almost none) will be sensed by the photosensitive elements 20.

It is possible to capitalize on the relationship between the critical angle and the relative refractive indices to determine the concentration of an analyte to which the sensor is exposed because, in general, the refractive index of a medium increases with the density of the medium. For example, if the sensor body is encapsulated in a membrane (not shown) which is selectively permeable (via size exclusion, charge exclusion, or permselectivity) to the analyte of interest, the density of the membrane will increase as analyte diffuses into it. This allows more light to pass out of the sensor body and causes less light to strike the photosensitive elements. In other words, with increasing analyte concentration, the level of internal reflection will decrease, and this decrease can be measured and correlated to the local analyte concentration.

It should be noted that some biological materials such as proteins, hormones, etc. do not dissolve in water and therefore will not permeate the membrane. Glucose, salts, and other small molecular weight compounds, however, are the primary metabolic analytes which will diffuse into the membrane and therefore are the analytes a refraction-based sensor could be used most effectively to measure.

In the most basic embodiment of a refraction-based sensor, a surrounding membrane would not need to be used. Such a basic embodiment could be used where the only matter varying in concentration is the analyte of interest. For example, as champagne or wine ages, the sugar content decreases, as does the density and hence the refractive index of the fluid. Therefore, a sensor according to this aspect of the invention could be placed in a bottle of champagne or a cask of wine as it is processing and used to measure sugar content as the champagne or wine develops. Other potential applications are determining the liquid level inside a vessel or determining the amount of moisture in fuel oil.

Finally, although specific embodiments of the various aspects of the invention have been described above, it will be appreciated that numerous modifications and variations of these embodiments will occur to those having skill in the art. Such modifications and variations and are deemed to be within the scope of the following claims.

Additional Embodiments of the Invention

In other embodiments of the invention, a sensor is provided which includes: (a) at least one analyte sensing indicator channel that operates as described above; and (b) at least one additional channel that serves as an optical reference channel. The optical reference channel preferably: (a) measures one or more optical characteristic(s) of the indicator molecule (i.e., the indicator molecule of the analyte sensing indicator channel) which is unaffected or generally unaffected by the presence or concentration of the analyte; and/or (b) measures one or more optical characteristic(s) of a second control indicator molecule which is unaffected or generally unaffected by the presence or concentration of the analyte. The optical reference channel can operate, for example, generally like the indicator channel. In the present application, indicator molecules that are unaffected or generally unaffected by the presence or concentration of an analyte are broadly referred to herein as control indicator molecules.

The optical reference channel can be used, for example, to compensate or correct for: (1) changes or drift in component operations intrinsic to the sensor make-up; and/or (2) environment conditions external to the sensor. For example, the optical reference channel can be used to compensate or correct for internal variables induced by, among other things: aging of the sensor's radiation source; changes affecting the performance or sensitivity of a photosensitive element thereof, deterioration or alteration of the indicator molecules; changes in the radiation transmissivity of the sensor body, or of the indicator matrix layer, etc.; changes in other sensor components; etc. In other examples, the optical reference channel could also be used to compensate or correct for environmental factors (e.g., factors external to the sensor) which could affect the optical characteristics or apparent optical characteristics of the indicator molecules irrespective of the presence or concentration of the analyte. In this regard, exemplary external factors could include, among other things: the temperature level; the pH level; the ambient light present; the reflectivity or the turbidity of the medium that the sensor is applied in; etc.

In the following description, like reference numerals refer to like parts to that of the previously described embodiments, and all alternatives and variations described herein-above with respect to such like parts can also be employed in any of the following embodiments where appropriate.

While a variety of methods for obtaining separate indicator channel and reference channel readings can be employed, a number of exemplary methods are discussed in the following paragraphs. These and other methods can be employed in any of the sensor embodiments described herein-below as would be apparent based on this disclosure.

First, an indicator membrane (e.g., such as the membrane 14" described below) can include indicator molecules that are sensitive to a particular analyte, such as for instance fluorescent indicator molecules that are sensitive to oxygen, and that are contained within a material that is permeable to that analyte while a reference membrane (e.g., such as the membrane 14" described below) can include the same indicator molecules within a material that is not permeable to that analyte. In the case of oxygen, for example, the indicator membrane can have an oxygen permeable matrix containing the indicator molecules in such a manner that oxygen freely passes through and contacts the indicator molecules (in one example, silicon rubber may be employed for the indicator membrane, which is very permeable to oxygen). As a result, fluctuations in values obtained in the reference channel should be substantially non-attributable to the presence or concentration of the analyte (e.g., oxygen), but rather to, as described above, for example (1) variables intrinsic to the sensor itself or (2) external environmental factors.

Materials that are substantially impermeable to an analyte (i.e., for the reference channel) can include, for example: a) materials that substantially prevent penetration of elements (see, as one example, U.S. Pat. No. 3,612,866, discussed below, wherein the reference channel is coated with varnish); and b) perm-selectable membranes, wherein the control indicator molecules are located within a matrix that is perm-selectable such that it allows certain elements to pass while blocking certain other elements such as the particular analyte (as one example, the matrix can allow negatively charged molecules to pass while blocking positively charged molecules).

Second, the indicator membrane can include indicator molecules that are sensitive to a particular analyte, such as for example fluorescent indicator molecules that are sensitive to glucose, and that are contained within a material that is permeable to that analyte while the reference membrane can also include a material that is permeable to that analyte, but which does not include the same indicator molecules, but rather control indicator molecules that are, in essence, substantially blind to that analyte. For example, when the analyte is glucose and such glucose is within a liquid (such as, for example, body fluids like blood, serum, tissue interstitial fluid, etc., or other fluids), placing the control indicator molecules within a material that is not permeable to such glucose would likely have the additional affect of blocking other factors such as changes in pH, etc., so that the first example described above would not be desirable. Accordingly, in this second basic method, the analyte is allowed to penetrate, but the control indicator molecules selected in the reference channel are chosen so as to be substantially blind to that analyte. As a result, fluctuations measured by the reference channel should be substantially unattributable to changes in the presence or concentration of that analyte.

Some illustrative, non-limiting, examples of control indicator molecules that are substantially blind to an analyte can be made as follows. First, reference is made to U.S. patent application Ser. No. 09/265,979, filed on Mar. 11, 1999, entitled Detection of Analytes by Fluorescent Lanthanide Metal Chelate Complexes Containing Substituted Ligands, also owned by the present assignee, the entire disclosure of which is incorporated herein by reference (and which is a continuation-in-part of application Ser. No. 09/037,960, filed Mar. 1, 1998, the entire disclosure of which is also incorporated herein by reference), which describes a recognition element, e.g., boronic acid, HO—B—OH, which is used to facilitate binding onto glucose. It is contemplated that, as some examples, control indicator molecules that are substantially "blind" to glucose, for example, can be made by omitting or altering such recognition element.

In particular, the '960 application describes indicator molecules with a fluorescent lanthanide metal chelate complex having the formula:

$$M(-Ch(-R_X))_Y$$

wherein: M represents a lanthanide metal ion; Ch represents a chelator comprising a ligand, preferably an organic ligand which can comprise any one or more of a β-diketone or a nitrogen analog thereof, a dihydroxy, a carboxyl coordinating heterocycle, an enol, a macrobicyclic cryptand (i.e., a cage-type ligand), a phenylphosphonic acid, or a polyaminopolycarboxylic acid. The organic ligand of Ch can also comprise any one or more of a heterocycle of nitrogen, sulfur, and linked carboxyls. The organic ligand of Ch can further comprise any one or more of an alkane or alkene group, preferably containing 1 to 10 carbon atoms, as well as aromatic, carbocyclic or heterocyclic moieties, including benzyl, napthyl, anthryl, phenanthryl, or tetracyl groups. Furthermore, one or more chelators complexed with M can be the same or a mixture of different chelators (so-called "mixed ligand or ternary chelates"). R represents an analyte-specific recognition element, one or more of which is bound to one or more ligands of the chelate complex, but need not be linked to every ligand of the chelate complex. In a preferred embodiment, R can be a boronate group or a compound containing a boronate group for detecting glucose or other cis-diol compound. X represents the number of recognition elements R bound to each of one or more chelators. X can be an integer from 0 to 8, and in certain preferred embodiments of the invention, X=0 to 4 or X=0 to 2. Additionally, the number of recognition elements R bound to each of one or more chelators may be the same or different, provided that for one or more chelators, X>0. Y represents the number of chelators complexed with M, and can be an integer from 1 to 4. In certain preferred embodiments of the invention, Y=1, Y=3 or Y=4. Accordingly, in these illustrative cases, in order to make control indicator molecules that are substantially blind to the analyte, the recognition element R can be omitted or altered as described above by those in the art.

Figure 21:
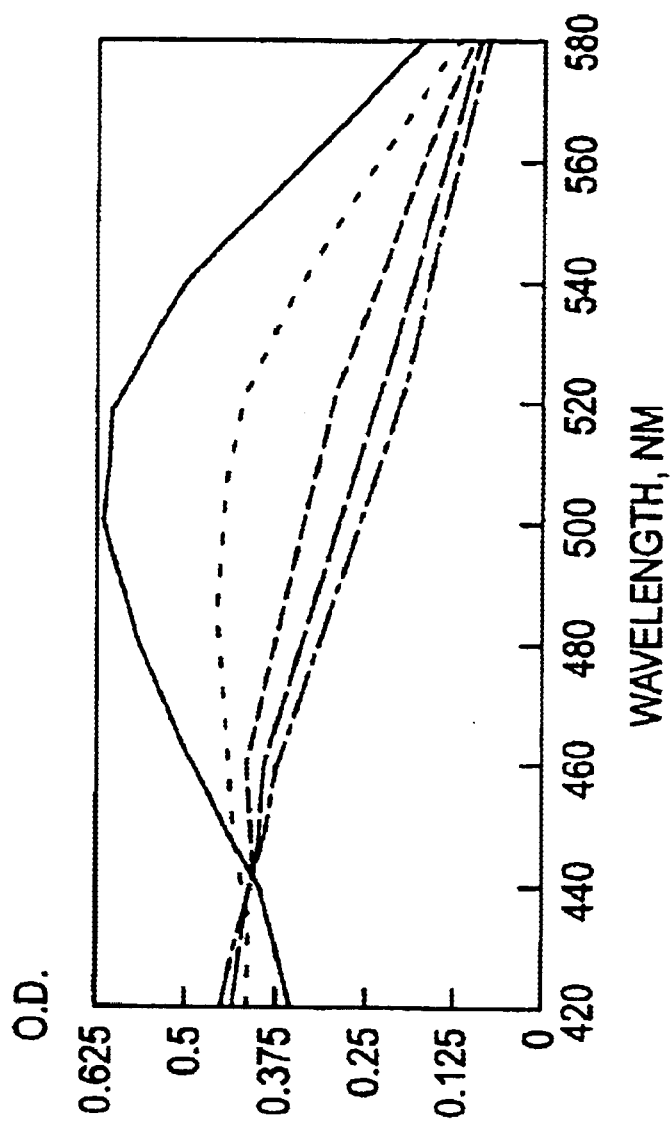
FIG. 21 is a graph (provided for illustrative purposes only, reprinted for convenience from FIG. 10 of U.S. Pat. No. 5,137,833, which is incorporated herein by reference) of light absorption (e.g., optical density) in they axis vs. excitation wavelengths (e.g., emitted from a radiation source) in the x axis, demonstrating an isosbestic point (i.e., a wavelength) at which absorption does not vary based on analyte concentration.

Third, another method of obtaining separate indicator channel and reference channel readings involves utilizing an indicator molecule having an isosbestic point at a particular wavelength or frequency (e.g., at about 440 nm in the non-limiting example shown for illustrative purposes in FIG. 21). An "isosbestic point" involves a point (i.e., substantially at a particular wavelength) where the absorptivity, for example, is the same irrespective of the presence or concentration of an analyte. That is, where a radiation source emits radiation, e.g., light, over a range of frequencies, light absorbance at certain frequencies will vary based on the presence or concentration of the analyte, but light absorbance at the isosbestic point will remain substantially constant irrespective of such analyte presence or concentration. Accordingly, in this third example, the indicator and reference channels would include indicator molecules having a specific isosbestic point (e.g., the same indicator molecules can be used in each channel). The indicator channel can include a filter (e.g., see filter 34 discussed below) over a photosensitive element (e.g., a photodetector) 20-1, discussed below, allowing light outside of the isosbestic point to be detected by the photosensitive element (e.g., at, for instance, about 500 nm in FIG. 21). On the other hand, the reference channel will include a filter (e.g., 34 below) over a photosensitive element (e.g., a photo-detector) 20-2, discussed below, allowing light substantially at the isosbestic wavelength to penetrate and be detected by the photosensitive element 20-2. As a result, any variation detected in the reference channel should be largely irrespective of analyte presence or concentration and can be used as a reference as discussed herein-above. Other indicator molecules having such an isosbestic point can be used based upon the particular application at hand. As just some of many examples, see among many other known sources: (a) M. Uttamial, et al., *A Fiber-Optic Carbon Dioxide Sensor for Fermentation Monitoring*, BIOTECHNOLOGY, Vol. 19, pp. 597–601 (June 1995) (discussing hydroxypyrenetrisulfonic acid (HPTS) (and also seminaphthorhodafluor (SNARF)) for $CO_2$ sensing) the entire disclosure of which is incorporated herein by reference; (b) A. Mills, et al., *Flourescence Plastic Thin-film Sensor for Carbon Dioxide*, ANALYST, Vol. 118, pp. 839–843 (July 1993) (Department of Chemistry, University College of Swansea, Singleton Park, Swansea UK) (discussing HPTS indicators for $CO_2$ sensing) the entire disclosure of which is incorporated herein by reference; (c) U.S. Pat. No. 5,137,833 (showing a glucose indicator with an isosbestic point at about 440 nm, see, e.g., FIG. 10 of the '833 patent reproduced herein at FIG. 21) the entire disclosure of which is incorporated herein by reference.

When indicator molecules having an isosbestic point are used, while the number of radiation sources (e.g., LEDs, for instance) may vary depending on circumstances, it may sometimes be preferable to utilize a plurality of radiation sources (e.g., LEDs) in certain cases. For instance, sometimes a radiation source (e.g., an LED) may not provide sufficient illumination at wavelengths around the isosbestic point such that it may be desirable to include an additional LED to provide sufficient illumination at such wavelengths.

The reference channels and the indicator channels of the present invention can utilize materials as described herein and as known in the art depending on the particular application at hand.

Several examples of using a reference or control during analyte detection are known in the art. For example, U.S. Pat. No. 3,612,866, the entire disclosure of which is incorporated herein by reference, describes a fluorescent oxygen sensor having a reference channel containing the same indicator chemistry as the measuring channel, except that the reference channel is coated with varnish to render it impermeable to oxygen. U.S. Pat. Nos. 4,861,727 and 5,190,729, the entire disclosures of which are also incorporated herein by reference, describe oxygen sensors employing two different lanthanide-based indicator chemistries that emit at two different wavelengths, a terbium-based indicator being quenched by oxygen and a europium-based indicator being largely unaffected by oxygen. U.S. Pat. No. 5,094,959, the entire disclosure of which is also incorporated herein by reference, describes an oxygen sensor in which a single indicator molecule is irradiated at a certain wavelength and the fluorescence emitted by the molecule is measured over two different emission spectra having two different sensitivities to oxygen. Specifically, the emission spectra which is less sensitive to oxygen is used as a reference to ratio the two emission intensities. U.S. Pat. Nos. 5,462,880 and 5,728,422, the entire disclosures of which are also incorporated herein by reference, describe a radiometric fluorescence oxygen sensing method employing a reference molecule that is substantially unaffected by oxygen and has a photodecomposition rate similar to the indicator molecule. Additionally, Muller, B., et al., ANALYST, Vol. 121, pp. 339–343 (March 1996), the entire disclosure of which is incorporated herein by reference, describes a fluorescence sensor for dissolved $CO_2$, in which a blue LED light source is directed through a fiber optic coupler to an indicator channel and to a separate reference photodetector which detects changes in the LED light intensity.

In addition, U.S. Pat. No. 4,580,059, the entire disclosure of which is incorporated herein by reference, describes a fluorescent-based sensor containing a reference light measuring cell 33 for measuring changes in the intensity of the excitation light source—see, e.g., column 10, lines 1, et seq. Furthermore, U.S. Pat. No. 4,617,277, the entire disclosure of which is also incorporated herein by reference, describes an absorbance-based sensor for carbon monoxide, in which a reference element 12 reflects light from a source 14 to a reference photocell to determine when a measuring element 10 needs replacement due to irreversible color change.

While a number of embodiments described herein are discussed in reference to the utilization of fluorescent indicator molecules, it should be readily understood based on this disclosure that these described embodiments can be modified to utilize any type of indicator molecules or combinations thereof depending on the particular circumstances at hand. For example, the membranes 14' and 14" (discussed below) can both include light-absorbing indicator molecules, such as those described herein-above. As another example, in some circumstances it may also be possible to utilize fluorescent indicator molecules in one of the indicator or reference membranes 14' or 14" while using light-absorbing indicator molecules in the other of the indicator or reference membranes 14' or 14"; in most cases, however, the indicator and reference membranes 14' and 14" will both use like indicator molecules, such as described herein.

In addition to the foregoing, a variety of other control methods could be employed. For example, in various other embodiments, the control channel could use materials or substances that are completely unrelated to the indicator molecules in the indicator channel. In that regard, for example, the substance of the reference membrane could merely have desirable characteristics with respect to one or more of, as some examples, reflectivity, temperature, pH, and/or various other factors. Notably, in certain embodiments, the reference membrane could contain no corresponding "chemistry", but could, for example, be used to just monitor reflectivity (this could be used, for example, to evaluate if an LED dimmed or if, for example, the surface of the membrane was affected in some manner).

It is contemplated that one or more reference channels can be incorporated in any of the embodiments disclosed in this application. A variety of preferred embodiments of sensors incorporating reference indicators are discussed herein-below. While some alternatives and variations in the following embodiments are described below, like reference numerals refer to like parts to the previously described embodiments, and all alternatives and variations described herein-above with respect to such like parts can also be employed in any of the following embodiments where appropriate.

Figure 14A:
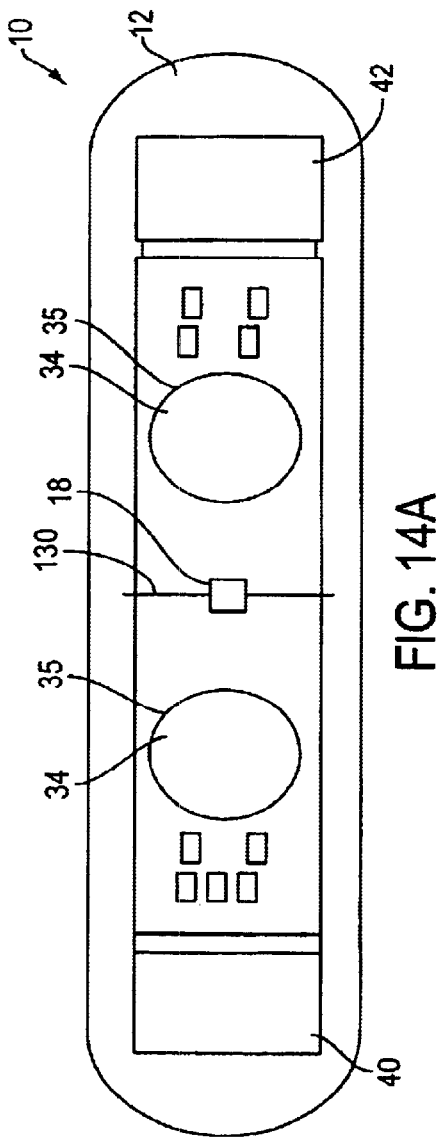
FIG. 14a is a top view of a sensor according to another embodiment of the invention incorporating a reference channel and a normal indicator channel.
Figure 14B:
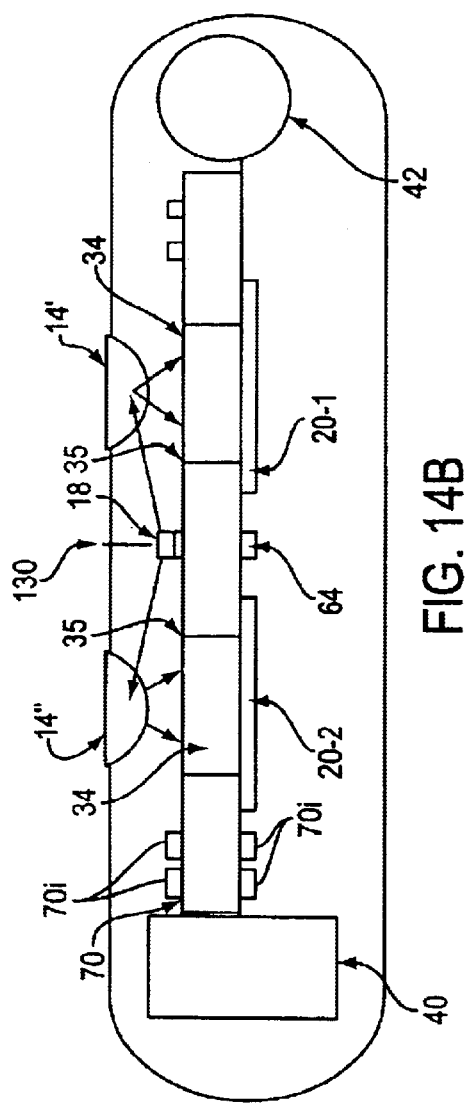

FIGS. 14(A)–14(B) illustrate a first embodiment of a sensor 10 incorporating an optical reference channel. As shown, the sensor 10 preferably includes: a sensor body 12; an indicator membrane 14' having fluorescent indicator molecules distributed throughout the membrane; a reference membrane 14" having fluorescent control indicator molecules distributed throughout the membrane; a radiation source 18, such as for example a single LED similar to that described herein-above; an indicator channel photosensitive element 20-1, made, for example, similar to photosensitive element 20 described herein-above; a similar reference channel photosensitive element 20-2; a circuit substrate 70 (shown schematically with exemplary circuit elements 70i mounted thereto); a power source 40, such as for example an inductive power coil as shown; and a transmitter 42 such as for example a transmitter coil as shown. In any of the embodiments described herein, the membranes 14' and 14" can be made, for example, with materials similar to any of the embodiments of the matrix layer 14 discussed above or can comprise any other appropriate materials within which the indicator molecules can be contained or upon which the indicator molecules can be coated. The membranes 14' and 14" (and/or the sensor body) can also include, if desired, a sensor/tissue interface layer similar to any of the embodiments of the layer 36, as discussed above. This illustrated embodiment can also include a number of additional elements, such as, for example, as shown: a filter 34 (e.g., to exclude a wavelength or a spectrum of wavelengths of light emitted by an LED, such as blue, and to allow passage of a wavelength or a spectrum of wavelengths of light emitted by the fluorescent material, such as red); a baffle 130 (e.g., to inhibit "cross-talk" of light radiated from the indicator channel and the reference channel); a mask 35 surrounding the aperture to each of the photosensitive elements; and/or a temperature sensor 64 (e.g., as described above).

In operation, the sensor 12 can function similar to that described above with reference to the embodiments shown in FIGS. 1–13. However, two separate sensory readings are obtained to provide: a) an indicator reading (via the channel including the indicator membrane 14' and the photosensitive element 20-1); and b) a reference reading (via the channel including the reference membrane 14" and the photosensitive element 20-2). Then, the reference reading can be used, for example, to provide more accurate sensor readings.

An exemplary operation of the device shown in FIGS. 14(A)–14(B) is as follows. First, the power source 40 causes the radiation emitter 18, e.g., an LED, to emit radiation. The radiation travels within the sensor and reaches both the indicator membrane 14' and the reference membrane 14" (as shown generally by arrows). Then, the molecules within these respective membranes excite, e.g., fluoresce, and light is radiated therefrom (as also shown by arrows) and received by the respective photosensitive elements 20-1 and 20-2. This operation is essentially like that described with reference to embodiments described herein-above and is thus not repeated. In order to eliminate or reduce "cross-talk" between light emitted from the membranes 14' and 14", a baffle 130 can be included. The baffle is preferably impervious to radiation that could affect the photosensitive elements—e.g., painted black or the like. In this manner, for example, a single radiation source, e.g., an LED, can be used for both of the "channels."

While the device can be fabricated in a variety of ways by those in the art based on this disclosure, one exemplary method of making the device shown in FIGS. 14(A)–14(B) can be as follows. Initially, an alumina ceramic substrate, which can readily be fabricated by a large number of vendors, can be provided for the circuit substrate 70. In addition, inductors, for example, can be provided as the power source 40 and the transmitter 42. The inductors and discreet components can be electrically connected to the substrate, such as using commonly available solder paste or conductive epoxy. In addition, other electronic components can be attached thereto using, for example, a conductive epoxy, such as in one preferred example ABLEBOND 84 from Ablestick Electronic Materials. Then, the components can be wire bonded to complete the circuit connections. Silicon photo-diodes, such as for example part no. 150-20-002 from Advanced Photonics, Inc., are preferably provided as the photosensitive elements 20-1 and 20-2, and are preferably flip chip mounted using ball bonds and conductive epoxy. In addition, the edges of the photosensitive element apertures in the substrate are preferably masked with a black, non-transparent and non-conductive material, such as, for example, E320 from Epoxy Technology, Inc. An optical filter material, such as, for example, LP-595 from CVI Laser Corp., is preferably placed in the photo-diode apertures (e.g., apertures cut within the substrate 70) to attenuate light from the radiation source and/or to attenuate ambient light. The radiation source employed can be, for example, an LED that emits light in the blue or ultra-violet bands. Then, this circuit assembly structure is preferably molded into an optically transparent encapsulant. The encapsulant can help serve as a waveguide and can also provide environmental protection for the circuitry. Then, the indicator and reference sensing membranes can be attached inside pockets in the capsule (e.g., inside depressions in the periphery of the capsule). This attachment can be accomplished, for example, by molding pockets into the capsule and then placing the sensing membranes therein, or by placing the indicator membranes into the mold prior to encapsulation so that pockets are formed around the membranes during encapsulation. As noted, this is just one preferred method of construction and the device can be constructed in a variety of ways. In addition, while the embodiments shown herein have only two channels (i.e., an indicator channel and a reference channel), other embodiments could contain multiple indicator and/or multiple reference channels.

Figure 14C:
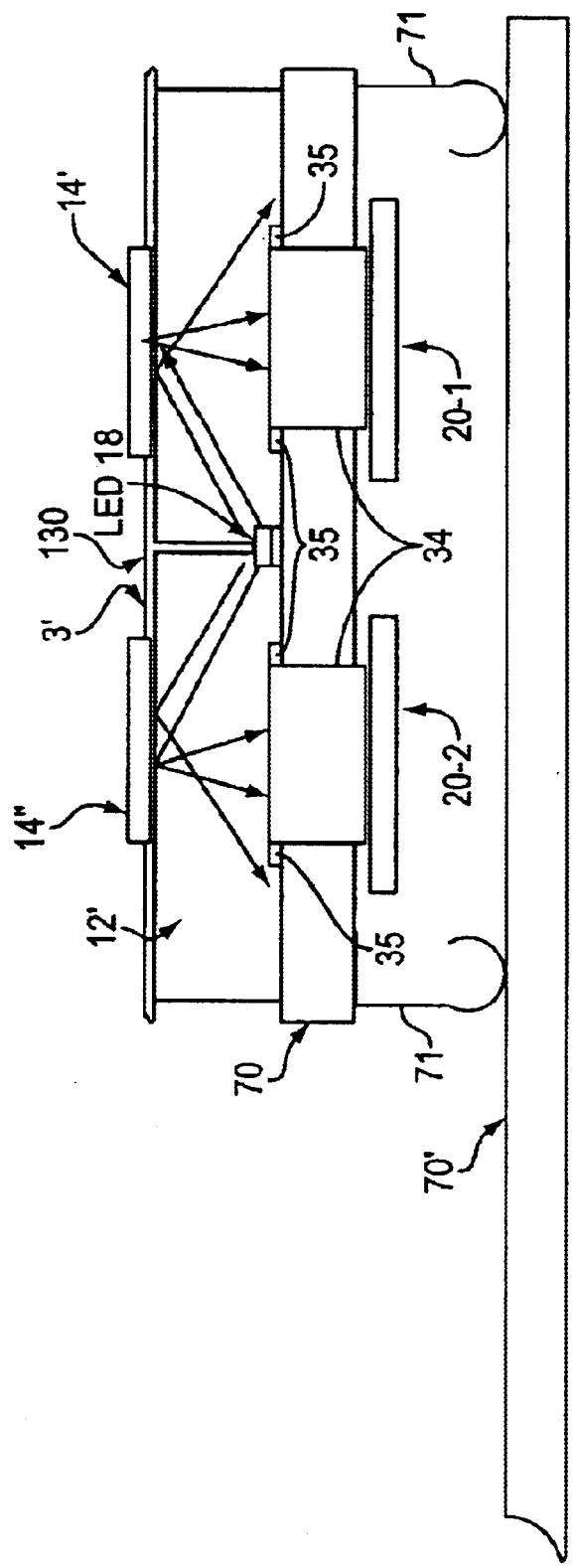
FIG. 14c is a partial side view of modified sensor similar to that shown in FIG. 14a including a reference channel and an indicator channel.

It is contemplated that the structure illustrated in FIGS. 14(A)–14(B) can be modified in a variety of ways. For example, as shown in FIG. 14(C), the device can be modified so that a circuit board 70 is fixed to a flexible circuit (e.g., a cable) as shown, such as via electrical leads or contacts 71. This allows, for example, circuitry to extend from the body of the capsule or the like (only a portion thereof is shown in FIG. 14(C)), such as for example: (a) to transmit power into the sensor from an external power source; (b) to transmit signals out of the sensor to an external receiver; and/or (c) for other purposes. As another example, as also shown in FIG. 14(C), the circuitry does not necessarily need to be fully encapsulated within the bean. In this regard, for example, the sensor 10 can include, as shown, an outer cover 3' and an encapsulating waveguide portion 12' formed within, for example, the illustrated, cross-hatched, region between the photosensitive elements and the indicator and reference membranes. Although less preferred, the interior of the sensor 10 could also include a cavity for the circuitry that contains a gas such as, for example, air, or even a liquid or another medium through which light, e.g., photons, of desired wavelengths can travel. Preferably, a waveguide material is provided that has a refractive index that matches or is near the refractive index of the material of the indicator and reference membranes so as to ensure travel of light from the membranes to the photosensitive element. In one exemplary, and non-limiting, construction, the waveguide portion 12' can be made from a PMMA material (i.e., poly(methyl methacrylate)), the circuit board 70 can be made with a ceramic material, the reference coating 14" can contain Ru (ruthenium) in an epoxy, the indicator coating 14' can contain Ru in silicone, the baffle 130 can be made with a black epoxy material, the radiation source 18 can be an LED, and the outer cover 3' can be made with a glass material.

Figure 14D:
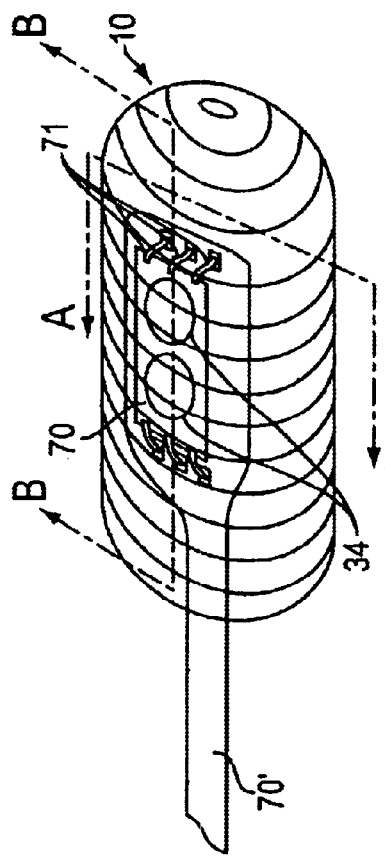
FIG. 14d is a perspective view of another embodiment of the invention incorporating a reference channel and an indicator channel similar to that shown in FIG. 14c.
Figure 14F:
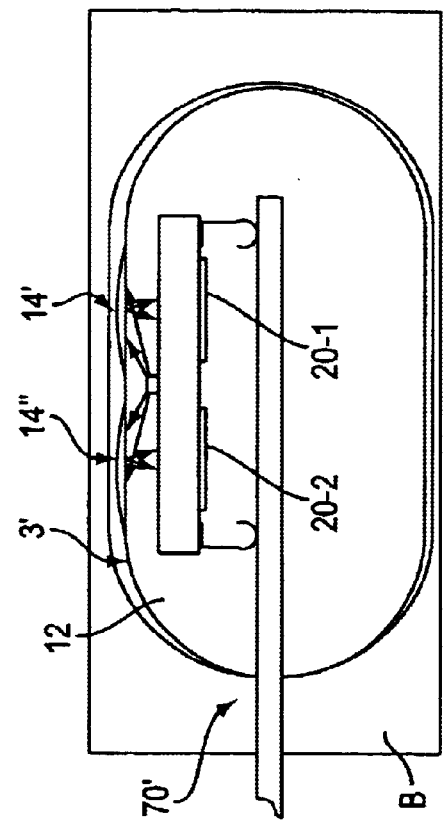
FIG. 14f is a cross-sectional view taken in the direction of the arrows B—B shown in FIG. 14d with the device shown within an external object.
Figure 14E:
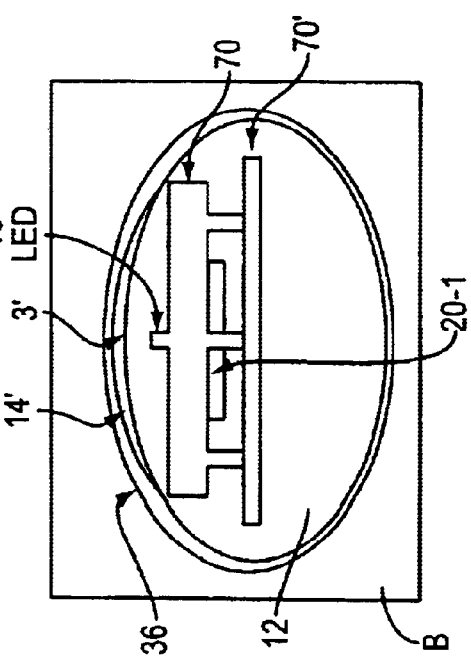
FIG. 14e is a cross-sectional view taken in the direction of the arrows A—A shown in FIG. 14d with the device shown within an external object.

FIG. 14(D) is a perspective view of a sensor 10 similar to that shown in FIG. 14(C), with like numerals indicating like parts. FIGS. 14(E) and 14(F) show widthwise and lengthwise cross-sections of the embodiment shown in FIG. 14(D) with the device inserted in a medium B (e.g., liquid, gas, etc.). As shown in FIG. 14(F), the flexible circuit or cable 70' can be made to extend from an outer surface of the medium B to a remote power-source, receiver or other device (not shown) as discussed above. As shown in FIGS. 14(E) and 14(F), the sensor body 12 can include an encapsulating waveguide material, such as described above, or an encapsulating waveguide material can be in a region 12' like that shown in FIG. 14(C), or, although less preferred, another substance can be used as described above.

FIGS. 15(A)–15(B) show an additional embodiment of the invention which is similar to that shown in FIGS. 14(A)–14(B), wherein the radiation source 18 is provided as two separate radiation sources, e.g., LEDs, 18-1 and 18-2 that are supported on a mount 18m. As shown, the LED 18-1 is directed toward the indicator membrane 14', while the LED 18-2 is directed towards the reference membrane 14". As shown, a baffle 130 is once again preferably included, in this case between the LEDs. Because multiple radiation sources, e.g., LEDs, are used in this embodiment, the radiation sources, e.g., LEDs 18-1 and 18-2, can be the same, e.g., emit the same light, or can be different depending on circumstances.

In embodiments wherein a plurality of radiation sources, e.g., LEDs, are used, certain considerations are preferably addressed. When one radiation source, e.g., LED, is used, aging or other factors therein can more likely equally affect both channels. However, when plural radiation sources are used (e.g., one for each channel), differences in radiation sources can create some discrepancies between channels. Accordingly, in such cases, it is desirable to: a) take steps to provide similar radiation sources (e.g., LEDs) for each channel; and/or b) to calibrate the radiation sources (e.g., LEDs) to one another. For example, when LEDs are formed from silicon wafers that are cut into LED chips (e.g., typically from flat, rectangular wafers having diameters of about 3–8 inches that are cut into an array of tiny LED chips), the LEDs are preferably selected from adjacent LEDs within the rectangular wafer or preferably from within a small distance from one another in the array (e.g., within about a half an inch, or more preferably within about a quarter of an inch, or more preferably within about an eighth of an inch, or more preferably within about a sixteenth of an inch) to be cut from the wafer. In that manner, the qualities of the selected LED chips should be more likely analogous to one another. In addition, where plural chips are used which have disparities between them, preferably normalizing calibrations between the LED chips are initially conducted under known test conditions to ascertain any discrepancies. It should be understood, as described herein, that in some cases, providing a plurality of radiation sources (e.g., LEDs) can have certain advantages—as some examples: a) a plurality of sources can facilitate illumination at desired locations; and/or b) a plurality of sources can, in some cases, be toggled back and forth to reduce cross-talk between channels, as discussed below. The device shown in FIGS. 15(A)–15(B) can be used, for example, in the same manner as the device shown in FIGS. 14(A)–14(B). In order to further reduce "cross-talk" between light emitted from the membranes 14' and 14", instead of or in addition to a baffle 130, the two radiation sources, e.g., LEDs, 18-1 and 18-2 can also be operated so as to alternate emissions back and forth between the respective LEDs. For example, the LED 18-1 can be activated for a fraction of a second, then the LED 18-2 can be activated for a fraction of a second, etc., with one LED remaining off during the short interval that the other is on. In that manner, cross-talk can be substantially reduced. In another alternative, the device can be adapted to provide a time delay between readings for the indicator channel and the reference channel (e.g., the indicator membrane could have pico-second decay while the reference membrane could have a nano-second decay, or vise-verse, such that separate channel readings can be made due to temporal differences in radiation emissions).

While FIG. 15(B) shows the LEDs with central axes each at angles θ of about 25 degrees from the generally horizontal upper surface of the substrate 70, these angles can be selected as desired and can vary, as just some examples, between about 0 to 90 degrees depending on circumstances. In some preferred embodiments, for example, the angles θ are about 60 degrees or less, or alternatively about 45 degrees or less.

It is contemplated that the structure illustrated in FIGS. 15(A)–15(B) can be modified in a variety of ways, similar to the embodiment shown in FIGS. 14(A)–14(B). For example, FIG. 15(C) illustrates that modifications like that shown in FIG. 14(C) can also be made, such as by: (a) including a flexible circuit (e.g., a cable) as shown, such as via electrical leads or contacts 71; (b) providing the sensor 10 with either a fully encapsulated interior, or with a partially encapsulated interior with an encapsulant waveguide portion 12' formed therein; (c) etc. In one exemplary, and non-limiting, construction, a waveguide portion 12' can be made from a PMMA encapsulant material, a circuit board 70 can be made with a ceramic FR4 circuit card, a radiation source 18 can include two LEDs, a mount 18m can be a Cu (copper) LED mount, and an outer cover 3' can be made with a glass material. In one preferred embodiment, as shown, a low index layer 12" is also provided over the filters 34 above the photosensitive elements 20-1 and 20-2. Once again, the device can be constructed in a variety of ways based on this disclosure and the above is only one of many exemplary constructions.

As shown in FIG. 15(B), the indicator membrane 14' and the reference membrane 14" can be formed within a pocket or the like at in the surface of the body 12. Alternatively, the membranes 14' and 14" could also be formed on the surface of the body 12 and not within a pocket or the like. The use of a pocket or the like, however, can help protect the membranes 14' and 14" in use and/or prevent the membranes from bulging outward from the side of the body (e.g., eliminating bulges can facilitate handling such as, for example, if the sensor is inserted into a patient via a trocar tube or the like). As described above, the sensor 10 can also include a sensor/tissue interface layer 36 thereover or partially thereover (and/or over the membranes 14' and 14") made, for example, with bio-compatible materials, e.g., such as any materials described herein.

FIGS. 16(A)–16(B) show an additional embodiment of the invention which is similar to that shown in FIGS. 15(A)–15(B), wherein the radiation source 18 is provided as two separate radiation sources, e.g., LEDs, 18-1 and 18-2 that are supported on mounts 18m1 and 18m2 on opposite sides of the circuit board 70, respectively. As shown, the LED 18-1 is directed toward the indicator membrane 14', while the LED 18-2 is directed towards the reference membrane 14". In this manner, for example, the circuit board 70 can actually operate as a baffle to reduce or eliminate cross-talk. As with the embodiments shown in FIGS. 15(A)–15(C), the angle θ can be selected as desired and is preferably between about 0 and 90 degrees—and is in some preferred embodiments less than about 45 degrees.

The device shown in FIGS. 16(A)–16(B) can be used, for example, in the same manner as the device shown in FIGS. 15(A)–15(B). In addition, the embodiment shown in FIGS. 16(A)–16(B) can also be modified in each of the same ways as described above with respect to the embodiment shown in FIGS. 15(A)–15(B). As shown, the upper and lower surfaces of the substrate 70 also preferably include masked areas 35 as shown. The radiation sources 18-1 and 18-2 are preferably located within these masked regions 35. In the embodiment shown in FIGS. 16(A)–16(B), the photosensitive elements 20-1 and 20-2 are mounted on the same side of the circuit board 70 as the respective membranes 14' and 14", while in the preceding examples, the boards 70 had cut-out regions through which radiation, e.g., light, passed to the photosensitive elements. In addition, in the embodiment shown in FIGS. 16(A)–16(B), a filter material 34 is preferably provided on top of these photosensitive elements rather than within such cut-outs. It should be understood that the various examples herein can be modified depending on circumstances by those in the art based on this disclosure. As one example, the photosensitive elements in the preceding embodiments could be mounted on the top of the boards 70 in a manner like that shown in FIG. 16(B) (e.g., on one side of the board).

FIGS. 17(A)–17(F) illustrate additional embodiments of multiple channel sensors that are made with: (a) an inner capsule containing the photosensitive elements, etc.; and (b) an outer sleeve having sensing membranes.

With reference to FIG. 17(A), a sensor 10 is shown having the electronic components inside a capsule 3". The capsule is preferably made of glass, but it can be made of any suitable material as described below. The capsule can also be made, if desired, from biocompatible materials. As another example, a soda lime glass capsule material like that of the Electronic Animal Identification Capsules of Detron-Fearing Company of St. Paul, Minn., could be used. Preferably, the capsule is hermetically sealed. As shown, a sleeve S is preferably located around the exterior surface of the glass capsule. The sleeve S preferably contains an indicator membrane 14' and a reference membrane 14" (e.g., fluorescent membranes for sensing, for example, glucose, etc.). The electronic circuitry can be like that used in any of the embodiments described herein-above. In a preferred construction, the electronic circuitry includes: components to facilitate power induction into the device; an excitation light source for the fluorochrome; means for photo-sensing; and means for signal transduction via radio frequency (RF) or passive inductive telemetry to an external reader. As with the preferred embodiments described herein-above, in one exemplary construction the entire sensor 10 is configured to be implanted subcutaneously below the skin of a patient. The components to facilitate power induction into the device preferably include an inductive coil 40 that generates the voltage and current necessary to power the circuit from an external magnetic field generator. The inductive coil 40 can be mounted, for example, on an a ceramic circuit board 70 or at the end of the circuit board (as shown). Alternatively, inductive coils can be utilized in multiple locations at various orientations in order to be best coupled with the external magnetic field generator.

The radiation sources, e.g., LEDs, 18-1 and 18-2 are preferably mounted on the substrate 70 appropriately to excite the indicator membranes 14' and 14" (e.g., fluorochrome areas) with light photons (as shown via arrows A1). As described herein-above, the light photons preferably excite the membranes 14' and 14" so as to give off fluorescence (as shown via arrows A2), which is detected by the photosensitive elements 20-1 and 20-2, respectively. In addition, other components can include an amplifier IC 70A and various passive components 70B to provide amplification and modulation circuits to transduce the photosensitive element intensity onto the telemetry coils.

One preferred method of constructing the device is, for example only, as follows. First, an electronic circuit is placed inside the glass tube 3", which is initially open on the left end E. Preferably, the glass is a borosilicate glass, such as in one embodiment Type 1 borosilicate glass N51A, made by Kimble Glass. (A wide variety of glasses and other materials could be used in other embodiments). After the electronic circuit is placed inside the glass tube 3", the interior is partially filled with encapsulant waveguide material 12' to the level indicated by dashed lines at 12L. As described herein-above, an encapsulant waveguide material can help to, for example, optically couple the light A-1 to the membrane surfaces 14' and 14" and to optically couple the fluorescent signals A-2 back to the photosensitive elements 20-1 and 20-2. Any optically suitable waveguide materials described herein-above or known in the art can be used. As above, the encapsulant waveguide material could also be applied throughout the entire interior of the glass tube 3", or in less preferred embodiments, the glass tube could be filled entirely with air or another substance as the waveguide. In some preferred embodiments, the waveguide material can include one or more of the following materials: silicone; GE RTV 615; PMMA; or an optical adhesive, such as NORLAND 63.

The capsule 3" is then preferably sealed at the end E to enclose the capsule. Preferably, the capsule is a glass capsule that is flame sealed at the end E to provide a smooth rounded end and to provide a hermetic seal. Preferably, prior to sealing the capsule, the electronic device is processed to remove moisture. For example, the device can be baked (e.g., at about 75° C. or greater for about 12 hours) and can be placed in a Nitrogen atmosphere to drive any residual moisture from the device and its components. Then, the assembled device can be powered and tested, if desired, to evaluate its operability before proceeding to the next assembly step—e.g., the step of applying the sensing membranes. In one exemplary construction, especially for use in-vivo, the length l shown in FIG. 17(A) can be about 10–15 mm long, and more preferably about 12.5 mm long, while the width h can be about 2–3 mm wide, and more preferably about 2.5 mm wide. In other preferred embodiments, the sensor can be substantially smaller—see, for example, preferred size ranges described herein-above (e.g., approximately 500 microns to approximately 0.5 inches long, etc.). It should be apparent, however, that the invention can be fabricated in any size and shape depending on circumstances.

One advantage of this embodiment is that the sensing membranes 14' and 14" can be manufactured in a separate piece that is placed over, e.g., slipped onto, the sensor capsule 3" following the above-described assembly process. In this manner, the membrane manufacturing steps can be advantageously separated from the electronics and encapsulation manufacturing steps.

In one preferred embodiment, the sleeve S is made with a plastic material (e.g., preferably, made with polyethylene and most preferably of a medical grade polyethylene (e.g., UHMWPE (ultra high molecular weight polyethylene)). The sleeve can be manufactured from any appropriate material depending on the circumstances and the particular use of the sensor. For example, when the sensor is used in-vivo, the sleeve can be constructed from biocompatible materials—some additional preferred, non-limiting, examples of biocompatible materials include polypropylene, PMMA, polyolefins, polysulfones, ceramics, hydrogels, silicone rubber and glass. The sleeve S is preferably an injection molded plastic sleeve sized such that the internal diameter of the sleeve can be precisely fit over the capsule. When assembled onto the capsule, the sleeve S preferably has sufficient elasticity to allow a tight mechanical fit that will not easily come off of the capsule 3". The sleeve S is preferably formed with holes, pockets, or cavities H to accommodate the indicator membranes 14' and 14" (e.g., to mechanically entrap the membranes). For example, fluorochrome pockets H can be readily insert molded in the sleeve. FIGS. 19(A)–19(I) demonstrate a variety of arrangements of the holes, etc., H on various sleeves S that can be utilized in various embodiments. Notably, the sleeve S should be configured such that when mounted on the capsule 3", the holes, etc., can be aligned sufficiently with the respective photosensitive elements 20-1 and 20-2. The device shown in FIGS. 17(A)–17(B) preferably has a sleeve constructed like that shown in FIG. 19(E)—e.g., with the holes H having an oval shape disposed substantial over the surface of the photosensitive elements. Alternatively, although less preferred as discussed above, the indicator membranes could be formed on the perimeter surface of the sleeve (e.g., so as to bulge outward therefrom) without such pockets therefor.

Another advantage of using an outer sleeve S is that the materials (e.g., discussed above) that can be used therefor can have good medical grade surfaces for subcutaneous tissue to bind to, which can advantageously help prevent the device from movement and migration within a patent, in-vivo, when the sensor is of the type implanted within a person (or within another animal). In addition, natural parting lines and roughness of the edges of such a molded sleeve can also help prevent such movement and migration. Prevention of movement or migration after implantation can be very important in some embodiments—for example, so that inductive power and telemetry coils can be maintained in optimal alignment between the implanted device and an external reader.

Figure 19A:
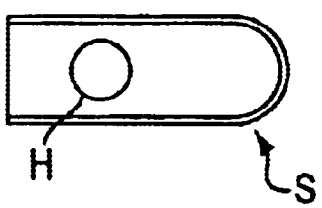
FIGS. 19a–19j show side views of a variety of possible sleeve constructions demonstrating various pocket arrangements and sleeve structures.
Figure 19E:
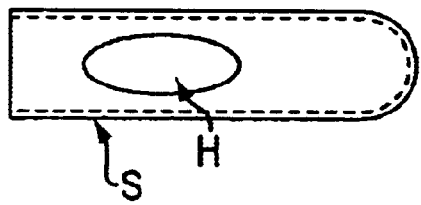
Figure 19B:
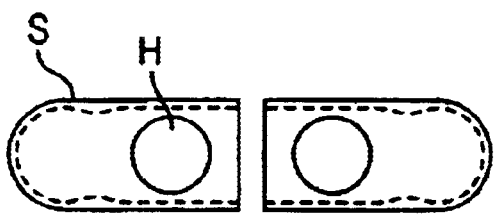
Figure 19F:
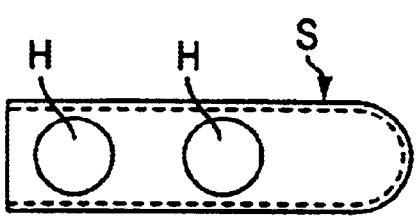
Figure 19C:
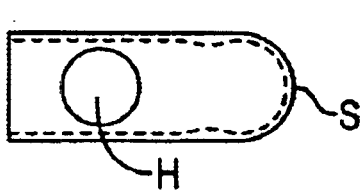
Figure 19G:
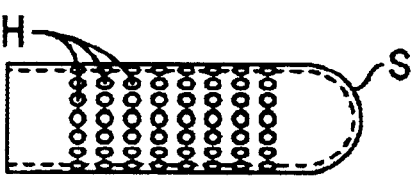
Figure 19D:
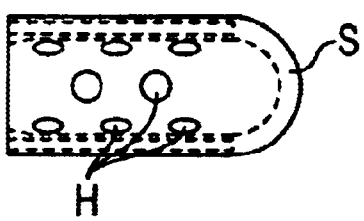
Figure 19H:
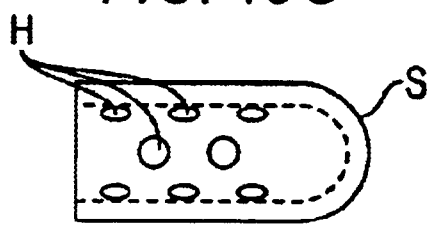
Figure 19I:
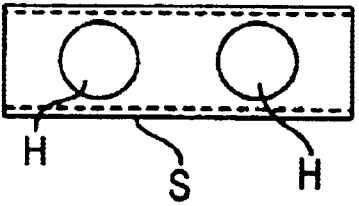

In other alternative constructions, the sleeve S could also be extruded in the shape of a tube (e.g,. into a cylinder like that shown in FIG. 19(I), discussed below) and applied on the capsule with a compression fit. In addition, the sleeve S could also be formed into a tube that is heat shrunk onto the capsule 3". The membrane pockets H could also be formed therein by molding, cutting, laser machining, or laser drilling. In addition, in some designs, thousands of small laser machine holes H can be fabricated in the side wall of the sleeve S.

Another advantage of using a membrane sleeve S is the ability to protect the indicator and reference membranes during manufacture, handling, storage, and, most importantly, during injection through a trocar into the subcutaneous tissue as is to be performed in some preferred embodiments. The mechanical forces and movement while implanting the sensor through a metal trocar may damage the exterior of the device if the surface is not adequately protected.

While a variety of exemplary membrane sleeves S have been described, various other membrane materials, sizes, locations, geometrical designs, methods of manufacture, etc., could be employed by those in the art in view of the above.

Once again, the arrangement of the parts within the sensor can also be varied by those in the art. For example, FIGS. 17(C)–17(D) show a second embodiment similar to the embodiment shown in FIGS. 17(A)–17(B) with the indicator membrane 14' and the reference membrane 14" on the same side of the circuit board 70 and with a single radiation source, e.g., LED, 18—similar to the embodiments shown in FIGS. 14(A)–14(C). All of the applicable variations described above with respect to FIGS. 14(A)–14(C) and to FIGS. 17(A)–17(B) could be applied to the embodiment shown in FIGS. 17(C)–17(D).

As another example, FIGS. 17(E)–17(F) show another embodiment similar to the embodiment shown in FIGS. 17(A)–17(C) with the indicator membrane 14' and the reference membrane 14" on the same side of the circuit board 70 but with two radiation sources, e.g., LEDs, 18-1 and 18-2 similar to the embodiments shown in FIGS. 15(A)–15(C) but with the LEDs spaced further apart in the illustrated example. All of the applicable variations described above with respect to FIGS. 15(A)–15(C) and to FIGS. 17(A)–17(C) could be applied to the embodiment shown in FIGS. 17(C)–17(D).

While the embodiments described herein-above included one indicator channel and one reference channel, as noted above the various embodiments described herein-above can be modified so as to include a plurality of indicator membranes (e.g., measuring the same or different analytes) and/or a plurality of reference membranes (e.g., measuring the same or different optical properties). In addition, it is noted that the principles related to the provision of a sensor 10 having a two part construction like that shown in FIGS. 17(A)–17(F) could also be employed within a basic sensor as described herein-above that does not utilize such a reference channel—for example, FIGS. 18(A)–18(B) illustrate an embodiment with a single photosensitive element 20 and a single source 18 that can be used to obtain a sensory reading as described above with reference to FIGS. 1–13 without a reference channel reading.

While FIGS. 18(A)–18(B) were described as being without reference indication, it is noted that a device having a single source and/or a single photosensitive element could still be used to provide separate indicator and reference readings in some embodiments, such as for example: a) a single LED may alternate emissions in different frequencies for alternating indicator and reference channel readings; b) in cases where the indicator membrane and the reference membrane have different frequency characteristics of radiation emission, a filter over the photosensitive element could be adapted to alternate passage of such different frequencies to the photosensitive elements; c) in cases where the indicator membrane and the reference membrane have different time characteristics of radiation emission, the device could be adapted to provide a time delay reading for the indicator channel and the reference channel (e.g., the indicator channel could have picosecond decay while the reference channel has nanosecond decay or vise-verse); d) etc.

As described above, FIGS. 19(A)–19(I) show some examples of alternative sleeve S and pocket H designs. It is noted that the devices shown in FIGS. 17(C)–17(F) preferably include a sleeve S like that shown in FIG. 19(E), configured such that the pockets H can be readily aligned over the respective photosensitive elements. In addition, the sleeve design could be like that shown in FIG. 19(I) wherein the sleeve S is formed into a tube that is open at both ends and that can be slid over the capsule. In addition, a plurality of sleeves S could also be employed (e.g., each to contain a respective membrane), such as shown in FIG. 19(A) wherein two sleeves S can fit over opposite ends of the capsule. In embodiments like that shown in FIGS. 19(D), 19(G) and 19(H), wherein pockets are provided around the perimeter of the sleeve S, the sleeve can be applied over the capsule without having to orient the sleeve and the capsule exactly in certain embodiments when the photosensitive elements are on one side of the circuit board 70 (e.g., when two channels are used, the pockets towards the left side of sleeve can contain reference membranes while the pockets at the right side can contain indicator membranes). Once again, these are merely exemplary designs and a variety of other sleeve and/or pocket designs could be made by those in the art.

Figure 19J:
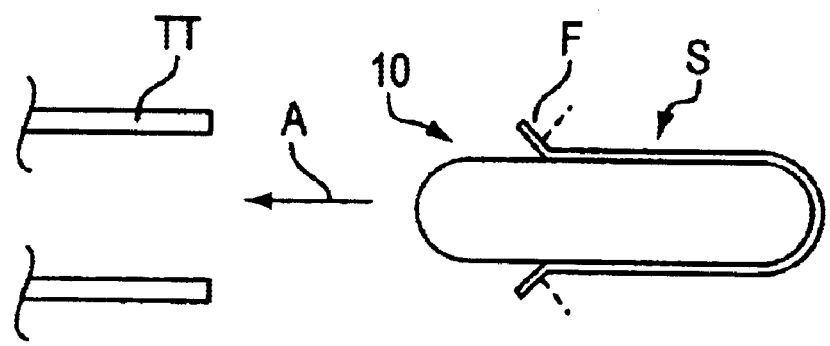

FIG. 19(J) shows yet another embodiment of the invention wherein the sleeve S is made with an outer annular flange F. The annular flange F is preferably formed so as to naturally (e.g., in an unbiased state) extend laterally outward from the side of the sensor as shown. Preferably, the flange F is made of absorbable or biodegradable material. The embodiment shown in FIG. 19(J) can be used, for example, in applications where migration prevention is desired. For instance, even when connective tissue is expected to hold the sensor in place over time, this embodiment can facilitate maintenance of proper positioning even prior to ingrowth of connective tissue. That is, the annular flange can help prevent movement of the sensor within a medium in which it is applied or inserted (e.g., such as within a patient). In a most preferred embodiment, the flange is flexible and is capable of bending over (e.g., to a position shown in dashed lines in FIG. 19(J)) upon insertion in the direction of the arrow A into a trocar tube TT) such that the sensor can be inserted into a patient. Then, after inserting the sensor 10 into a patient through the trocar tube and then withdrawing the trocar tube TT, the flange F will resume its original shape (or substantial resume that shape) and facilitate maintenance of the sensor in its proper inserted position. As noted, the flange F is preferably made of an absorbable or biodegradable material such that after a certain period of time the flange F will degrade—e.g., so that the sensor can be: a) easily removed; b) maintained in place via other means (e.g., such as via capillary ingrowth as described herein-above); and/or c) for other reasons. In alternative embodiments, a plurality of flanges F can be provided. In other alternative embodiments, the flange F can extend only partly around the circumference of the sensor (as opposed to completely annularly therearound). The sleeve S shown in FIG. 19(J) preferably includes respective indicator and control indicator molecules (e.g., within membranes in the pockets H) as described herein-above. However, it is contemplated that an annular flange F could be provided around a sensor of any of the embodiments disclosed herein, even where such a sleeve S is not included. In that regard, one or more flange F (e.g., preferably biodegradable) could be affixed to the exterior of any of the sensors described herein for similar functions and purposes. While the annular flange F is shown as being generally flat (e.g., with a generally rectangular cross-section), the flange F could also have other cross-sectional shapes—for instance, a band of suture material (preferably biodegradable) could be wrapped around the sensor. While the flange F preferably is capable of flexing inward and outward as shown, in certain embodiments the flange or band could also be made without such capabilities.

It is contemplated that the particular sensor construction (and especially the particular locations of the indicator membrane 14' and the reference membrane 14" in the sensor) can be selected based in part upon the particular environment within which the sensor is to be used. Notably, the indicator molecules (i.e., in the indicator membrane) and the control indicator molecules (i.e., in the reference membrane) should be exposed to substantially the same environment (i.e., to the environment containing the analyte being sensed). Accordingly, the membrane locations on the sensor will depend in part on the methods of use. As some examples: a) if a sensor is placed with its longitudinal axis vertical in a solution in which an attribute being tested may vary based on depth within the solution (e.g., within a wine bottle, etc.), it may be desirable to use, for example, one of the sensor constructions shown in FIGS. 16–17 wherein photosensitive elements are at like axial positions but on opposite sides of the sensor so that the membranes 14' and 14" can be disposed at like vertical elevations; while b) if a sensor is to be used, for example, sub-cutaneously with its axis generally parallel to the skin of the patient, it may be desirable to use, for example, one of the sensors shown in FIGS. 14(A) or 15(A). Among other factors, it should be understood that the sizes and locations of the membranes 14' and 14" (and the pockets H containing such membranes) will also depend in part on the field of view of the radiation source(s), e.g., LED(s), selected.

FIGS. 20(A)–20(B) show another embodiment that is similar to the embodiment shown in FIGS. 17(C)–17(D) except that the sleeve S is replaced by a removable film F. As shown, the film F includes the indicator membrane 14' and the reference membrane 14" thereon. As with the sleeve S, the membranes 14' and 14" are preferably formed within pockets, but, although less preferred, the membranes could also be formed on the film surface. The film F can be made of the same types of materials as the sleeve S as described above. The film F is preferably removably attachable on the capsule via the tackiness or adhesiveness of the material of the film itself or via an adhesive that will not appreciably affect the transmission of the radiation (e.g., light) to and from the indicator membranes (as one example, an adhesive like that used for POST-IT™ notes manufactured by 3M Corporation could be applied between the film F and the capsule 3"). The film F is preferably sized, as shown, so as to be large enough to support the indicator membrane 14' and the reference membrane 14" at their appropriate locations on the capsule 3". As shown, to remove the film F, for example, the corner C could be pulled and the film F can be removed in a similar manner to the removal of a BAND-AID™ adhesive bandage from a person's skin.

The various other embodiments shown herein-above could also be modified so as to include a film F rather than a sleeve S. In addition, while a rectangular film member F is shown, the film can be constructed in other shapes and forms depending on circumstances at hand. In addition, plural films F could also be used, such as for example including separate films for the reference and indicator membranes.

Thus, the embodiment shown in FIGS. 20(A)–20(B) and the various alternatives thereof can have a variety of benefits similar to that available with embodiments utilizing a removable sleeve S as described herein-above.

FIGS. 22(A)–22(C) show another embodiment of the invention wherein a shielding sleeve S' is formed around the body 12. In this embodiment, the sleeve S' is constructed to provide shielding from outside light. Two problems associated with sensors, such as with fluorescent glucose sensors, involve light other than that emitted by the radiation source 18. One source of light is from ambient sources such as sunlight and artificial lighting. Light of sufficient intensity can potentially saturate the sensor, rendering it useless for sensing fluorescent light. In addition, most artificial light sources have a significant AC (time varying) component; although filtering techniques can be employed to attenuate this source of noise, it can still significantly degrade the signal obtained. Another source of stray light is fluorescent emission of materials outside the sensor. This latter problem is particularly difficult in that the resulting signal generally cannot be electronically filtered from the indicator fluorescence. The embodiment shown in FIGS. 22(A)–22(C) can be used to substantially eliminate these effects from outside light interference.

In one preferred construction, the sleeve S' is formed from a substantially optically opaque, substantially non-reflective, layer of material containing a plurality of small holes H extending therethrough from its outer surface to the membranes 14' and 14". In one exemplary embodiment, the sleeve S' can be made with a black teflon tubing that is, for example, heat shrunk onto the body 12. Nevertheless, the sleeve S' can be formed with any suitable material. The holes H are preferably formed at an angle that is transverse to, and preferably substantially orthogonal to, the respective directions of propagation RL of light from the radiation source to the membranes 14' and 14" (e.g., see angles $\theta_1$ $_{and}$ $\theta_2$). The diameter of each hole H is preferably sufficiently small to substantially prevent light from passing directly from the radiation source 18 out of the sensor, and yet is preferably sufficiently large to allow analyte diffusion, or penetration, to the membranes 14' and 14". The number of holes H is preferably selected to allow relatively unrestricted diffusion of the analyte into the membranes. Thus, while some ambient light AL, see FIG. 22(C), may enter the sensor through the holes H, the penetration of ambient light therethrough should be largely attenuated.

FIG. 22(D) shows another alternative embodiment, wherein an inner glass capsule 3" is employed within an outer glass capsule 3'" (other embodiments could use an outer glass sleeve) with an indicator membrane 14' and a reference membrane 14" between the two capsules and with laser machine holes h through the outer capsule to allow analyte (e.g., glucose) migration into the indicator membrane 14'. It should be apparent based on this disclosure that other internal components (e.g., similar to that shown in FIGS. 16(A)–16(B)) would be included and, thus, such components are not be further described or shown with reference to FIG. 22(D).

FIGS. 23(A)–23(C) show yet another embodiment of the invention wherein a single LED 18 is used to excite both indicator molecules in the indicator membrane 14' and control indicator molecules in the reference membrane 14".

Typically, LEDs (e.g., LED chips) are manufactured by growing crystalline layers of semiconductor material 18-C (e.g., epitaxy) upon a substrate material 18-S. LED chips can be made very small—for example, the entire thickness of the semiconductor layers can be less than about 10 $\mu$m, or even less than about 5 $\mu$m, or even thinner. Typically, the substrate upon which the semiconductor layers are formed is substantially thicker—for example, greater than about 50 $\mu$m, or even greater than about 100 $\mu$m, or even thicker.

Figure 23D:
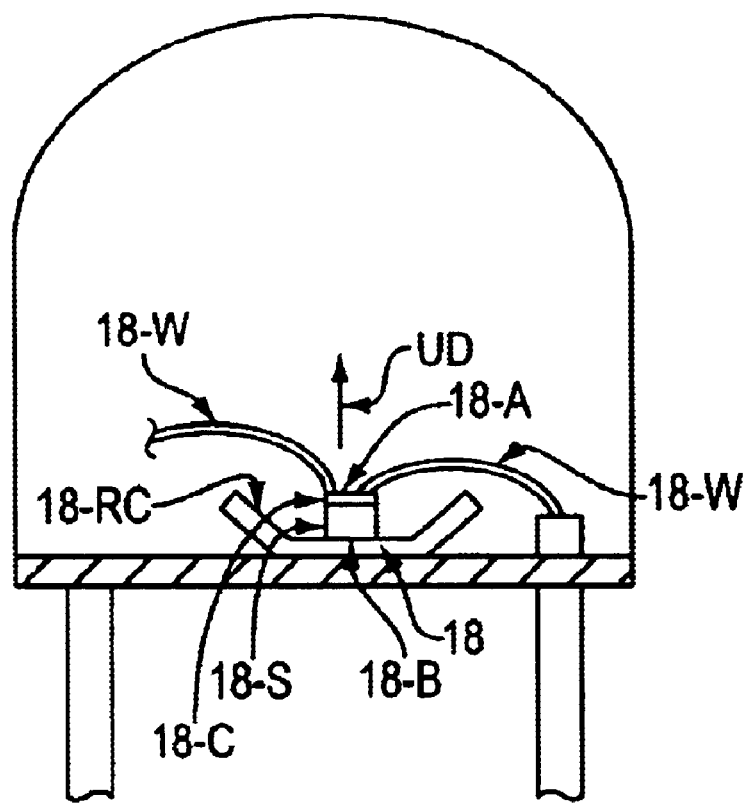
FIG. 23(D) is a schematic side view showing a common LED chip mounted within a reflector cup.

LEDs are traditionally used to emit light from a top side 18-A of the LED opposite the surface on which the LED chip is mounted (e.g., a reflector cup surface). As schematically shown in FIG. 23(D), an LED chip 18 is typically placed within a reflector cup 18-RC which ensures light transmission in an upward direction UD. As shown in FIG. 23(D), one or two small wires 18-W are typically connected to the top surface 18-A of the chip 18 (e.g., via gold contacts). In addition, the substrate 18-S is typically substantially transparent such that light transmitted by the semiconductor material is internally reflected within the substrate and reflects off the reflector 18-RC, preventing transmission through the bottom of the LED18-B. In fact, it has been generally considered in the art that LED chips are only for emission of light in a direction outward from the top surface 18-A of the LED chip.

The present inventors have found, however, that an LED chip 18 can be made to effectively emit light from both the top side 18-A and the bottom side 18-B of the LED chip. In one preferred embodiment, as shown in FIGS. 23(A)–23(C), the LED chip 18 is formed on a substantially transparent substrate (appropriate transparent substrate materials can include, for example, sapphire, silicon carbide and other suitable materials) that is mounted transverse to the top surface of the circuit board 70 (e.g., on a mount 18-m as shown) (preferably, the top and bottom surfaces 18-A and 18-B of the LED are arranged generally to maximize illumination of the indicator and reference channel and/or to maximize internal illumination of the sensor body). Preferably, a mask 34 is also included to inhibit cross-talk between the indicator channel and the reference channel.

Figure 24A:
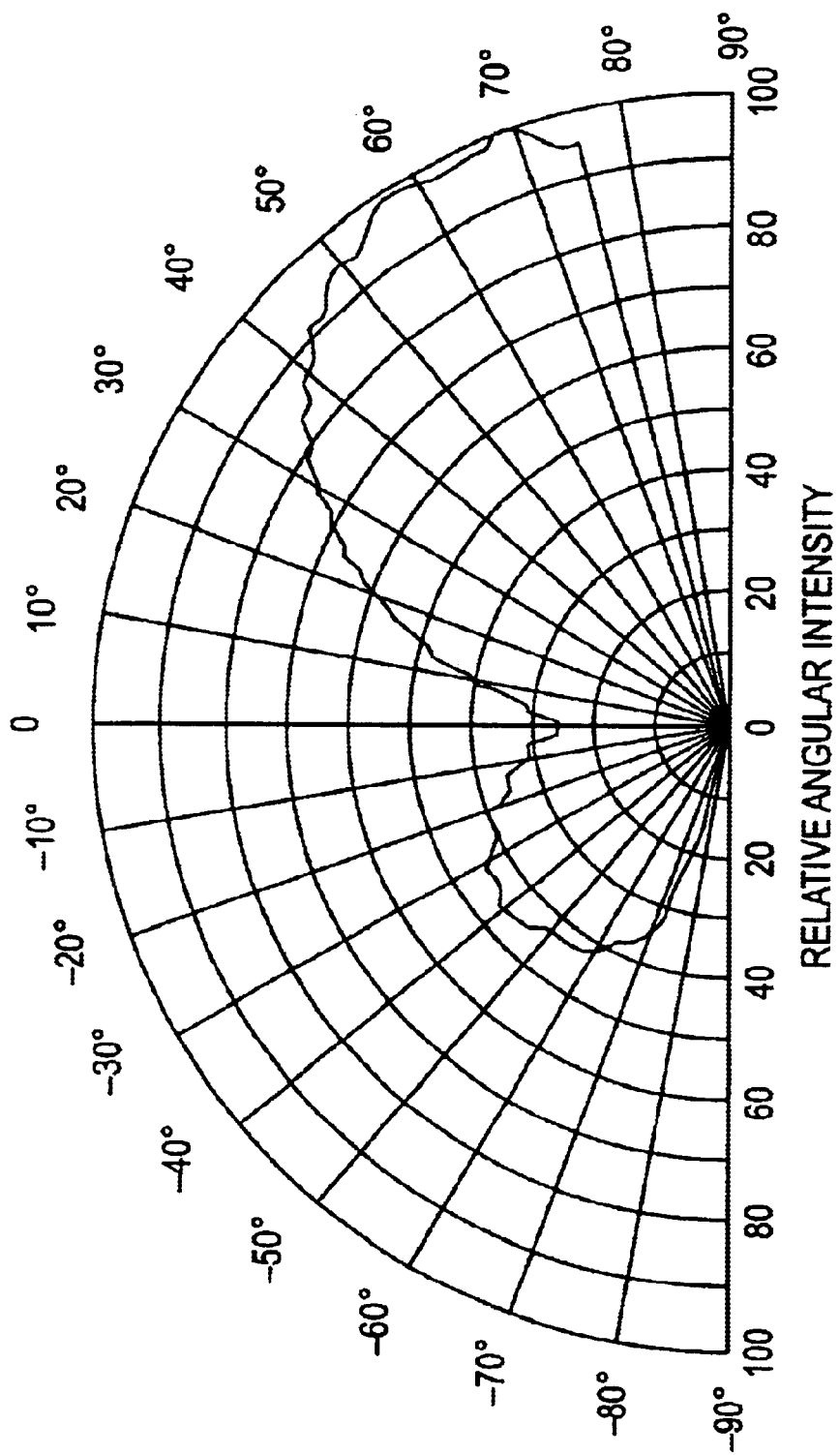
FIG. 24(A) is an explanatory graph showing illumination from two sides of an LED, in accordance with one illustrative example of the embodiment shown in FIG. 23(A).
Figure 24B:
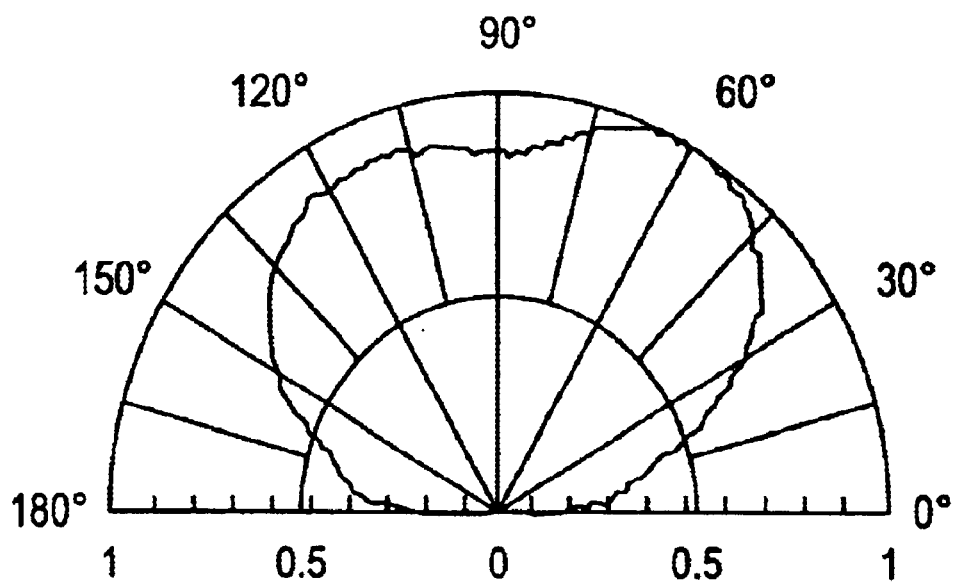
FIG. 24(B) is an explanatory graph showing illumination from an existing LED mounted on a flat surface.

In this manner, a single LED can be effectively used to illuminate both an indicator membrane 14' and a reference membrane 14". FIG. 24(B) is an illustrative example of a field of illumination from a known LED when conventionally mounted upon a non-transparent flat surface. The angles of 0 degrees and 180 degrees are parallel to the flat LED chip top surface, while 90 degrees is perpendicular thereto. As shown, illumination is substantially only from one side of the LED chip—i.e., from the top side 18-A. In contrast, FIG. 24(A) illustrates one example of illumination that can be achieved through both upper and lower sides, 18-A and 18-B, of an LED chip 18. In FIG. 24(A), the right side of the figure from 0 degrees to 90 degrees represents the light transmitted through the bottom 18-B of the LED, while the left side of the figure from 0 degrees to −90 degrees represents the light transmitted through the top side 18A of the LED. Thus, as shown in this example, a large amount of light can actually be emitted from the bottom side 18-B of the LED. In this illustrative case, a greater amount of light is actually emitted from the bottom side 18-B of the LED, which may be due, for example, to the presence of wires, electrical contacts (e.g., typically, one or more gold contacts are applied on top of an LED chip 18), or other materials on top of the top side of the LED chip. The measurements shown in FIG. 24(A) were obtained utilizing a MODEL LED-1100™ Gonometric analyzer made by Labsphere, of North Sutton, N.H. The LED used in FIG. 24(A) was a #NSHU550E™ LED by Nichia Chemical Industries, LTD, Tokyo, Japan. The LED used in FIG. 24(B) was a C470-9™ LED from Cree Research, Inc., of Durham, N.C.

In these embodiments wherein light is radiated both what is typically considered to be the top side 18-A and the bottom side 18-B of the LED chip to excite both indicator and control indicator molecules with a single LED, preferably a sufficient amount of light is transmitted both above and below the LED to sufficiently illuminate both channels. Preferably, the amount of light transmitted from one side is about 6 times or less, the amount of light transmitted from the other side, or more preferably about 4 times of less, or more preferably about 2 times or less, and in more preferred embodiments about equal. However, the amount of light radiated above and below the LED can vary significantly depending on circumstances.

Figure 25A:
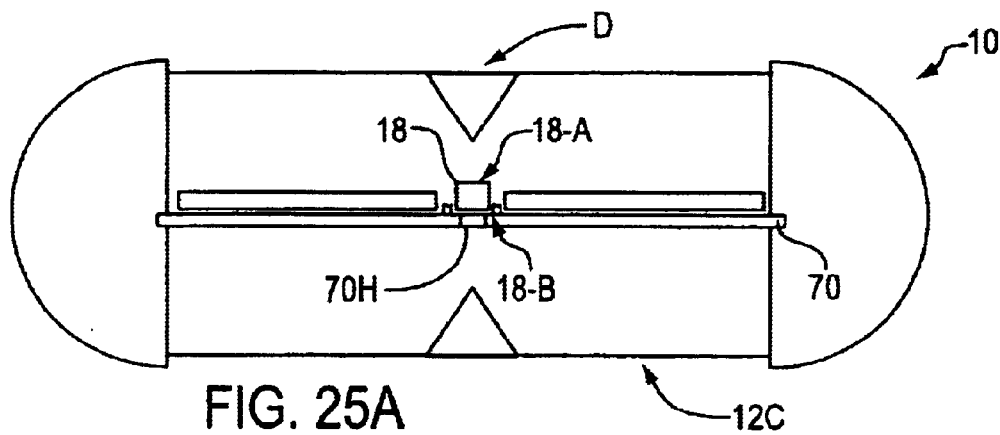
FIG. 25(A) is a cross-sectional side view of another embodiment of the sensor having radiation emitted from top and bottom sides of a radiation source (with the sensor membrane omitted).
Figure 25B:
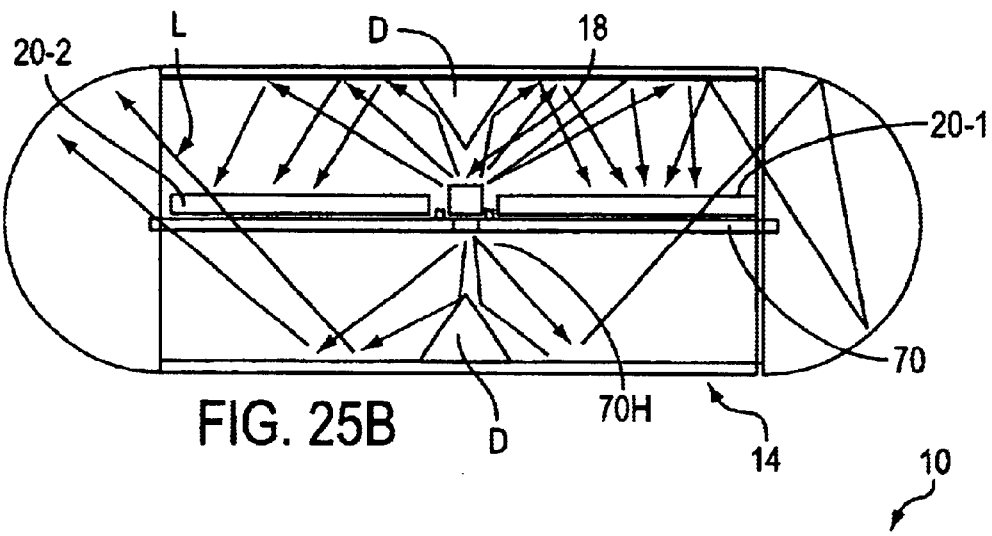
FIG. 25(B) is a cross-sectional side view of the embodiment shown in FIG. 25(A) with the sensor membrane positioned on the sensor.

FIGS. 25(A)–25(B) show a sensor 10 according to another embodiment having: a) a sensor body with a machined peripheral recess 12C around a circumference of the sensor body that contains an indicator membrane 14; b) a substrate 70 with a hole or window 70H beneath a radiation source (e.g., an LED) 18; and c) an optical deflector D with a generally triangular cross-section extending around the circumference of the sensor body. This embodiment is otherwise like that shown in FIGS. 14(A)–14(B). Electrical and other components (not shown) are like that described herein-above, and, thus, need not be further described with respect to FIGS. 25(A)–25(B).

In the embodiment shown in FIGS. 25(A)–25(B), the radiation source 18 emits radiation through its top and bottom sides 18-A and 18-B, as in embodiments described above. Radiation L, shown by arrows, is reflected within the sensor body, as in embodiments described above. As shown, radiation emitted through the window or hole 70H is reflected within the sensor body in such a manner that radiation from the top and bottom sides of the radiation source is used for detection. As shown, the sensor body 12 preferably includes a radiation deflector D situated such that radiation emitted generally vertically (i.e., above the top side or below the bottom side) from the radiation source is reflected laterally for better distribution and internal reflection and/or for ensuring that radiation is directed to outer regions of the indicator membrane. While the embodiment shown in FIGS. 25(A)–25(B) includes both indicator and control channels, it should be understood by those in the art based on this disclosure that the control channel can be eliminated in other embodiments and/or that any other modifications described herein with respect to other embodiments can also apply to the embodiment shown in FIGS. 25(A)–25(C) where appropriate.

Figure 26:
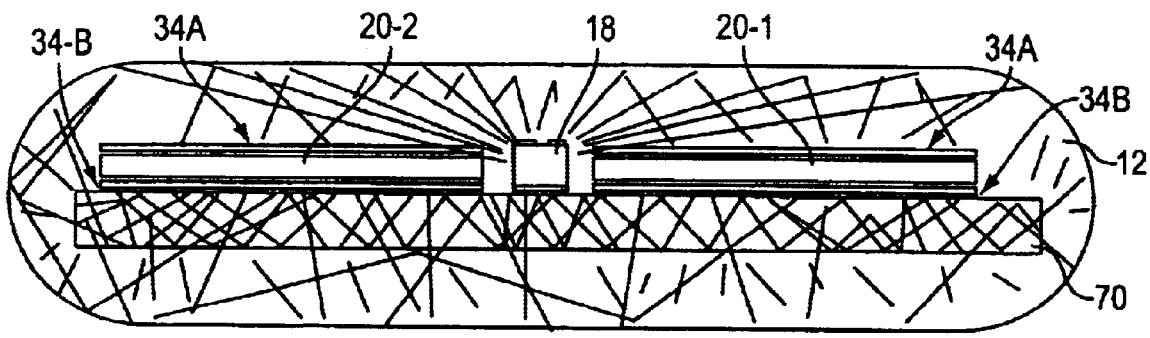
FIG. 26 is a cross-sectional side view of another embodiment of the sensor having an optically transparent circuit substrate.

FIG. 26 shows another embodiment of a sensor 10 having a substantially optically transparent circuit substrate 70. The substantially optically transparent circuit substrate 70 allows radiation to pass through the substrate 70. This facilitates the permeation of both excitation radiation and, in the non-limiting example of a fluorescent indicator, emission radiation throughout the sensor body 12, enabling more radiation to be received by the photosensitive members. As a result, the signal detection area can be increased (e.g., by signal capture at the top and bottom sides of the photosensitive elements) to substantially enhance signal detection.

Preferably, the radiation source 18 is mounted on the substrate 70 in such a manner that radiation is also emitted from the bottom side of the radiation source. The embodiment shown in FIG. 26 can, thus, be generally similar to that shown in FIGS. 23(A)–23(C) with respect to radiation being emitted from the top and bottom sides of the radiation source 18. Alternatively, radiation could be transmitted from only one of the top or bottom sides. The radiation source preferably includes an LED that is optically coupled to the optical substrate 70 (such as, for example, with an optical epoxy) to guide excitation light into the substrate.

The optically transparent substrate 70 can be made with, for example, sapphire, quartz, silicon carbide, GaN or other inorganic substrate materials that can be patterned with metallization. Other organic polymeric materials may also be used to fabricate the substrate. Any substantially clear material which can support the manufacturing of printed or etched electronic circuits can be used for this application. Other appropriate materials apparent to those in the art based on this disclosure can also be used. In one exemplary, but non-limiting, construction, the substrate 70 is made with quartz. Various vendors offer quartz substrates because such substrates are advantageous in other unrelated applications in the telecommunications industry, such as in high frequency applications. For example, MIC Technologies™ (an Aeroflex Company, 797 Turnpike St. North Andover, Mass. 01845) offers quartz substrate fabrication as a circuit substrate option. The substantially optically transparent substrate can then be used, with methods well known in the art, to attach parts using a standard hybrid circuit attachment method (e.g., conductive epoxy, solder, wire bonding, non conductive epoxy, etc.). Once all of the parts have been attached, the entire circuit can be, for example, immersed in a monomer solution and then a polymer reaction can be, for example, initiated using heat or radiation, such that a circuit can be formed that is potted, enclosed, and sealed within a waveguide polymer (e.g., PMMA) (i.e., as described herein-above).

As indicated above, the embodiment shown in FIG. 26 preferably includes photosensitive elements that can detect radiation directed at their top and bottom sides. Typically, photosensitive elements can only detect radiation directed at their top sides. In one preferred construction, the photosensitive elements include photoresistors.

A photoresistor is routinely fabricated by a simple chemical deposition process which places a photosensitive chemical substance within a circuit. When photons contact the surface of the deposited material, a change in resistance occurs and the circuit thus varies its resistance as a function of incident light intensity. Typically, the photoresistive material is deposited on opaque substrates such as ceramics. This causes the resultant photoresistor device to be sensitive in only one direction because light cannot penetrate the opaque substrate from the bottom side (i.e., the side adjacent the substrate).

In common applications of photoresistive detectors, this "unidirectional" construction is adequate. In preferred embodiments of the present invention, however, both excitation and emission light is dispersed throughout the device. Two notable objectives in preferred embodiments of the invention are to maximize the amount of light from the excitation source which is incident on the indicator membranes and to maximize the amount of fluorescent signal light which is captured by the photosensitive elements. Contrary to these objectives, opaque circuit substrates (such as those made of ceramic, polyimides, fiberglass, etc.) can block a substantial amount of light from propogating throughout the device and, thus, can reduce the overall sensitivity of the sensor. On the other hand, the embodiment illustrated in FIG. 26 can greatly promote both of these objectives. By depositing the detector material on a substantially clear substrate, the substrate can function as a larger area capture waveguide and can thereby convey, for example, additional fluorescent signal light to the photosensitive element. Furthermore, by mounting the radiation source, e.g., LED, onto a substantially clear substrate, substantially all of the radiation, e.g., light, radiated from the excitation source, can be more uniformly propagated throughout the device and, thus, more uniformly, and with greater power efficiency, directed to the indicator membrane.

The embodiment shown in FIG. 26 is not, of course, limited to photoresistive detectors, but other photosensitive elements can be used, such as, for example, photodiodes, transistors, darlingtons, etc., where appropriate.

When radiation is received at both sides of the photosensitive elements, high pass filters 34A and 34B are preferably provided above and below the photosensitive elements 20-1 and 20-2 in order to, for example, separate excitation radiation from fluorescent emission radiation. The high pass filters can be used, if desired, to adjust the spectral selectivity for the photosensitive elements. A high pass filter can be installed on both sides of the photosensitive elements by applying, for example, a filter epoxy, such as that available from CVI Laser, and others as described above with respect to the embodiment shown in FIG. 1.

Rather than, or in addition to, using filters 34A and 34B, the photosensitive elements can be made with materials that can be adapted, e.g., tuned, to be sensitive to particular wavelengths. The photosensitive elements could, thus, be able to be tuned to substantially sense, for example, fluorescent emission radiation rather than excitation radiation from the radiation source. In this regard, photoresistive detectors can be chemically tuned to be sensitive substantially at a specific wavelength, thereby reducing or eliminating the need for a separate filter element. Appropriate materials are readily commercially available. Known devices are produced and sold by, for example, Silonex Inc.™, (2150 Ward Ave, Montreal, Quebec, Canada, H4M 1T7) where peak wavelength sensitivity is adjusted and optimized based on varying ratios of dopants and mix ratios within a cadmium sulfide base (and others).

Although discussed in reference to the embodiment of FIG. 26, the "tunable" photosensitive elements described herein can also be advantageously incorporated into any of the embodiments described herein in other embodiments of the invention.

The embodiment shown in FIG. 26 preferably operates like embodiments described herein-above. To avoid unnecessary repetition, elements of the sensor shown in FIG. 26, e.g., electronic components, etc., are not shown and/or not described in relation to this embodiment. It is contemplated that the embodiment shown in FIG. 26 can be modified by those in the art in the same manner as any of the other embodiments described herein where appropriate.

Figure 27A:
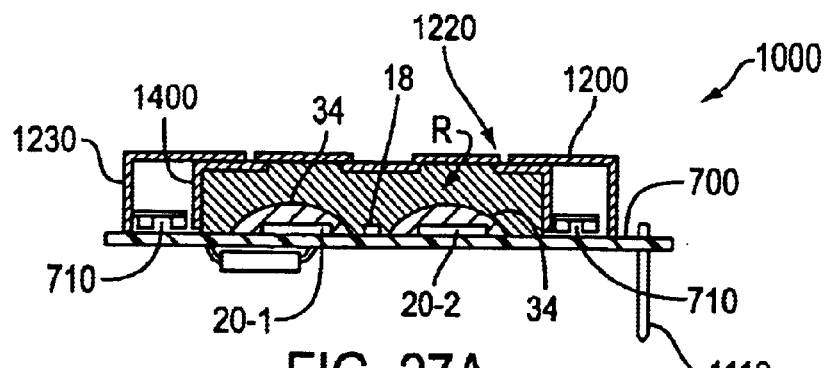
FIG. 27(A) is a cross-sectional side view, taken along the line 27—27 in FIG. 27(B), of another embodiment of the sensor having an internal heating element to inhibit condensation on the sensor.
Figure 27B:
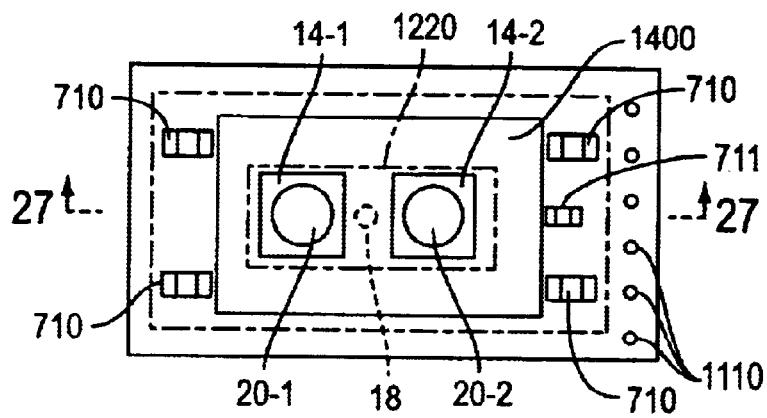
FIG. 27(B) is a top view of the sensor shown in FIG. 27(A).
Figure 27C:
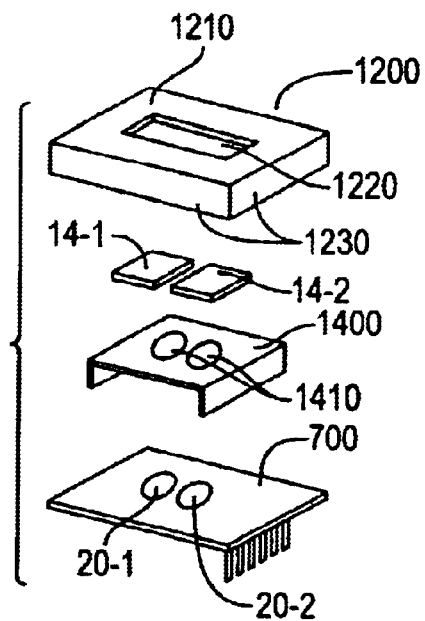
FIG. 27(C) is an exploded perspective view showing components of the sensor in FIG. 27(A).

FIGS. 27(A)–27(C) show another embodiment of a sensor 1000 with an internal heater. In the illustrated example, the sensor 1000 is not necessarily required to include a circuit substrate embedded entirely inside a waveguide, capsule or the like. It is contemplated, however, that a heater of this embodiment can be employed in any of the embodiments described herein, or in any other appropriate sensor housing. In the illustrated example, the sensor 1000 has a chip-like construction with a generally rectangular configuration with leads 1110 extending therefrom. The leads can be used to provide power, signals, etc., to and/or from the sensor.

The embodiment shown in FIGS. 27(A)–27(C) incorporates several unique design features having particular advantages in, for example, the detection and measurement of analytes in humidified gases. In a preferred, but non-limiting, example, the illustrated device is used as an oxygen sensor. Exemplary applications include, but are not limited to, the breath-by-breath measurement of oxygen during the respiration of humans or animals—e.g., where the sensor is exposed to cool/dry air during inhalation and to warm/humid breath during exhalation. The illustrated design can accurately measure, for example, the oxygen content during all phases of temperature and water vapor (humidity) variation. While the illustrated example is preferably used for the measurement of oxygen, other examples can be used to measure other analytes—for example, sensitive membranes for the measurement of carbon dioxide, another gas, or several gases could be employed.

In summary, in the illustrated example, the sensor 1000 includes a cover 1200 having a top wall 1210 with an opening 1220 and four depending side walls 1230. The bottom of the cover is configured to fit on top of a substrate 700 to form a box-like enclosure. As shown, the substrate 700 has photosensitive elements 20-1 and 20-2, a radiation source 18 and other electronic components (not shown), and a heating element 1400 mounted thereon. In the illustrated embodiment, the heating element 1400 extends over the photosensitive elements 20-1 and 20-2. The heating element has cut-out openings 1410 to allow radiation from the source 18 to pass to membranes 14-1 and 14-2 which are preferably located above the heating element. As shown, the membranes are preferably exposed via the hole 1220 in the cover 1200. The entire region R between the heating element, the sensor membranes and the substrate preferably contains a waveguide material as in embodiments described hereinabove.

The heating element 1400 can be made with any appropriate material (e.g., heat conductive material(s)), such as for example copper alloys, other heat conductive metals, or the like. The heating element 1400 can be made from any material having appropriate thermal properties. In order to heat the heating element 1400, the substrate 700 preferably includes a plurality of heat generators 710 (e.g., heater resistors or semi-conductor resistors) thereon that transfer heat to the heating element. In the illustrated, but non-limiting, embodiment, four heater resistors 710 are utilized. The heat generators 710 are preferably located adjacent (e.g., contacting or sufficiently close to) the sides of the heating element 1400 to transfer heat thereto.

The heating element 1400 serves, for example, the following two purposes: 1) keeping the signal and reference membranes 14-1 and 14-2 at substantially the same thermal equilibrium; and/or 2) heating the membranes 14-1 and 14-2 to a temperature that is above the dew point of humidified gases to be measured. In the example of human respiratory monitoring, this temperature value can be, for example, slightly above about 37° C. In one exemplary construction, the invention employs a thermal set point of about 40° C. by the use of heat resistors 710 and a feedback thermistor 711. In an exemplary construction, the heat resistors 710 include four 390 ohm ½ W surface mount resistors that are in parallel. In alternative embodiments, other numbers of heat generators 710 and/or other types of heat generators 710 (such as screened resistors, thick film resistors, heater tape, etc.) can be employed. In addition, alternative embodiments can utilize other forms of temperature control. Notable methods of temperature control use one or more thermistor, thermocouple, RTD, and/or other solid-state temperature measurement device for temperature control. Preferred embodiments, however, utilize a thermistor 711 in view of the lower costs.

A notable advantage of heating the membrane surfaces is the prevention of moisture condensation at the sensor surface. When a condensation layer is formed, the condensation layer can cause optical scattering and aberrations at the sensor surface, which substantially reduce measurement accuracy when utilizing, for example, an fluorescence amplitude mode based measurement. The condensation layer can also reduce the gaseous response time of the sensor because the mass diffusion properties at the sensor surface can be altered. It should be noted that by measuring the time-decay or phase properties of the fluorochrome, the accuracy of the sensor can be improved because the measurement is substantially not affected by amplitude variation. The time-decay or phase mode of measurement does not, however, mitigate any response time degradation because this is diffusion based at the sensor surface.

This embodiment can also provide other notable advantages that are particularly beneficial for use in, for example, the preferred, but non-limiting, embodiments as an oxygen sensor, as well as in other applications. In particular, a significant advantage of this embodiment (and in other embodiments described herein as well) is the ability of the sensor to respond extremely quickly to a step change in critical respiratory gasses such as oxygen and $CO_2$. With this embodiment, response rates of 100 milliseconds or faster (some as fast as 30–40 milliseconds) can be achieved, enabling an almost real-time determination of respiratory gas content (here: response time is defined as the time required for the output of the sensor to change from 10% to 90% of steady-state level upon application of a step change in the partial pressure of the gas in question).

The ability of this embodiment to, for example, observe and measure substantially real-time waveforms and oxygen levels from inhaled and exhaled respiratory gasses has significant medical utility. A respiratory gas sensor with this fast response characteristic can be utilized, for example, in conjunction with flow or volume measuring devices to determine the uptake and release of respiratory gasses, enabling the measurement of critical medical parameters such as metabolic rate (calorie expenditure), indirect cardiac output based on the Fick principle (first described in theory by Adolph Fick in 1870), pulmonary function, and onset of shock. Many of these medical diagnostic determinations require the measurement of the partial pressure respiratory gasses at the very end of an exhalation (known as end-tidal pO2 or end-tidal pCO2 levels). Because the amount of time between the end of a normal exhalation and the inhalation of the next breath is extremely short, a very fast response sensor can be important to determine end-tidal levels which have not been already affected by the inhalation of fresh air from the subsequent next breath. In addition to having a sensor with a sufficiently fast response time to a change in gas concentration, the sensor should also have the ability to compensate equally quickly to the changes in the temperature and humidity levels in the inspired and expired gasses. In the preferred embodiments, this has been achieved through the employment of a reference channel, as illustrated. The present invention is also advantageous in that it enables medical diagnostic procedures to be performed non-invasively and without the need for expensive analytical instruments that are otherwise currently used to make similar determinations with the current art.

Figures 28A, 28B:
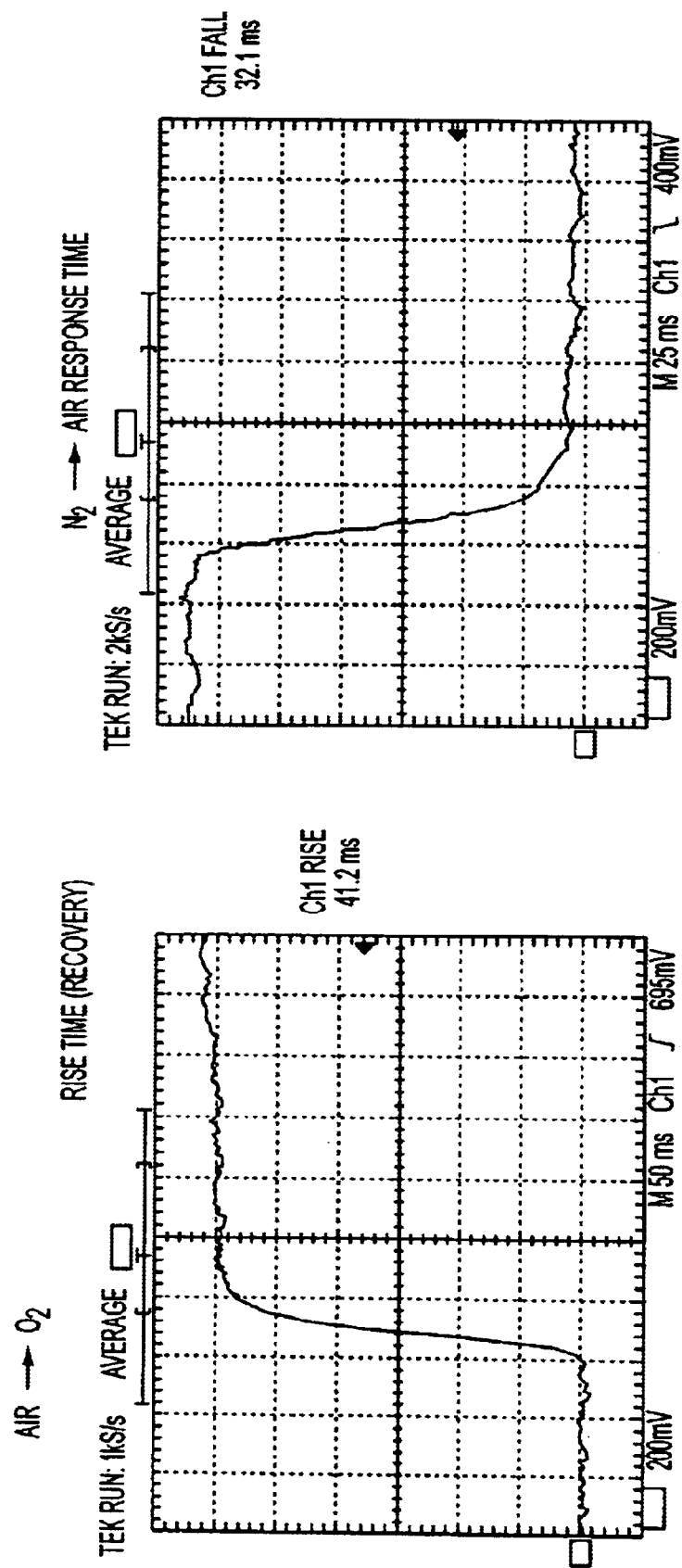
FIGS. 28(A) and 28(B) illustrate actual test data of a step change in the partial pressure of a gas in one exemplary construction of the embodiment of FIGS. 27(A)—27(C).

FIGS. 28(A) and 28(B) illustrate actual test data of a step change in the partial pressure of a gas in one exemplary construction of the embodiment of FIGS. 27(A)–27(C). In particular, FIGS. 28(A) and 28(B) depict actual response time determinations employing a construction of this embodiment for use in the, non-limiting, example as an oxygen sensor. FIG. 28(A) is a measurement of the response time of the sensor to a step change from ambient air (approximately 21% oxygen) to 100% oxygen which was supplied from a certified compressed gas cylinder (the response time of a sensor from a lower to a higher analyte concentration is typically referred to as "recovery time"). FIG. 28(B) is a measurement of the response time of the same sensor to a step change from 100% nitrogen supplied from a certified compressed gas cylinder to ambient air. The recovery and response times were, in these illustrative but non-limiting examples, about 41.2 and 32.1 milliseconds (as shown), respectively, as determined with a Tektronix Model TDS™ two channel oscilloscope. Preferably, recovery and response times are under about 100 milliseconds, and more preferably under about 80 milliseconds, and even more preferably under about 60 milliseconds. Preferred embodiments have a range of about 40 to 80 milliseconds.

In operation, the sensor 1000 operates like the two channel embodiments described herein-above. In this embodiment, however, the heat generators 710 impart heat to the heating element 1400 which in turn acts as a spreader to distribute heat within the sensor and within the membranes 14-1 and 14-2.

The cover 1200 is preferably formed from an insulating material, e.g., from an elastomer such as plastic or the like. In this manner, the cover 1200 can help conserve heat and maintain a temperature of the membranes. As a result, the heater does not need to work as hard or to consume as much power to operate. In the illustrated embodiment, the membranes 14-1 and 14-2 are also preferably recessed below a top surface of the hole 1220 when assembled as shown in FIG. 27(A) so that the membranes are less likely to be subject to external factors or to become damaged. The cover 1200 can be made, for example, by injection molding or by another appropriate means.

The cover 1200 is optional and can be eliminated in some cases. However, the cover 1200 is preferred because it can advantageously provide insulating properties for the heating element 1400, enabling the use of a smaller heating element and improved uniformity of heat distribution to the sensing and reference membranes, especially under conditions of rapid thermal changes and/or high flow velocities in the medium in which the analyte is contained. The cover is, thus, preferably installed over the sensor to assist in the performance of the heating element 1400 and/or to direct gases at the membrane surfaces.

As indicated, the sensor 1000 preferably utilizes two photosensitive elements 20-1 and 20-2. Preferably, the photosensitive element 20-1 detects oxygen signal fluorescence from a indicator channel membrane 14-1 and the photosensitive element 20-2 detects a signal from the reference channel membrane 14-2. Preferably, the reference channel membrane 14-2 is substantially not sensitive to oxygen, but is sensitive to temperature to substantially the same extent as the signal channel membrane 14-1. This is a notable feature in cases where the device is used for detecting oscillatory breathing (i.e., inhale/exhale) of a human or another animal because of the temperature and water vapor changes. With this embodiment, the temperature equilibrium of the indicator and reference channels can be maintained via the heating element 1400.

In the illustrated example, the membranes 14-1 and 14-2 are each preferably made with a borosilicate glass substrate of substantially equal thickness. Preferably, the membranes 14-1 and 14-2, thus, have similar thermal properties. A preferred matrix for the sensing of gaseous or dissolved oxygen or other gasses is an inorganic polymer support matrix termed sol-gels or ormosils, into which the indicator molecule is immobilized or entrapped. These materials and techniques are well known (See, e.g.: McDonagh et al., "Tailoring of Sol-Gel Films for Optical Sensing of Oxygen in Gas and Aqueous Phase", Analytical Chemistry, Vol. 70, No. 1, Jan. 1, 1998, pp. 45–50; Lev. O. "Organically Modified Sol-Gel Sensors", Analytical Chemistry, Vol. 67, No. 1, Jan. 1, 1995; MacCraith et al., "Development of a LED-based Fibre Optic Oxygen Sensor Using a Sol-Gel-Derived Coating", SPIE, Vol. 2293, pp. 110–120 ('94); Shahriari et al., "Ormosil Thin Films for Chemical Sensing Platforms", SPIE, Vol. 3105, pp. 50–51 ('97); Krihak et al., "Fiber Optic Oxygen Sensors Based on the Sol-Gel Coating Technique", SPIE, Vol. 2836, pp. 105–115 ('96), the entire disclosures of which are each incorporated herein by reference). These types of membranes can be applied to the appropriate substrate by a number of techniques that are well known in the art, such as dipping, swabbing, squeegeeing, silk screening, pad printing, vapor deposition, ink-jet printing, etc. These types of membranes can also be advantageously incorporated into any other embodiment of the invention described herein where appropriate.

Preferably, each membrane is, thus, formed with a glass (e.g., borosilicate glass) substrate that is coated with a thin-film sol-gel matrix coating that utilizes the same base chemistry in each membrane. Preferably, the reference membrane 14-2 is further processed to block oxygen diffusion. In examples of this embodiment for sensing $O_2$, a preferred indicator molecule includes, as one example, tris (4,7-diphenyl-1,10-phenanthroline) ruthenium (II) perchlorate molecule, discussed on column 1, line 17, of U.S. Pat. No. 5,517,313, the disclosure of which is incorporated herein by reference in its entirety. It is contemplated that the membranes can include a variety of other materials as set forth herein-above in other embodiments of the invention.

The radiation source preferably includes an LED (e.g., blue) that is mounted such that its light output is waveguided to the indicator and reference channel membranes 14-1 and 14-2 through the waveguide material within the region R. In an exemplary embodiment, the waveguide material is Epoxy Technologies 301™ which has good optical characteristics, although other appropriate materials could also be used. Preferably, fluorescent emissions from the membranes are similarly waveguided to the photosensitive elements 20-1 and 20-2 which are mounted on the substrate 700. Preferably, an optical filter 34 is provided for each of the photosensitive elements. In exemplary embodiments, as described above, each optical filter 34 can include a filter epoxy, such as filter resin available from CVI Laser, with, for example, a 600 nm cutoff surrounding the photosensitive elements. Other appropriate filters could be employed as discussed herein-above. The optical filters 34 preferably separate fluorescent emission from the membrane from the excitation energy of the radiation source 18 (e.g., a blue LED). As should be understood based on the foregoing, most preferably, the complete optical path (e.g., between the waveguide material in the region R and the membranes 14-1 and 14-2, etc.) is refractive index matched so that maximum light capture with minimal internal reflection losses occur.

While FIGS. 27(A) and 27(B) show the excitation source centrally located between the photosensitive elements 20-1 and 20-2 and the indicator and reference membranes 14-1 and 14-2, the excitation source 18 may be otherwise located, as long as adequate excitation is provided to the indicator and reference membranes 14-1 and 14-2.

As with other embodiments described herein, it is contemplated that the embodiment shown in FIGS. 27(A)–27(B) can be modified in a variety of ways. For instance, a heating element can be provided in embodiments where no control channel is used. In addition, as noted, an internal heater can be applied within a variety of sensor constructs in order to reduce condensation on a periphery of a sensor, especially upon sensing membranes or the like. In addition, other embodiments can include other known heating methods. For example, heating coils, wires or the like can be distributed within the sensor, preferably at least partly proximate the position of the indicator membranes.

In yet another embodiment of the present invention, the sensor 10 has a matrix that contains indicator molecules that possess one or more monomeric functions and which are copolymerized with one or more hydrophilic monomers to create a copolymer matrix layer which is suitable for the detection of analytes in aqueous environments. A polymeric matrix of this type is preferably prepared as described in U.S. patent application Ser. Nos. 09/632,624 and 09/920, 627, both of which are incorporated herein by reference. The matrix layer in accordance with this aspect of the present invention preferably takes the form of a water-soluble liquid polymeric matrix encased within an additional biocompatible layer which prohibits the leakage of the liquid polymeric matrix into the environment. As just one example of a suitable liquid polymeric matrix, U.S. patent application Ser. Nos. 09/632,624 and 09/920,627 describe the preparation of water-soluble-copolymeric solutions of MAPTAC [3-(methacryloylamino)propyl]trimethylammonium chloride and 9-[[N-methacryloylaminopropyl-N-(o-boronobenzyl)amino]methyl] anthracene.

As another example, U.S. patent application Ser. No. 09/920,627 describes the preparation of water-soluble copolymeric solutions of 9-[N-[2-(5,5-dimethylborinan-2-yl)benzyl]-N-[2-(2-methacroyloxy-ethoxy)ethylamino]methyl]-10-[N-[2-(5,5-dimethylborinan-2-yl)benzyl]-N-[2-(2-hydroxyethoxy)ethylamino]methyl] anthracene and [2-(methacryloxy)ethyl]trimethyl-ammonium chloride (TMAMA).

As is preferred for all indicator matrix constructs, the polymeric matrix of this embodiment is permeable to the analyte(s) to be sensed.

Figure 29A:
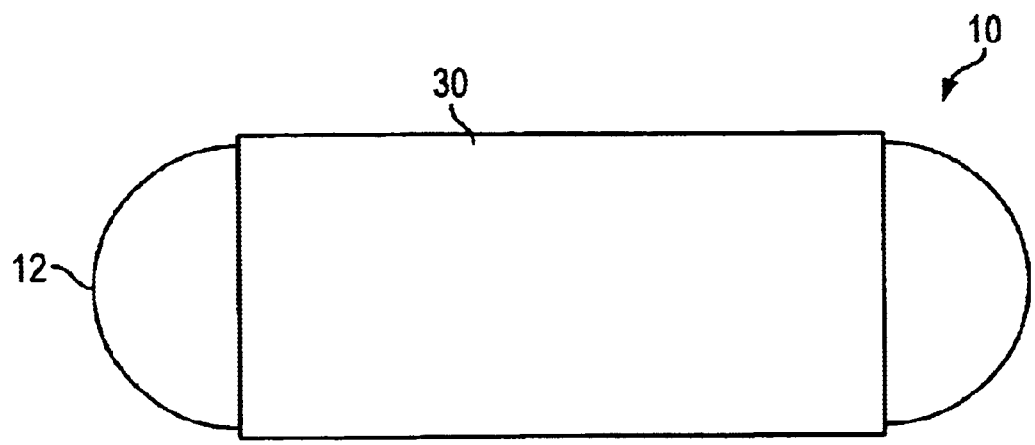
FIG. 29(A) illustrates another embodiment of the sensor having a matrix containing indicator molecules that possess one or more monomeric functions and which are copolymerized with one or more hydrophilic monomers to create a copolymer matrix layer which is suitable for the detection of analytes in aqueous environments.
Figure 29B:
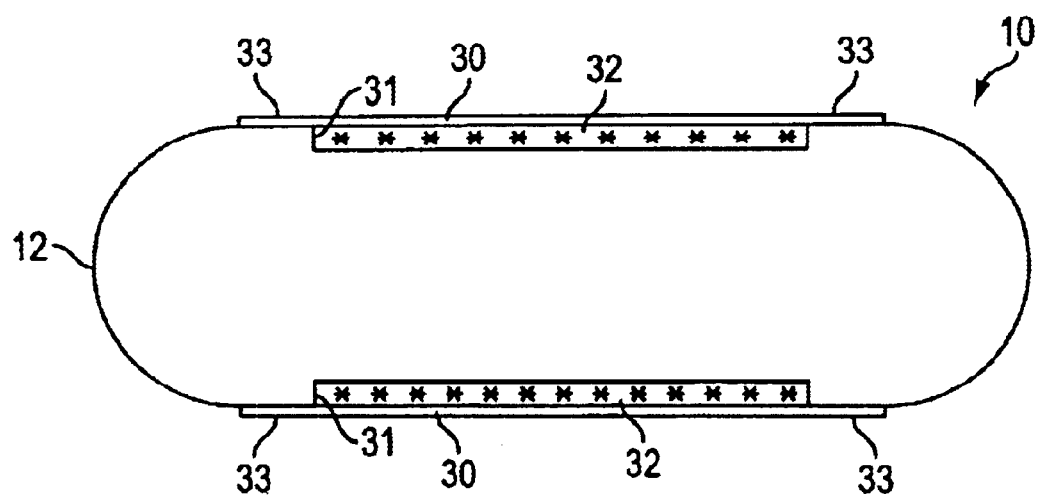
FIG. 29(B) is a cross section of the sensor shown in FIG. 29(A).

In one embodiment of the present invention, illustrated in FIGS. 29(A) and 29(B), the matrix layer 32 is a water-soluble liquid polymeric matrix that is preferably contained in a recessed portion 31 of the sensor body 12. A cover layer 30 is used to cover and contain the water-soluable liquid polymeric matrix 32, thereby preventing the escape and dissolution of that indicator matrix. The cover layer 30 is constructed to have a suitable size and shape to cover the recessed portion 31 and prevent the escape of the liquid polymer matrix. In a preferred embodiment, the cover layer 30 has a tubular shape having an inside diameter closely matching the outermost diameter of the sensor body 12. The cover layer 30 is permeable to the analyte(s) to be sensed and is biocompatable.

The cover layer 30 also preferably has a molecular weight cut-off which is smaller than the nominal molecular weight of the liquid polymeric matrix 32. Cover layer 30 is preferably a dialysis membrane such as, for example, a cellulose acetate dialysis membrane (MWCO 3500). Other suitable dialysis membranes may be selected depending upon the molecular weights of the liquid polymeric matrix and analytes of interest.

In a preferred embodiment of the invention illustrated in FIGS. 29(A) and 29(B), the sensor 10 is constructed by sliding or slip-fitting the cover layer 30 over a portion of the annular recess 31 designed to contain the indicator matrix 32. A predetermined quantity of concentrated, dry water-soluble polymer matrix is dispensed into the pocket created by the recess 31 and the cover layer 30. The cover layer is then further slid or slip-fit over the remainder of the annular recess 3 land into a final position as shown in FIGS. 29(A) and 29(B). The cover layer 30 is then heat sealed or otherwise bonded to the sensor body 12 in regions 33. The sensor is then immersed in an appropriate aqueous solution, allowing the solution to dissolve the dry water-soluble polymer into an aqueous form of the desired concentration. If necessary, a vacuum may be applied during this step to promote removal of any bubbles remaining within annular recess 31.

As indicated above, although specific embodiments of the various aspects of the invention have been described, numerous modifications and variations of these embodiments can be made by those in the art. For example, aspects of the various embodiments described herein-above can be applied or interchanged into other embodiments described above as would be apparent to those in the art based on this disclosure; for instance, the various embodiments can be adapted to have any one or more of the indicator molecules described herein-above (or that otherwise known) and can be adapted to use any of the control reference methods disclosed herein (or that otherwise known). As another example, it should be understood that various modifications of the electronics, etc., can be made by those in the art based on this disclosure, such as, for example, the various components can be incorporated onto an IC chip or other known modifications or techniques could be employed while maintaining one or more aspect of this invention.

In addition, where sensors are powered by and/or communicate with an external device, the external device can be made in a variety of forms depending on circumstances—for example, the external device could include: a wrist mounted enclosure (e.g., similar to a watch) that can be used in conjunction with a sensor implanted proximate a patient's wrist; a belt mounted or pants mounted enclosure (e.g., similar to a common "beeper") that can be used in conjunction with a sensor implanted proximate a patient's hip or waist; a blanket having internal electronics (e.g., similar to an electric blanket) upon which an individual can lay down with an implanted device proximate the blanket for, e.g., ease in obtaining readings while a patient sleeps; any structure which the sensor can be located near or brought proximate to and/or any structure which can be brought proximate to the sensor; or a variety of other structures and designs.

In addition, as described herein-above, the sensors of the various embodiments can be used in a variety of applications and environments—e.g., in any environment having one or more analyte that can be sensed. For example, the various embodiments could be employed within various mediums—including, gases (e.g., air and/or any other gases), liquids, solids, combinations thereof, etc. In addition, the various embodiments described herein may be readily employed in various applications and in various industries, such as in for example: the medical industry (e.g., where sensors may be, for example, inserted internally into a patient or animal); the food industry (e.g., such as where sensors can be inserted into liquids (e.g.: beverages, such as alcoholic beverages, e.g., wine, beer, etc., and non-alcoholic beverages; and various other liquids); creams; solids; etc.); the consumer products industry (e.g., where such sensing capabilities are appropriate); and in various other industries as described herein-above and as would be apparent based on this disclosure.

Accordingly, it should be understood that a variety of applications, modifications and variations can be made by those in the art within the scope of the following claims.

What is claimed is:

1. An optical-based sensor for determining the presence or concentration of an analyte in a medium, said sensor comprising:
   an enclosed sensor body having an outer surface surrounding said sensor body;
   a radiation source in said sensor body which emits radiation within said sensor body;
   an indicator element having an optical characteristic that is affected by the presence or concentration of an analyte, said indicator element comprising indicator molecules contained within a liquid polymeric matrix, and said indicator element being positioned on said sensor body to receive radiation that travels from said radiation source, and which transmits radiation into said sensor body;

a photosensitive element located in said sensor body and positioned to receive radiation within the sensor body and which emits a signal responsive to radiation received from said indicator element; and said sensor body being configured such that some of the radiation received by said photosensitive element is reflected internally within said sensor body before striking said photosensitive element.

2. The sensor of claim 1, wherein said indicator element is located in a recessed portion of said sensor body.

3. The sensor of claim 1, further comprising a cover layer which covers said liquid polymeric matrix and prevents the escape of said matrix.

4. The sensor of claim 3, wherein said cover layer has a tubular structure with an inside diameter closely matching an outermost diameter of said sensor body.

5. The sensor of claim 3, wherein said cover layer has a molecular weight cut-off that is smaller than a nominal molecular weight of said liquid polymer matrix.

6. The sensor of claim 3, wherein said cover layer is made of a dialysis membrane material.

7. The sensor of claim 3, wherein said cover layer is made of a biocompatible material.

8. The sensor of claim 1, wherein said liquid polymeric matrix comprises indicator molecules including 9-[[N-methacryloylaminopropyl-N-(o-boronobenzyl)amino]methyl] anthracene.

9. The sensor of claim 8, wherein said liquid polymeric matrix comprises a water-soluble-copolymeric solution of MAPTAC [3-(methacryloylamino)propyl]trimethylammonium chloride and 9-[[N-methacryloylaminopropyl-N-(o-boronobenzyl)amino]methyl] anthracene.

10. The sensor of claim 1, wherein said liquid polymerid matrix comprises a water-soluble compolymeric solution of 9-[N-[2-(5,5-dimethylborinan-2-yl)benzyl]-N-[2-(2-methacroyloxy-ethoxy)ethylamino]methyl]-10-[N-[2-(5,5-dimethylborinan-2-yl)benzyl]-N-[2-(2-hydroxyethoxy)ethylamino]methyl] anthracene and [2-(methacryloxy)ethyl]trimethyl-ammonium chloride.

11. The sensor of claim 1, wherein the optical characteristics of said indicator molecules vary as a function of the concentration of oxygen.

12. The sensor of claim 1, wherein said indicator molecules include light-absorbing indicator molecules.

13. The sensor of claim 1, wherein the optical characteristics of said indicator molecules vary as a function of the concentration of glucose.

14. The sensor of claim 1, wherein said indicator molecules include indicator molecules having an isosbestic point substantially at a particular wavelength and wherein a reference channel detects light substantially at the isosbestic wavelength.

15. The sensor of claim 1, wherein said indicator molecules interact with the radiation emitted by said radiation source by means of direct illumination.

* * * * *